(12) United States Patent
Soyka et al.

(10) Patent No.: US 7,989,616 B2
(45) Date of Patent: Aug. 2, 2011

(54) HIGH-PHOSPHATE STARCH

(75) Inventors: Stephan Soyka, Berlin (DE); Claus Frohberg, Kleinmachnow (DE)

(73) Assignee: Bayer Cropscience AG, Monheim Am Rhein (DE)

( * ) Notice: Subject to any disclaimer, the term of this patent is extended or adjusted under 35 U.S.C. 154(b) by 764 days.

(21) Appl. No.: 11/910,896

(22) PCT Filed: Apr. 7, 2006

(86) PCT No.: PCT/EP2006/003602
§ 371 (c)(1), (2), (4) Date: Oct. 5, 2007

(87) PCT Pub. No.: WO2006/108702
PCT Pub. Date: Oct. 19, 2006

(65) Prior Publication Data
US 2009/0270605 A1 Oct. 29, 2009

Related U.S. Application Data

(60) Provisional application No. 60/670,115, filed on Apr. 11, 2005.

(30) Foreign Application Priority Data

Apr. 8, 2005 (EP) .................................. 05090095

(51) Int. Cl.
*C08B 31/00* (2006.01)
*C08B 33/00* (2006.01)
*C12N 5/04* (2006.01)

(52) U.S. Cl. ......................... 536/102; 536/124; 435/417
(58) Field of Classification Search .................. 536/102, 536/124; 435/417
See application file for complete search history.

(56) References Cited

U.S. PATENT DOCUMENTS
2006/0130181 A1 * 6/2006 Hoehne et al. ................ 800/284

FOREIGN PATENT DOCUMENTS
| WO | WO 96/34968 | 11/1996 |
| WO | WO 00/08184 | 2/2000 |
| WO | WO 2004/056999 | 7/2004 |
| WO | WO 2004056999 A1 * | 7/2004 |
| WO | WO 2005/030942 | 4/2005 |

OTHER PUBLICATIONS

Abel, et al. (1996) The Plant Journal.
Hofvander, et al. (2004) Plant Biotechnology.
Jobling, et al. (1999) Plant Journal.
Kossmann, et al. (1991) Mol. Gen. Genet.
Lloyd, et al. (1999) Biochem. J.
Safford, et al. (1998) Carbohydrate Polymers.
Schwall, et al. (2000) Nature Biotechnology.
Slattery, et al. (2000) Trends in Plant Science.
International Preliminary Report on Patentability issued in International Application No. PCT/EP2006/003602, dated Oct. 9, 2007.

* cited by examiner

*Primary Examiner* — Shaojia Anna Jiang
*Assistant Examiner* — Everett White
(74) *Attorney, Agent, or Firm* — Hunton & Williams

(57) ABSTRACT

This invention relates to modified starches having an elevated content of phosphate and an elevated content of amylose.

19 Claims, 1 Drawing Sheet

HIGH-PHOSPHATE STARCH

CROSS-REFERENCE TO RELATED APPLICATIONS

This application is the U.S. National Stage filing of International Application No. PCT/EP2006/003602, filed Apr. 7, 2006, which claims benefit of European Patent Application No. 05090095.0, filed Apr. 8, 2005 and U.S. Provisional Patent Application No. 60/670,115, filed Apr. 11, 2005, the disclosures of each of which are hereby incorporated by reference.

BACKGROUND OF THE INVENTION (i) Field of the Invention

The invention relates to modified starches having an elevated content of phosphate and an elevated content of amylose.

(ii) Description of the Related Art

In view of the increasing importance which is currently being attached to plant components as renewable sources of raw material, one of the tasks of biotechnological research is to endeavor to adapt these plant raw materials to the requirements of the processing industry. In addition to this, it is necessary to achieve a great diversity of substances in order to enable renewable raw materials to be used in as many areas of employment as possible.

While the polysaccharide starch is composed of chemically uniform basic units, i.e. the glucose molecules, it is a complex mixture of different molecular forms which exhibit differences with regard to the degree of polymerization and branching and consequently differ greatly from each other in their physicochemical properties. A distinction is made between amylose starch, an essentially unbranched polymer composed of alpha-1,4-glycosidically linked glucose units, and amylopectin starch, a branched polymer in which the branches are formed as a result of the appearance of additional alpha-1,6-glycosidic linkages. Another important difference between amylose and amylopectin lies in their molecular weights. While amylose, depending on the origin of the starch, has a molecular weight of $5\times10^5$-$10^6$ Da, the molecular weight of amylopectin is between $10^7$ and $10^8$ Da. The two macromolecules can be differentiated by their molecular weight and their different physicochemical properties, something which can most readily be visualized by their different iodine-binding properties.

Amylose was regarded for a long time as being a linear polymer which consisted of alpha-1,4-glycosidically linked alpha-D-glucose monomers. However, more recent studies have demonstrated the presence of alpha-1,6-glycosidic branching points (approx. 0.1%) (Hizukuri and Takagi, Carbohydr. Res. 134, (1984), 1-10; Takeda et al., Carbohydr. Res. 132, (1984), 83-92).

Different methods are available for determining the amylose content. Some of these methods are based on the iodine binding ability of the amylose, which ability can be determined potentiometrically (Banks & Greenwood, in W. Banks & C. T. Greenwood, Starch and its components (pp. 51-66), Edinburgh, Edinburgh University Press), amperometrically (Larson et al., Analytical Chemistry 25(5), (1953), 802-804) or spectrophotometrically (Morrison & Laignelet, J. Cereal Sc. 1, (1983), 9-20). The amylose content can also be determined calorimetrically by means of DSC (differential scanning calorimetry) measurements (Kugimiya & Donovan, Journal of Food Science 46, (1981), 765-770; Sievert & Holm, Starch/Stärke 45 (4), (1993), 136-139). In addition, it is possible to determine the amylose content of native or debranched starch using SEC (size exclusion chromatography). This method has been recommended, in particular, for determining the amylose content of recombinantly modified starches (Gérard et al., Carbohydrate Polymers 44, (2001), 19-27).

The functional properties, such as the solubility, the retrogradation behavior, the ability to bind water, the film-forming properties, the viscosity, the pasting properties, the freeze/thaw stability, the acid stability, the gel strength and the grain size of starches are influenced, inter alia, by the amylose/amylopectin ratio, the molecular weight, the pattern of side chain distribution, the content of ions, the content of lipid and protein, the mean starch grain size, the starch grain morphology, etc. The functional properties of starch are also influenced by the content of phosphate, i.e. a non-carbon component of starch. In this connection, a distinction is made between phosphate which is covalently bonded in the form of monoesters to the glucose molecules of the starch (termed starch phosphate here) and phosphate in the form of phospholipids which are associated with the starch.

The content of starch phosphate varies in dependence on the plant type. Thus, for example, certain corn mutants synthesize a starch having an elevated content of starch phosphate (waxy corn 0.002% and high-amylose corn 0.013%) whereas conventional corn types only exhibit traces of starch phosphate. Small quantities of starch phosphate are also found in wheat (0.001%) whereas it has not been possible to detect any starch phosphate in oats and sorghum. Less starch phosphate has also been found in rice mutants (waxy rice 0.003%) than in conventional rice types (0.013%). Significant quantities of starch phosphate have been detected in plants, such as tapioca (0.008%), sweet potato (0.011%), arrowroot (0.021%) and potato (0.089%), which synthesize tuber storage starch or root storage starch. The percentage values for the starch phosphate content which are cited above are in each case based on the dry weight of the starch and were determined by Jane et al. (1996, Cereal Foods World 41 (11), 827-832). In general, the distribution of the phosphate in (native) starch which is synthesized by plants is characterized by from about 30% to 40% of the phosphate residues being covalently bonded in the C3 position, and from about 60% to 70% of the phosphate residues being covalently bonded in the C6 position, of the glucose molecules (Blennow et al., 2000, Int. J. of Biological Macromolecules 27, 211-218). By contrast, chemically phosphorylated starches additionally possess phosphate residues which are covalently bonded in the C2 position of the glucose molecules since the chemical reaction proceeds in a randomly directed manner.

Kossmann and Lloyd (2000, Critical Reviews in Plant Sciences 19(3), 171-126) provide a review of native starches which are isolated from different plant species in which enzymes involved in starch biosynthesis are reduced.

Plants in which the activity of an SSIII protein (Abel et al., 1996, The Plant Journal 10(6), 9891-991; Lloyd et al., 1999, Biochemical Journal 338, 515-521) or the activity of a BEI protein (Kossmann et al., 1991, Mol Gen Genet. 230, 39-44; Safford et al., 1998, Carbohydrate Polymers 35, 155-168) or the activity of a BEII protein (Jobling et al., 1999, The Plant Journal 18), or the activity of a BEI and BEII protein (Schwall et al., 2000, Nature Biotechnology 18, 551-554; WO 96/34968, Hofvander et al., 2004, Plant Biotechnology 2, 311-321), or the activity of a BEI protein and of an SSIII (WO 00/08184) protein are reduced have thus far been described.

As compared with corresponding wild-type plants, starches which are isolated from plants in which the activity of an SSIII protein is reduced exhibit a relative shift of the side chains of the amylopectin from relatively long chains to short chains (Lloyd et al., 1999, Biochemical Journal 338, 515-521), a phosphate content which is elevated by 70%, no change in the amylose content (Abel et al., 1996, The Plant Journal 10(6), 9891-991) and a decrease in the final viscosity in the RVA analysis (Abel, 1995, Berlin Free University Dissertation). As compared with starches which are isolated from untransformed wild-type plants, these starches, which are also described in WO 00/08184, exhibit a phosphate content which is increased by 197%, an amylose content which is increased by 123% and a final viscosity in the RVA analysis which falls to 76% of the wild type. In addition, the gel strength of the starch concerned falls to 84% of the wild type.

In the Morrison & Laignelet (1983, J. Cereal Sc. 1, 9-20) spectrophotometric analysis, starches which are isolated from plants which exhibit a reduced activity of both a BEI protein and a BEII protein have an amylose content of from 77% to 89.1% (corresponds to at most 348% of the starch which is isolated from wild-type plants) and a phosphorus content of from 2400 µg/g of starch (corresponds to 77.4 µmol of phosphate/g starch) to 3000 µg/g of starch (corresponds to 96.8 µmol of phosphate/g starch). This gives a maximum increase of 613% as compared with starch which is isolated from corresponding wild-type plants. Starches containing more than 55% amylose no longer exhibit any pasting (Schwall et al., 2000, Nature Biotechnology 18, 551-554). Starches having lower amylose values (40.9%) exhibit a final viscosity value which is increased by 256%, after pasting in the RVA analysis, and exhibit a phosphorus content of 206 mg/100 g of starch (corresponds to 66.4 µmol of phosphate/g of starch). Higher phosphorus contents, e.g. 240 mg of phosphorus/100 g of starch (corresponds to 77.4 µmol of phosphate/g of starch; WO 9634968), are only achieved when the relevant starches also exhibit higher amylose values. Hofvander et al. (2004, Plant Biotechnology 2, 311-321) describe starches which are isolated from genetically modified potato plants having a phosphorus content of from 2400 to 3300 µg/g of starch (corresponds to from 77.4 to 106.4 µmol of phosphate/g of starch), with the starches exhibiting an amylose content (spectrophotometric determination of the iodine-binding ability) of from 47% to 86%.

SUMMARY OF THE INVENTION

The present invention is based on the object of making available potato starches having novel properties, novel plant cells and/or plants which produce the starches, and also means and methods for generating said plant cells and/or plants.

This object is achieved by the provision of the embodiments which are described in the patent claims.

The present invention consequently relates to modified starch which is isolated from potato plants and which a) has an amylose content, as measured by the method of Hovenkamp-Hermelink et al. (1987, Theoretical and Applied Genetics 75, 217-221), of between 40% and 50%, and b) has a phosphorus content of from 80 to 95 µmol of phosphate per gram of starch (dry weight).

DETAILED DESCRIPTION OF THE INVENTION

The elevated quantities of starch phosphate in starches according to the invention confer surprising and advantageous properties on the starches. As a result of the increased content of starch phosphate, starches according to the invention carry an increased content of charged groups which have a substantial influence on the functional properties of the starch. Starch which carries charged functional groups can, in particular, be employed in the paper industry, where it is used for the surface coating of paper. Paper which is coated with charged molecules which also exhibit good adhesive properties (pasting properties) is particularly suitable for taking up dyes, such as ink, printing colors, etc.

The starches according to the invention are native starches. In connection with the present invention, the term "native starch" means that the starch is isolated from plants or starch-storing parts of plants using methods known to the skilled person.

In connection with the present invention, the amylose content is determined using the method of Hovenkamp-Hermelink et al. (Potato Research 31, (1988), 241-246) which is described for potato starch (see General Methods, item 1).

Within the meaning of the present invention, the term "phosphate content" of the starch denotes the content of phosphate which is covalently bonded in the form of starch phosphate monoesters.

Methods for determining the phosphate content are known to the skilled person and adequately described in the literature (e.g. Gericke and Kurmies, 1952, Z. Düngg. Pflanzenernähr. Bodenk. 59, 235-247). In connection with the present invention, preference is given to using the method which is described under General Methods, item 2.

Methods for isolating starch from plants or from starch-storing parts of plants are known to the skilled person. Furthermore, methods for extracting the starch from different starch-storing plants are described, for example, in Starch: Chemistry and Technology (Eds.: Whistler, BeMiller and Paschall (1994), 2nd edition, Academic Press Inc. London Ltd; ISBN 0-12-746270-8; see, for example, chapter XII, pages 412-468: corn and sorghum starches: preparation; by Watson; chapter XIII, pages 469-479: tapioca, arrowroot and sago starches: preparation; by Corbishley and Miller; chapter XIV, pages 479-490: potato starch: preparation and uses; by Mitch; chapter XV, pages 491 to 506: wheat starch: preparation, modification and uses; by Knight and Oson; and chapter XVI, pages 507 to 528: rice starch: preparation and uses; by Rohmer and Klem; corn starch: Eckhoff et al., Cereal Chem. 73 (1996), 54-57). On an industrial scale, corn starch is usually extracted by what is termed "wet milling".

Furthermore, the present invention relates to a method for the manufacture of the (potato) starch according to the invention, including the step of extracting the starch from a plant cell according to the invention or from a plant according to the invention, from propagation material according to the invention of such a plant and/or from harvestable plant parts according to the invention of such a plant, preferably from starch-storing parts according to the invention of such a plant. Preferably, such a method also includes the step of harvesting the cultivated plants or plant parts and/or the propagation material of these plants before the extraction of the starch and, further, particularly preferably the step of cultivating plants according to the invention before harvesting.

Starch phosphate can be present in the form of monoesters at the C3 or C6 position in the polymerized glucose monomers (Blennow et al., 2000, Int. J. of Biological Macromolecules 27, 211-218). The distribution of the phosphate in plant-synthesized starch is generally characterized by from about 30% to 40% of the phosphate residues being covalently bonded in the C3 position, and from about 60% to 70% of the phosphate residues being covalently bonded in the C6 position, of the glucose molecules (Blennow et al., 2000, Int. J. of Biological Macromolecules 27, 211-218). Starches according to the invention are characterized by exhibiting a phosphate distribution in which the C6 phosphate content based on the total phosphate content is increased.

A preferred embodiment of the present invention therefore relates to modified starch according to the invention which is characterized by having a C6 phosphorus content of from 45 to 60 µmol of phosphate per gram of starch (dry weight).

In connection with the present invention, the term "C6 phosphate content" is intended to be understood as being the quantity of starch phosphate which is covalently bonded in the C6 position in the glucose molecules of the starch.

In connection with the present invention, the term "total phosphate content" is intended to be understood as meaning the total quantity of starch phosphate which is covalently bonded to glucose molecules in the starch.

A variety of methods have been described for determining the quantity of C6 phosphate (e.g. Ritte et al., 2000, Starch/Stärke 52, 179-185). The use of $^{31}$P-NMR to determine the quantity of C6 phosphate is described in Kasemusuwan and Jane (1996, Cereal Chemistry 73, 702-707). Preference is given to using the Ames (Methods in Enzymology VIII, (1996), 115-118) method, with particular preference being given to using the method which is described under General Methods item 2.

Starches according to the invention are also characterized by exhibiting an altered amylopectin side-chain distribution as compared with starch (amylopectin) which is isolated from corresponding wild-type plants.

The invention therefore preferably relates to modified starch according to the invention which exhibits an altered amylopectin side-chain distribution as compared with starch which is isolated from corresponding wild-type plants.

In connection with the present invention, the term "wild-type plant" refers to plants whose genetic information, apart from genetic modifications which cause starch according to the invention to be synthesized, corresponds to that of the plant which synthesizes the starch according to the invention.

The side-chain distribution is determined by determining the percentage proportion of a particular group of side chains in the total content of all the side chains in a GPC chromatogram. For this purpose, the total area below the line of the GPC chromatogram is divided into individual segments which in each case represent groups of side chains of different length. The chosen segments contain side chains having the following degrees of polymerization (DP=number of glucose monomers within a side chain): DP less than 11, DP from 11 to 18, DP from 19 to 24, DP from 25 to 30, DP from 31 to 36, DP from 37 to 42, DP from 43 to 48, DP from 49 to 55, DP from 56 to 61, DP from 62 to 123 and DP greater than 123. In order to correlate the elution volume with the molar mass, the GPC column which is used is calibrated with dextran standards (Fluka, Product No. 31430). The dextrans which are used, their pertinent molar masses, and the elution volumes, are shown in FIG. 1. The calibration straight line which results from this is used to depict the elution diagram as a molecular weight distribution. For the purpose of determining the molecular weights of the individual side chains, glucose was specified to have a molecular weight of 162. The total area below the line in the GPC chromatogram is stipulated to be 100% and the proportions of the areas of the individual segments are calculated in relation to the proportion of the total area.

In connection with the present invention, the term altered "side-chain distribution" is intended to be understood as meaning a change in the proportion of the amylopectin side chains having a DP of less than 11, a DP of from 11 to 18, a DP of from 19 to 24, a DP of from 25 to 30, a DP of from 31 to 36, a DP of from 37 to 42, a DP of from 43 to 48, a DP of from 49 to 55, a DP of from 56 to 61, a DP of from 62 to 123 and/or a DP greater than 123, based on the quantity of the amylopectin side chains having the same degree of polymerization in starch which is isolated from corresponding wild-type plants.

Starch according to the invention is preferably characterized by the proportion of the amylopectin side chains having a DP of less than 11, a DP of from 11 to 18 and/or a DP of from 19 to 24 being reduced and by the proportion of the amylopectin side chains having a DP of from 56 to 61, a DP of from 62 to 123 and/or a DP of greater than 123 being increased, as compared with the amylopectin side chains having the same degree of polymerization in starch which is isolated from corresponding wild-type plants.

The proportion of the amylopectin side chains having a DP of less than 11 in starch according to the invention is preferably reduced by at least 65%, preferably at least 70%, particularly preferably at least 75% and very particularly preferably at least 80%, based on the quantity of the amylopectin side chains having a DP of less than 11 in starch which is isolated from corresponding wild-type plants.

The proportion of the amylopectin side chains having a DP of from 11 to 18 in starch according to the invention is preferably reduced by at least 40%, preferably at least 45%, particularly preferably at least 50% and very particularly preferably at least 53%, based on the quantity of the amylopectin side chains having a DP of from 11 to 18 in starch which is isolated from corresponding wild-type plants.

The proportion of the amylopectin side chains having a DP of from 19 to 24 in starch according to the invention is preferably reduced by at least 5%, preferably at least 10% and particularly preferably at least 15%, based on the quantity of the amylopectin side chains having a DP of from 19 to 24 in starch which is isolated from corresponding wild-type plants.

The proportion of the amylopectin side chains having a DP of from 56 to 61 in starches according to the invention is preferably increased by at least 20%, preferably at least 30%, particularly preferably at least 35% and very particularly preferably at least 40%, based on the quantity of the amylopectin side chains having a DP of from 56 to 61 in starch which is isolated from corresponding wild-type plants.

The proportion of the amylopectin side chains having a DP of from 62 to 123 in starches according to the invention is preferably increased by at least 100%, preferably at least 150%, particularly preferably at least 200% and very particularly preferably at least 230%, based on the quantity of the amylopectin side chains having a DP of from 62 to 123 in starch which is isolated from corresponding wild-type plants.

The proportion of the amylopectin side chains having a DP of greater than 123 in starches according to the invention is preferably increased by at least 700%, preferably at least 800%, particularly preferably at least 900% and very particularly preferably at least 1000%, based on the quantity of the amylopectin side chains having a DP of greater than 123 in starch which is isolated from corresponding wild-type plants.

Starch according to the invention possesses the property that it exhibits an elevated final viscosity in the RVA analysis when the RVA analysis is carried out in an aqueous solution containing $CaCl_2$. In this connection, the addition of $CaCl_2$ causes the starch to be completely pasted.

The present invention therefore preferably relates to starch according to the invention which, after pasting in the RVA analysis in the added presence of $CaCl_2$, exhibits a final viscosity which is increased as compared with starch which is isolated from wild-type plants and which is pasted under identical conditions. The RVA analysis is preferably carried out in the added presence of at least 1.5 M $CaCl_2$, particularly preferably of at least 2 M $CaCl_2$ and very particularly preferably of at least 2.5 M $CaCl_2$.

Protocols for carrying out the RVA (rapid visco analyzer) analysis are described below under General Methods, item 4. It should be pointed out, in particular, that an 8% starch suspension (w/w) is frequently employed in the RVA analysis of potato starches. The documents (Directions for use, Newport Scientific Pty Ltd., Investment Support Group, Warried NSW 2102, Australia) which are enclosed with the "RVAsuper3" appliance recommend a suspension containing approx. 10% starch for analyzing potato starch. Surprisingly, it was found, in the case of potato plant-derived starch and concerning the present invention, that it was not possible to use an 8% starch suspension (2 g of starch intended for 25 ml of water) for the analysis because the final viscosity reached values which the appliance was no longer able to register. For this reason, starch suspensions of only 6% strength (1.5 g of starch in 25 ml of water) were used for the RVA analysis instead of 8% starch suspensions. In connection with the present invention, therefore, an increased final viscosity in the RVA analysis is intended to be understood as meaning an increase by at least 100%, particularly by at least 120%, in particular by at least 140%, as compared with wild-type plants which are not genetically modified. In this connection, the increase in the final viscosities is to be related to 6% starch suspensions which were carried out in an aqueous $CaCl_2$ solution. In connection with the present invention, preference is given to using the RVA analytical method 1, which is described under General Methods, item 4, for determining the final viscosity in the RVA analysis.

It was furthermore found that starches according to the invention exhibit an elevated pasting temperature in the RVA analysis.

A preferred embodiment of the present invention therefore relates to starch according to the invention which exhibits an elevated pasting temperature in the RVA analysis. The pasting temperature of starch according to the invention is preferably at least 80° C., preferably at least 85° C., particularly preferably at least 90° C. and very particularly preferably at least 92° C. In connection with the present invention, the pasting temperature is preferably carried out using the RVA analytical method 3 which is described under General Methods, item 4.

Starches having an elevated pasting temperature offer the advantage that they can be more readily dispersed in heated liquids. Starch according to the invention is therefore particularly suitable for producing foodstuffs, with starch being added, for example as a thickener, to heated foodstuff preparations.

Following pasting, starch according to the invention preferably forms gels whose strength is increased.

In another preferred embodiment, the present invention relates to starch according to the invention which, after pasting in water, forms a gel which exhibits a gel strength which is increased as compared with that of a gel composed of starch which is isolated from wild-type plants. Particularly preferably, starch according to the invention forms, after pasting in an aqueous $CaCl_2$ solution, a gel which develops a final viscosity which is increased as compared with that of a gel composed of starch which is isolated from corresponding wild-type plants.

The advantage of starch according to the invention, as compared with conventional starch, is that, after pasting in salt-containing solutions, it forms stronger gels than does conventional starch. For this reason, starch according to the invention is particularly suitable for applications in the foodstuffs sphere, where starch is frequently employed as a thickener. As a rule, foodstuffs contain salts. Less starch according to the invention than conventional starch therefore has to be used for thickening foodstuffs. This saves costs and reduces the calorie content of foodstuffs which contain starch according to the invention as compared with foodstuffs which contain conventional starch.

In connection with the present invention, the term "increased gel strength" is intended to be understood as meaning an increase in the gel strength, preferably by at least 20%, in particular by at least 40%, more preferably by at least 60%, and particularly preferably by at least 90%, as compared with the gel strength of starch which is isolated from wild-type plants.

In connection with the present invention, the gel strength is to be determined using a texture analyzer in the method which is described under General Methods, item 3.

In order to prepare starch gels, the crystalline structure of native starch first of all has to be destroyed by heating in aqueous suspension while stirring continuously. This can be carried out using a rapid visco analyzer (Newport Scientific Pty Ltd., Investment Support Group, Warriewod NSW 2102, Australia). As already explained above, in the case of potato plant-derived starch according to the invention a 6% starch suspension, instead of the 8% suspension used as standard, was employed, in this connection. In order to determine the gel strength, the starch suspensions which are pasted in the rapid visco analyzer are stored for a certain time and then subjected to an analysis using a texture analyzer. Consequently, 6%, instead of 8%, pasted starch suspensions were also used for determining the gel strength.

The starch according to the invention, preferably native potato starch, can, after having been extracted from plants or starch-containing plant parts, be modified chemically and/or physically using standard methods which are known to the skilled person.

In this connection, starch according to the invention offers the advantage that it can be derivatized at relatively high temperatures since, as already described above, it exhibits a higher pasting temperature than does conventional starch. As a result, the reactions, for example in connection with chemical derivatization, can take place at higher temperatures, with this leading to the reactions proceeding more efficiently without the structure of the starch grain being destroyed.

Furthermore, starch according to the invention offers the advantage that it is better suited for being the starting substance for the derivation than are conventional starches (e.g. isolated from wild-type potato plants) because, as a result of its higher content of covalently bonded starch phosphate, it exhibits a higher proportion of reactive, functional groups, is more strongly hydrophilic and is more readily accessible to chemical agents.

The present invention therefore also relates to methods for preparing a derivatized starch, wherein starch according to the invention is subsequently derivatized.

In connection with the present invention, the term "derivatized starch" is intended to be understood as meaning a starch according to the invention whose properties have been altered using chemical, enzymatic, thermal or mechanical methods after it has been isolated from plant cells.

In a preferred embodiment of the present invention, the derivatized starch according to the invention is heat-treated and/or acid-treated starch.

In another preferred embodiment, the derivatized starches are starch ethers, in particular starch alkyl ethers, O-allyl ethers, hydroxylalkyl ethers, O-carboxylmethyl ethers, nitrogen-containing starch ethers, phosphate-containing starch ethers or sulfur-containing starch ethers.

In another preferred embodiment, the derivatized starches are crosslinked starches.

In another preferred embodiment, the derivatized starches are starch-graft polymers.

In another preferred embodiment, the derivatized starches are oxidized starches.

In another preferred embodiment, the derivatized starches are starch esters, in particular starch esters which have been introduced into the starch using organic acids. Particularly preferably, the starch esters are phosphate starches, nitrate starches, sulfate starches, xanthate starches, acetate starches or citrate starches.

Methods for preparing derivatized starches according to the invention are known to the skilled person and are adequately described in the general literature. Orhoefer (in Corn, Chemistry and Technology, 1987, eds. Watson and Ramstad, chapter 16, 479-499), for example, provides a review of the preparation of derivatized starches.

The present invention also relates to derivatized starch which can be obtained using the method according to the invention for preparing a derivatized starch.

The present invention also relates to the use of starch according to the invention for preparing derivatized starch.

Starch according to the invention can be prepared by isolation from genetically modified plants or plant cells which exhibit an activity of one or more SSIII proteins which occur endogenously in the plant or plant cell and of one or more BEI proteins which occur endogenously in the plant or plant cell and of one or more BEII proteins which occur endogenously in the plant or plant cell and of one or more proteins which occur endogenously in the plant or plant cell and which exhibit the amino acid sequence specified under SEQ ID NO 12 or SEQ ID NO 14, which is reduced as compared with that of corresponding wild-type plants or plant cell which are not genetically modified.

The invention therefore also relates to genetically modified plants or plant cells which synthesize a starch according to the invention and which exhibit an activity
a) of one or more SSIII proteins which occur endogenously in the plant or plant cell, and
b) of one or more BEI proteins which occur endogenously in the plant or plant cell, and
c) of one or more BEII proteins which occur endogenously in the plant or plant cell, and
d) of one or more proteins which occur endogenously in the plant or plant cell and which exhibit an at least 80% identity with the amino acid sequence specified under SEQ ID NO 12 or SEQ ID NO 14,
which is reduced as compared with that of corresponding wild-type plants or plant cells which are not genetically modified.

The invention further relates to genetically modified plants or plant cells which exhibit an activity
a) of one or more SSIII proteins which occur endogenously in the plant or plant cell, and
b) of one or more BEI proteins which occur endogenously in the plant or plant cell, and
c) of one or more BEII proteins which occur endogenously in the plant or plant cell, and
d) of one or more proteins which occur endogenously in the plant or plant cell and which exhibit an at least 80% identity with the amino acid sequence specified under SEQ ID NO 12 or SEQ ID NO 14,
which is reduced as compared with that of corresponding wild-type plants or plant cells which are not genetically modified.

Plants or propagation material of plants according to the invention comprising plant cells according to the invention are also an object of the invention.

Here, the term "propagation material" encompasses those components of the plant which are suitable for producing progeny in a vegetative or sexual manner. Suitable for vegetative propagation are, for example, cuttings, callus cultures, rhizomes or tubers. Other propagation material encompasses, for example, fruits, seeds, seedlings, protoplasts, cell cultures, etc. Preferred propagation materials are tubers, fruits or seeds.

In a further embodiment, the present invention relates to harvestable plant parts of plants according to the invention, such as fruits, storage roots, roots, flowers, buds, shoots, leaves or stems, preferably seeds, fruits or tubers, where these harvestable parts comprise plant cells according to the invention.

In connection with the present invention, the term "genetically modified" means that the genetic information of the plant cell has been altered.

In this connection, the genetic modification can be any genetic modification which leads to a reduction in the activity of one or more SSIII proteins which occur endogenously in the plant or plant cell and to a reduction in the activity of one or more BEI proteins which occur endogenously in the plant or plant cell and to a reduction in the activity of one or more BEII proteins which occur endogenously in the plant or plant cell and to a reduction in the activity of one or more proteins which occur endogenously in the plant or plant cell, and which exhibit the amino acid sequence specified under SEQ ID NO 12 or SEQ ID NO 14, as compared with corresponding wild-type plants or plant cells which are not genetically modified.

In connection with the present invention, the term "corresponding" means that, when several objects are being compared, the objects in question, which are being compared with each other, are kept under identical conditions. In connection with the present invention, the term "corresponding" means, in connection with a wild-type plant, that the plants which are being compared with each other were grown under identical cultural conditions and that they are of the same (cultural) age.

In this connection, the term "reduction in the activity" means, in the context of the present invention, a reduction in the expression of endogenous genes which encode SSIII proteins and/or BEI proteins and/or BEII proteins and/or proteins which exhibit the amino acid sequence specified under SEQ ID NO 12 or SEQ ID NO 14, and/or a reduction in the quantity of SSIII protein, BEI protein, BEII protein and/or protein which exhibits the amino acid sequence specified under SEQ ID NO 12 or SEQ ID NO 14, in the plants or plant cells, and/or a reduction in the enzymatic activity of the SSIII proteins, BEI proteins, BEII proteins and/or proteins which exhibit the amino acid sequence specified under SEQ ID NO 12 or SEQ ID NO 14, in the plants or plant cells as compared with the corresponding wild-type plants or plant cells which are not genetically modified.

The reduction in the expression can, for example, be determined by determining the quantity of coding transcripts of SSIII proteins, BEI proteins, BEII proteins or proteins which exhibit the amino acid sequence specified under SEQ ID NO 12 or SEQ ID NO 14. This can be effected, for example, by means of Northern Blot analysis or RT-PCR. In this connection, a reduction preferably means a reduction in the quantity of transcripts, as compared with corresponding plants or plant cells which are not genetically modified, by at least 50%, in particular by at least 70%, preferably by at least 85% and particularly preferably by at least 95%. The reduction in the quantity of SSIII proteins, BEI proteins, BEII proteins and/or proteins which exhibit the amino acid sequence specified under SEQ ID NO 12 or SEQ ID NO 14, which results in a reduced activity of these proteins in the plant cells or plants concerned, can be determined, for example, by means of immunological methods such as Western Blot analysis, ELISA (enzyme-linked immunosorbent assay) or RIA (radio immuno assay). In this connection, a reduction preferably means a reduction in the quantity of SSIII protein, BEI protein, BEII protein and/or protein which exhibits the amino acid sequence specified under SEQ ID NO 12 or SEQ ID NO 14 by at least 50%, in particular by at least 70%, preferably by at least 85%, and particularly preferably by at least 95%, as compared with corresponding plants or plant cells which are not genetically modified.

In connection with the present invention, "SSIII protein" is to be understood as meaning a class of soluble starch synthases (ADP-glucose 1,4-alpha-D-glucan 4-alpha-D-glucosyltransferase; EC 2.4.1.21). Soluble starch synthases catalyze a glycosylation reaction in which glucose residues of the substrate ADP-glucose are transferred to alpha-1,4-linked glucan chains with the formation of an alpha-1,4-linkage (ADP-glucose+{(1,4)-alpha-D-glucosyl}(N)⇔ADP+{(1,4)-alpha-D-glucosyl}(N+1)).

SSIII proteins are described, for example, in Marshall et al. (The Plant Cell 8; (1996); 1121-1135), Li et al. (2000, Plant Physiology 123, 613-624), Abel et al. (The Plant Journal 10(6); (1996); 981-991) and in WO 0066745. The structure of SSIII proteins frequently exhibits a sequence of domains. SSIII proteins have a signal peptide at the N terminus for transport of the proteins into plastids. There then follow, in the direction of the C terminus, an N-terminal region, an SSIII-specific region and a catalytic domain (Li et al., 2000, Plant Physiology 123, 613-624). Other analyses based on primary sequence comparisons (http://hits.isb-sib.ch/cgi-bin/PFS-CAN) have shown that the potato SSIII protein possesses a carbohydrate-binding domain (CBM). This domain (Pfam Motiv cbm 25) comprises amino acids 377 to 437 of the potato SSIII protein sequence depicted in SEQ ID NO 2. Therefore, in connection with the present invention, an SSIII protein is intended to be understood as meaning starch synthases which exhibit an identity of at least 50%, preferably of at least 60%, particularly preferably of at least 70%, more preferably of at least 80% and in particular of at least 90%, with the sequence depicted in SEQ ID NO 3.

The term homology or identity is intended to mean the number of amino acids which are congruent (identity) with those of other proteins, expressed as a percentage. Preference is given to using computer programs to determine the identity by comparing SEQ ID NO 3 with other proteins. If sequences which are being compared with each other are of different lengths, the identity is then to be ascertained by the number of amino acids which the shorter sequence has in common with the longer sequence determining the percentage identity. The identity can, as a standard, be ascertained using computer programs such as ClustalW (Thompson et al., Nucleic Acids Research 22 (1994), 4673-4680) which are known and available to the public. ClustalW is made publicly available by Julie Thompson (Thomson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from various internet sites, inter alia from the IGBMC (Institut de Génétique et de Biologie Moléculaire et Cellulaire, B. P. 163, 67404 Illkirch Cedex, France; ftp://ftp-igbmc.u-strasbg.fr/pub/) and from EBI (ftp://ftp.ebi.ac.uk/pub/software/) as well as all the mirrored EBI (European Bioinformatics Institute, Wellcome Trust Genome Campus, Hinxton, Cambridge CB10 1SD, UK) internet sites.

When version 1.8 of the ClustalW computer program is being used in order to determine the identity between, for example, the reference protein of the present application and other proteins, the following parameters are to be set: KTUPLE=1, TOPOIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

One option for finding similar sequences is to carry out sequence database searches. In the searches, one or more sequences are predetermined to be what is termed the query. Statistical computer programs are then used to compare this query sequence with sequences which are contained in the chosen databases. Such database searches (blast searches) are known to the skilled person and can be carried out using the databases provided by different suppliers. If such a database search is carried out using the NCBI (National Center for Biotechnology Information, http://www.ncbi.nlm.nih.gov/) database, the standard settings which are predetermined for the given comparison query should then be used. In the case of protein sequence comparisons (blastp), these settings are as follows: limit entrez=not activated; filter=low complexity activated; expect value=10; word size=3; matrix=BLOSUM62; gap costs: existence=11, extension=1. Such a search also results in the percentage identity between the query sequence and the similar sequences which are found in the databases being presented in addition to other parameters.

In connection with the present invention, therefore, an SSIII protein is intended to be understood as meaning starch synthases which, when at least one of the above-described methods for determining identity is used, exhibit an identity of at least 50%, preferably of at least 60%, particularly preferably of at least 70%, more preferably of at least 80%, and in particular of at least 90%, with the sequence depicted in SEQ ID NO 3, with the identity having been determined by means of at least one of the above-described methods.

Within the context of the present invention, the term "branching enzyme" or "BE protein" (α-1,4-glucan: α-1,4-glucan 6-glycosyl transferase, E.C. 2.4.1.18) is understood as meaning a protein which catalyzes a transglycosylation reaction in which α-1,4 linkages in an α-1,4-glucan donor are hydrolyzed and the α-1,4-glucan chains which are released in this connection are transferred to an α-1-4-glucan acceptor chain and, in conjunction with this, transformed into α-1,6 linkages.

In connection with the present invention, the term "BEI protein" is intended to be understood as meaning an isoform I branching enzyme (BE); the BEI protein is preferably derived from potato plants.

In this connection, the designation of the isoforms follows the nomenclature proposed by Smith-White and Preiss (Smith-White and Preiss, Plant Mol. Biol. Rep. 12, (1994), 67-71, Larsson et al., Plant Mol. Biol. 37, (1998), 505-511). This nomenclature is based on all enzymes which exhibit a higher homology (identity) at the amino acid level with the corn BEI protein (GenBank Acc. No. D11081; Baba et al., Biochem. Biophys. Res. Commun. 181(1), (1991), 87-94; Kim et al. Gene 216, (1998), 233-243) than with the corn BEII protein (GenBank Acc. No. AF072725, U65948) being designated isoform I branching enzymes or BEI proteins for short.

In connection with the present invention, the term "BEII protein" is intended to be understood as meaning an isoform II branching enzyme (BE); this enzyme is preferably derived from potato plants. In connection with the present invention, all enzymes which exhibit a higher homology (identity) at the amino acid level with the corn BEII protein (GenBank Acc. No. AF072725, U65948) than with the corn BEI protein (GenBank Acc. No. D 11081, AF 072724) should be designated isoform II enzymes or BEII proteins for short.

"Proteins which exhibit the amino acid sequence specified under SEQ ID NO 12 or SEQ ID NO 14" are involved in starch biosynthesis in plants. Amino acid sequences which encode these proteins exhibit an homology with amino acids which encode branching enzyme-like proteins derived from *Arabidopsis thaliana* (EMBL acc No.: BAB02827). It has been found, surprisingly, that plants which exhibit a reduced activity of a protein which exhibits the amino acid sequence specified under SEQ ID NO 12 or SEQ ID NO 14 and exhibit a reduced activity of an SSIII protein, of a BEI protein and of a BEII protein synthesize a starch which has a higher phosphate content, an altered amylopectin side-chain distribution and a higher amylose content as compared with starch which is isolated from potato plants which exhibit a reduced activity of an SSIII protein, of a BEI protein and of a BEII protein. Beside the side-chain distribution, the enzyme brings about a decrease in the side chains having a degree of polymerization DP of less than 11 and a DP of from 11 to 18 and an increase in the proportion of side chains having a degree of polymerization DP of from 62 to 123 and a DP of greater than 123 as compared with starch which is isolated from potato plants which exhibit a reduced activity of an SSIII protein, of a BEI protein and of a BEII protein. It can be concluded from this that proteins which exhibit the amino acid sequence specified under SEQ ID NO 12 or SEQ ID NO 14 are involved in the synthesis of side chains of the starch amylopectin.

The reduction in the activity of one or more SSIII proteins which occur(s) endogenously in the plant or plant cells and of one or more BEI proteins which occur(s) endogenously in the plants or plant cells and of one or more BEII proteins which occur(s) endogenously in the plant or plant cells and of one or more proteins which occur(s) endogenously in the plant or plant cells and exhibit(s) the amino acid sequence specified under SEQ ID NO 12 or SEQ ID NO 14 can be effected by introducing one or more foreign nucleic acid molecules into the plant.

In a further embodiment, the plant cells according to the invention and the plants according to the invention are characterised in that a sense and/or antisense strand of the foreign nucleic acid molecule(s) encode(s) at least a part of a protein having the activity of an SSIII protein and/or BEI protein and/or BEII protein and/or the activity of a protein which exhibits the amino acid sequence specified under SEQ ID NO 12 or SEQ ID NO 14.

In a further embodiment, the invention relates to plant cells according to the invention or plants according to the invention wherein the foreign nucleic acid molecule encoding a BEI protein is chosen from the group consisting of
a) Nucleic acid molecules, which encode a protein with the amino acid sequence specified under SEQ ID NO 5;
b) Nucleic acid molecules, which code a protein, the sequence of which has an identity of at least 60%, in particular of at least 70%, preferably of at least 80% and particularly preferably of at least 90% and especially preferably of at least 95% with the amino acid sequence specified under SEQ ID NO 5;
c) Nucleic acid molecules, which comprise the nucleotide sequence specified under SEQ ID NO 4 or a complimentary sequence thereof;
d) Nucleic acid molecules, which have an identity of at least 70%, preferably of at least 80% and particularly preferably of at least 90% and especially preferably of at least 95% with nucleic acid sequence specified under SEQ ID NO 4;
e) Nucleic acid molecules, which hybridise with at least with one strand of the nucleic acid molecules described under a) or c) under stringent conditions;
f) Nucleic acid molecules, the nucleotide sequence of which deviates from the sequence of the nucleic acid molecules identified under a) or c) due to the degeneration of the genetic code; and
g) Nucleic acid molecules, which represent fragments, allelic variants and/or derivatives of the nucleic acid molecules identified under a), b), c), d), e) or f).

In a further embodiment, the invention relates to plant cells according to the invention or plants according to the invention wherein the foreign nucleic acid molecule encoding a BEII protein is chosen from the group consisting of
a) Nucleic acid molecules, which encode a protein with the amino acid sequence specified under SEQ ID NO 7;
b) Nucleic acid molecules, which code a protein, the sequence of which has an identity of at least 60%, in particular of at least 70%, preferably of at least 80% and particularly preferably of at least 90% and especially preferably of at least 95% with the amino acid sequence specified under SEQ ID NO 7;
c) Nucleic acid molecules, which comprise the nucleotide sequence specified under SEQ ID NO 6 or a complimentary sequence thereof;
d) Nucleic acid molecules, which have an identity of at least 70%, preferably of at least 80% and particularly preferably of at least 90% and especially preferably of at least 95% with nucleic acid sequence specified under SEQ ID NO 6;
e) Nucleic acid molecules, which hybridise with at least with one strand of the nucleic acid molecules described under a) or c) under stringent conditions;
f) Nucleic acid molecules, the nucleotide sequence of which deviates from the sequence of the nucleic acid molecules identified under a) or c) due to the degeneration of the genetic code; and
j) Nucleic acid molecules, which represent fragments, allelic variants and/or derivatives of the nucleic acid molecules identified under a), b), c), d), e) or f).

In a further embodiment, the invention relates to plant cells according to the invention or plants according to the invention wherein the foreign nucleic acid molecule encoding a SSIII protein is chosen from the group consisting of
a) Nucleic acid molecules, which encode a protein with the amino acid sequence specified under SEQ ID NO 2;
b) Nucleic acid molecules, which code a protein, the sequence of which has an identity of at least 60%, in particular of at least 70%, preferably of at least 80% and particularly preferably of at least 90% and especially preferably of at least 95% with the amino acid sequence specified under SEQ ID NO 2;
c) Nucleic acid molecules, which comprise the nucleotide sequence specified under SEQ ID NO 1 or a complimentary sequence thereof;
d) Nucleic acid molecules, which have an identity of at least 70%, preferably of at least 80% and particularly preferably of at least 90% and especially preferably of at least 95% with nucleic acid sequence specified under SEQ ID NO 1
e) Nucleic acid molecules, which hybridise with at least with one strand of the nucleic acid molecules described under a) or c) under stringent conditions;

f) Nucleic acid molecules, the nucleotide sequence of which deviates from the sequence of the nucleic acid molecules identified under a) or c) due to the degeneration of the genetic code; and
j) Nucleic acid molecules, which represent fragments, allelic variants and/or derivatives of the nucleic acid molecules identified under a), b), c), d), e) or f).

In a further embodiment, the invention relates to plant cells according to the invention or plants according to the invention wherein the foreign nucleic acid molecule leading to a reduction in the activity of a protein which exhibits the amino acid sequence specified under SEQ ID NO 12 or SEQ ID NO 14 is chosen from the group consisting of a) Nucleic acid molecules, which code a protein, the sequence of which has an identity of at least 60%, in particular of at least 70%, preferably of at least 80% and particularly preferably of at least 90% and especially preferably of at least 95% with the amino acid sequence specified under SEQ ID NO 12 or 14;
b) Nucleic acid molecules, which comprise the nucleotide sequence specified under SEQ ID NO 11 or 13 or a complimentary sequence thereof;
c) Nucleic acid molecules, which have an identity of at least 70%, preferably of at least 80% and particularly preferably of at least 90% and especially preferably of at least 95% with nucleic acid sequence specified under SEQ ID NO 11 or 13;
d) Nucleic acid molecules, which hybridise with at least with one strand of the nucleic acid molecules as specified in SEQ ID NO 11 or SEQ ID NO 13 under stringent conditions;
e) Nucleic acid molecules, the nucleotide sequence of which deviates from the sequence of the nucleic acid molecules as specified in SEQ ID NO 11 or SEQ ID NO 13 due to the degeneration of the genetic code; and
f) Nucleic acid molecules, which represent fragments, allelic variants and/or derivatives of the nucleic acid molecules identified under a), b), c), d), e) or f).

In connection with the present invention, the term "foreign nucleic acid molecule" or "foreign nucleic acid molecules" is understood as meaning a molecule which is such that it either does not occur naturally in corresponding plants or plant cells or that it does not occur naturally in the plants in the specific spatial arrangement or that it is located at a site in the genome of the plants at which it does not naturally occur. Preference is given to the foreign nucleic acid molecule being a recombinant molecule which is composed of different elements whose combination or specific spatial arrangement does not occur naturally in plant cells.

The foreign nucleic acid molecule(s) which is/are used for the genetic modification can be one assembled nucleic acid molecule or several separate nucleic acid molecules, in particular what are termed single, double, triple or quadruple constructs. Thus, the foreign nucleic acid molecule can, for example, be what is termed a "quadruple construct", which is understood as being a single vector for plant transformation which contains the genetic information for inhibiting the expression of one or more endogenous SSIII proteins and for inhibiting the expression of one or more BEI proteins and for inhibiting the expression of one or more BEII proteins and for inhibiting the expression of one or more proteins which exhibit(s) the amino acid sequence specified under SEQ ID NO 12 or SEQ ID NO 14 or its presence leads to a reduction in the activity of one or more SSIII proteins, BEI proteins or BEII proteins and of proteins which exhibit the amino acid sequence specified under SEQ ID NO 12 or SEQ ID NO 14.

In another embodiment of the invention, several different foreign nucleic acid molecules, rather than a quadruple construct, are introduced into the genome of the plant, with one of these foreign nucleic acid molecules being, for example, a DNA molecule which constitutes, for example, a cosuppression construct which reduces the expression of one or more endogenous SSIII proteins and another foreign nucleic acid molecule being a DNA molecule which, for example, encodes an antisense RNA which reduces the expression of one or more endogenous BEI and/or BEII proteins. However, the use of any combination of antisense, cosuppression, ribozyme and double-stranded RNA constructs or in-vivo mutagenesis which leads to simultaneous reduction in the expression of one or more SSIII proteins, BEI proteins, BEII proteins and proteins which exhibit the amino acid sequence specified under SEQ ID NO 12 or SEQ ID NO 14 is also in principle suitable when constructing foreign nucleic acid molecules.

In this connection, the foreign nucleic acid molecules can either be introduced into the genome of the plant cell simultaneously ("cotransformation") or else one after the other, i.e. in a chronologically consecutive manner ("supertransformation").

The foreign nucleic acid molecules can also be introduced into different individual plants of a species. In this connection, it is possible to generate plants in which the activity of one target protein, or two or three target proteins, is reduced. Subsequent crossing can then be used to generate plants in which the activity of all four target proteins is reduced.

It is furthermore possible to make use of a mutant, instead of a wild-type plant cell or wild-type plant, for introducing a foreign nucleic acid molecule or for generating the plant cells or plants according to the invention, with the mutant being characterized by already exhibiting a reduced activity in the case of one or more target proteins. The mutants can either be spontaneously arising mutants or else mutants which have been generated by the selective use of mutagens.

Various methods which are known to the skilled person, for example those which lead to an inhibition of the expression of endogenous genes which encode an SSIII protein, BEI protein or BEII protein and/or a protein which exhibits the amino acid sequence specified under SEQ ID NO 12 or SEQ ID NO 14, can be used to produce plants which synthesize a starch according to the invention. These methods include, for example, the expression of an appropriate antisense RNA or of a double-stranded RNA construct, the provision of molecules or vectors which mediate a cosuppression effect, the expression of an appropriately constructed ribozyme which specifically cleaves transcripts which encode an SSIII protein, BEI protein, BEII protein or a protein which exhibits the amino acid sequence specified under SEQ ID NO 12 or SEQ ID NO 14, or else what is termed "in-vivo mutagenesis". Furthermore, the simultaneous expression of sense and antisense RNA molecules of the particular target gene to be repressed can also be used to reduce the activity of SSIII proteins and/or the BEI proteins and/or the BEII proteins and/or proteins which exhibit the amino acid sequence specified under SEQ ID NO 12 or SEQ ID NO 14 in the plants. These methods are familiar to the skilled person.

In addition to this, it is known that, in planta, the formation of double-stranded promoter sequence RNA molecules can lead in trans to methylation and transcriptional inactivation of homologous copies of this promoter (Mette et al., EMBO J. 19, (2000), 5194-5201).

All these methods are based on introducing a foreign nucleic acid molecule, or several foreign nucleic acid molecules, into the plant cell genome.

In order to use antisense or cosuppression technology to inhibit gene expression, it is possible, for example, to use a DNA molecule which comprises the entire sequence encoding an SSIII protein and/or BEI protein or BEII protein and/or a protein which exhibits the amino acid sequence specified under SEQ ID NO 12 or SEQ ID NO 14, including any flanking sequences which may possibly be present, or else DNA molecules which only comprise parts of the coding sequence, with these parts having to be long enough to bring about an antisense effect or cosuppression effect in the cells. In general, sequences having a minimum length of 23 bp, preferably a length of 100-500 bp, in particular sequences having a length of more than 500 bp, are suitable for effecting efficient antisense or cosuppression inhibition.

The use of DNA sequences which have a high degree of homology with the sequences which occur endogenously in the plant cell and which encode SSIII proteins, BEI proteins, BEII proteins or proteins which exhibit the amino acid sequence specified under SEQ ID NO 12 or SEQ ID NO 14 is also suitable for antisense or cosuppression approaches. The minimum identity should be greater than approx. 65%. The use of sequences having homologies of at least 90%, in particular of between 95% and 100%, is to be preferred.

It is furthermore possible to conceive of using introns, i.e. noncoding regions of genes which encode SSIII proteins, BEI proteins, BEII proteins and/or proteins which exhibit the amino acid sequence specified under SEQ ID NO 12 or SEQ ID NO 14 for the purpose of achieving an antisense effect or a cosuppression effect.

The use of intron sequences for inhibiting the expression of genes which encode starch biosynthesis proteins has been described in the international patent applications WO 97/04112, WO 97/04113, WO 98/37213 and WO 98/37214.

The skilled person knows how to achieve an antisense effect and a cosuppression effect. The method of cosuppression inhibiting has been described, for example, in Jorgensen (Trends Biotechnol. 8 (1990), 340-344), Niebel et al. (Curr. Top Microbiol. Immunol. 197 (1995), 91-103), Flavell et al., (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), and de Borne et al. (Mol. Gen. Genet. 243 (1994), 613-621).

Expressing ribozymes for the purpose of reducing the activity of particular enzymes in cells is also known to the skilled person and is described, for example, in EP-B1 0321201. Feyter et al. (Mol. Gen. Genet. 250, (1996), 329-338) have, for example, described expressing ribozymes in plant cells.

Furthermore, a reduction in the activity of SSIII proteins and/or the BEI proteins and/or the BEII proteins and/or proteins which exhibit the amino acid sequence specified under SEQ ID NO 12 or SEQ ID NO 14 in plants or plant cells can also be achieved by means of in-vivo mutagenesis, in which a hybrid RNA-DNA oligonucleotide ("chimeroplast") is introduced into the cells by means of transformation of cells (Kipp, P. B. et al., Poster Session at the "5th International Congress of plant molecular biology, 21-27 Sep. 1997, Singapore; R. A. Dixon and C. J. Arntzen, meeting report relating to "Metabolic Engineering in Transgenic Plants", Keystone Symposia, Copper Mountain, Colo., USA, TIBTECH 15, (1997), 441-447; international patent application WO 9515972; Kren et al., Hepatology 25, (1997), 1462-1468; Cole-Strauss et al., Science 273, (1996), 1386-1389; and Beetham et al., 1999, PNAS 96, 8774-8778).

While a part of the DNA component of the RNA-DNA oligonucleotide is homologous with a nucleic acid sequence which encodes an endogenous SSIII protein, BEI protein or BEII protein and/or a protein which exhibits the amino acid sequence specified under SEQ ID NO 12 or SEQ ID NO 14, it possesses a mutation, as compared with the nucleic acid sequence encoding endogenous SSIII proteins, BEI proteins or BEII proteins and/or proteins which exhibit the amino acid sequence specified under SEQ ID NO 12 or SEQ ID NO 14, or contains a heterologous region which is surrounded by the homologous regions.

The mutation or heterologous region which is contained in the DNA component of the RNA-DNA oligonucleotide can be transferred into the genome of a plant cell by the base pairing of the homologous regions of the RNA-DNA oligonucleotide and of the endogenous nucleic acid molecule, followed by homologous recombination. This leads to a reduction in the activity of one or more SSIII proteins, BEI proteins or BEII proteins and/or proteins which exhibit the amino acid sequence specified under SEQ ID NO 12 or SEQ ID NO 14.

Furthermore, the reduction in the activity of an SSIII protein and/or of the BEI protein or the BEII protein and/or in the activity of a protein which exhibits the amino acid sequence specified under SEQ ID NO 12 or SEQ ID NO 14 in the plants can also be brought about by simultaneously expressing sense and antisense RNA molecules of the particular target gene to be repressed.

This can be achieved, for example, by using chimeric constructs which contain inverted repeats of the particular target gene or parts of the target gene (RNAi technology). In this case, the chimeric constructs encode sense and antisense RNA molecules of the particular target gene. In planta, sense and antisense RNA are synthesized simultaneously as one RNA molecule, with sense and antisense RNA being separated from each other by a spacer and being able to form a double-stranded RNA molecule. It has been shown that introducing inverted repeat DNA constructs into the plant genome is a very efficient method for repressing the genes which correspond to the inverted repeat DNA constructs (Waterhouse et al., Proc. Natl. Acad. Sci. USA 95, (1998), 13959-13964; Wang and Waterhouse, Plant Mol. Biol. 43, (2000), 67-82; Singh et al., Biochemical Society Transactions vol. 28 part 6 (2000); 925-927; Liu et al., Biochemical Society Transactions vol. 28 part 6 (2000), 927-929); Smith et al., (Nature 407, (2000), 319-320; International patent application WO 99/53050 A1). Sense and antisense sequences of the target gene or the target genes can also be expressed separately from each other using the same or different promoters (Nap. J-P et al., 6th International Congress of Plant Molecular Biology, Quebec, 18-24 June, 2000; Poster S7-S27, lecture session S7).

It is consequently also possible to reduce the activity of an SSIII protein and/or BEI protein and/or BEII protein and/or reduce the activity of a protein which exhibits the amino acid sequence specified under SEQ ID NO 12 or SEQ ID NO 14 in the plants or plant cells by generating double-stranded RNA molecules which contain inverted repeats of nucleic acid sequences which encode SSIII proteins and/or BEI proteins and/or BEII proteins and/or proteins which exhibit the amino acid sequence specified under SEQ ID NO 12 or SEQ ID NO 14. Preference is given, for this purpose, to introducing inverted repeats of DNA molecules which encode SSIII proteins and/or BEI proteins or BEII proteins and/or proteins which exhibit the amino acid sequence specified under SEQ ID NO 12 or SEQ ID NO 14 into the plant genome, with the DNA molecules to be transcribed being under the control of a promoter which initiates transcription of said DNA molecules in plant cells.

In addition to this, it is known that forming double-stranded RNA molecules of promoter DNA molecules in plants can lead, in trans, to methylation and transcriptional inactivation, of homologous copies of these promoters, which will be designated target promoters in that which follows (Mette et al., EMBO J. 19, (2000), 5194-5201).

It is consequently possible, by inactivating the target promoter, to reduce the expression of a particular protein (e.g. SSIII protein, BEI protein, BEII protein and/or protein which inhibits the amino acid sequence specified under SEQ ID NO 12 or SEQ ID NO 14) which is naturally controlled by this target promoter.

That is, the DNA molecules which comprise the target promoters of the genes (target genes) to be repressed are, in this case, in contrast to the original function of promoters in plants, not being used as elements for controlling the expression of genes or cDNAs but, instead, are being themselves used as transcribable DNA molecules.

Preference is given to using constructs which contain inverted repeats of the target promoter DNA molecules, with the target promoter DNA molecules being under the control of a promoter which controls the genetic expression of said target promoter DNA molecules, for producing the double-stranded target promoter RNA molecules in planta, where these molecules can be present as RNA hairpin molecules. These constructs are subsequently introduced into the plant genome. Expression of the inverted repeats of said target promoter DNA molecules leads in planta to the formation of double-stranded target promoter RNA molecules (Mette et al., EMBO J. 19, (2000), 5194-5201). The target promoter can thereby be inactivated.

The skilled person furthermore knows that he can achieve a reduction of activity of one or more SSIII proteins, BEI proteins or BEII proteins and/or of one or more proteins which exhibit(s) the amino acid sequence specified under SEQ ID NO 12 or SEQ ID NO 14 by expressing nonfunctional derivatives, in particular transdominant mutants, of these proteins and/or by expressing antagonists/inhibitors of these proteins.

Antagonists/inhibitors of these proteins include, for example, antibodies, antibody fragments or molecules having similar binding properties. For example, a cytoplasmatic scFv antibody has been used to modulate the activity of the phytochrome A protein in recombinantly altered tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272).

Examples of useful promoters for expressing the nucleic acids which reduce the activity of a target gene are the cauliflower mosaic virus 35S RNA promoter and the corn ubiquitin promoter for constitutive expression, the B33 patatin gene promoter (Rocha-Sosa et al., EMBO J. 8 (1989), 23-29), the MCPI promoter of the potato metallocarboypeptidase inhibitor gene (Hungarian patent application HU9801674) and the potato GBSSI promoter (international patent application WO 92/11376) for tuber-specific expression in potatoes.

It is particularly advantageous to express the foreign nucleic acid molecule (the foreign nucleic acid molecules) in the plant organs which store starch. These organs are, in particular, potato plant tubers.

However, it is also possible to use promoters which are only activated at a point in time which is determined by external influences (see, for example, WO 93/07279). Heat-shock protein promoters which allow simple induction are particularly of interest in this connection.

It is furthermore possible for a termination sequence, which is used for correctly terminating the transcription, to be present and for a poly-A tail, to which a function in transcript stabilization is attributed, to be added to the transcript. These elements are described in the literature (cf., for example, Gielen et al., EMBO J. 8 (1989), 23-29) and are exchangeable at will.

The present invention therefore also relates to a plant cell or a plant which is genetically modified, with the genetic modification leading to reduction of a protein having the activity of an SSIII protein and/or BEI protein and/or BEII protein and/or the activity of a protein which exhibits the amino acid sequence specified under SEQ ID NO 12 or SEQ ID NO 14 as compared with those of corresponding wild-type plant cells or wild-type plants, and which contains at least one foreign nucleic acid molecule which is selected from the group consisting of a) polynucleotides which encode at least one antisense RNA which leads to a reduction in the expression of at least one endogenous SSIII protein and/or to a reduction in the expression of at least one endogenous BEI protein and/or to a reduction in the expression of at least one endogenous BEII protein and/or to a reduction in the expression of at least one protein having the amino acid sequence specified under SEQ ID NO 12 or SEQ ID NO 14;

b) polynucleotides which lead, by way of a cosuppression effect, to a reduction in the expression of at least one endogenous SSIII protein and/or to a reduction in the expression of at least one endogenous BEI protein and/or to a reduction in the expression of at least one endogenous BEII protein and/or to a reduction in the expression of at least one protein having the amino acid sequence specified under SEQ ID NO 12 or SEQ ID NO 14;

c) polynucleotides which encode at least one ribozyme which specifically cleaves transcripts of at least one endogenous SSIII gene and/or of at least one BEI gene and/or of at least one BEII gene and/or of at least one gene having the nucleotide sequence specified under SEQ ID NO 11 or SEQ ID NO 13;

d) polynucleotides which are introduced by means of in-vivo mutagenesis and which lead to a mutation or an insertion in at least one endogenous SSIII gene and/or to a mutation or an insertion in at least one endogenous BEI gene and/or to a mutation or an insertion in at least one endogenous BEII gene and/or to a mutation or an insertion in at least one gene having the nucleotide sequence specified under SEQ ID NO 11 or SEQ ID NO 13, with the mutation or insertion leading to a reduction in the expression of one endogenous SSIII protein and/or to a reduction in the expression of at least one endogenous BEI protein and/or to a reduction in the expression of at least one endogenous BEII protein and/or to a reduction in the expression of at least one protein having the amino acid sequence specified under SEQ ID NO 12 or SEQ ID NO 14;

e) polynucleotides which encode at least one antisense RNA and at least one sense RNA, with said antisense RNA and said sense RNA being able to form a double-stranded RNA molecule which leads to a reduction in the expression of at least one endogenous SSIII protein and/or to a reduction in the expression of at least one endogenous BEI protein and/or to a reduction in the expression of at least one endogenous BEII protein and/or to a reduction in the expression of at least one protein having the amino acid sequence specified under SEQ ID NO 12 or SEQ ID NO 14;

f) polynucleotides which contain transposons, with the integration of the transposon sequences leading to a mutation or an insertion in at least one endogenous SSIII gene and/or to a mutation or an insertion in at least one endogenous BEI gene and/or to a mutation or an insertion in at least one endogenous BEII gene, and/or to a mutation or an insertion in at least one gene having the nucleotide sequence specified under SEQ ID NO 11 or SEQ ID NO 13, with the mutation or insertion leading to a reduction in the expression of said gene or to the synthesis of inactive SSIII and/or of inactive BEI and/or of inactive BEII and/or of an inactive protein having the amino acid sequence specified under SEQ ID NO 12 or SEQ ID NO 14; and g) T-DNA molecules which, by insertion in at least one endogenous SSIII gene and/or by insertion in at least one endogenous BEI gene and/or by insertion in at least one endogenous BEII gene and/or by insertion in at least one gene having the nucleotide sequence specified under SEQ ID NO 11 or SEQ ID NO 13, lead to a reduction in the expression of said gene or to the synthesis of inactive SSIII and/or of inactive BEI and/or of inactive BEII and/or of an inactive protein having the amino acid sequence specified under SEQ ID NO 12 or SEQ ID NO 14.

In conjunction with the present invention, the term "SSIII gene" or "BEI gene" or "BEII gene" is to be understood to mean a nucleic acid molecule (cDNA, DNA), which encodes a SSIII protein or a BEI protein or BEII protein, respectively.

A large number of techniques are available for introducing DNA into a host plant cell. These techniques include transforming plant cells with T DNA using *Agrobacterium tumefaciens* or *Agrobacterium rhizogenes* as the transforming agent, fusing protoplasts, injecting, electroporating DNA, using the biolistic approach to introduce the DNA, and other possibilities. The use of *agrobacterium*-mediated transformation of plant cells has been intensively investigated and adequately described in EP 120516; Hoekema, In: The Binary Plant Vector System Offsetdrukkerij Kanters B. V. Alblasserdam (1985), Chapter V; Fraley et al., Crit. Rev. Plant Sci. 4, 1-46 and in An et al. EMBO J. 4, (1985), 277-287. For potato transformation, see, e.g., Rocha-Sosa et al., EMBO J. 8, (1989), 29-33).

Plant cells and plants which have been genetically modified by introducing a foreign nucleic acid molecule can be distinguished from wild-type plant cells or wild-type plants by, inter alia, the fact that they contain a foreign nucleic acid molecule which does not naturally occur in wild-type plant cells or wild-type plants or by the fact that such a molecule is integrated at a site in the genome of the plant cell according to the invention or in the genome of the plant according to the invention at which it does not occur in wild-type plant cells or wild-type plants, that is in another genomic environment. Furthermore, such plant cells according to the invention and plants according to the invention can be distinguished from wild-type plant cells or wild-type plants by the fact that they contain at least one copy of the foreign nucleic acid molecule stably integrated in their genome, where appropriate in addition to copies of such a molecule which occur naturally in the wild-type plant cells or wild-type plants. If the foreign nucleic acid molecule(s) which has/have been introduced into the plant cells according to the invention or plants according to the invention is/are (a) copy(s) which is/are in addition to molecules which already occur naturally in the wild-type plant cells or wild-type plants, the plant cells according to the invention or the plants according to the invention can be distinguished from wild-type plant cells or wild-type plants by the fact, in particular, that this/these additional copy(s) is/are located at sites in the genome at which it/they do not occur in wild-type plant cells or wild-type plants. This can be verified by means of a Southern blot analysis, for example.

In addition, the plant cells according to the invention and the plants according to the invention can preferably be distinguished from wild-type plant cells or wild-type plants by at least one of the following features: if the foreign nucleic acid molecule which has been introduced is heterologous in relation to the plant cell or plant, the plant cells according to the invention or plants according to the invention then exhibit transcripts of the nucleic acid molecules which have been introduced. These transcripts can be detected, for example, by means of Northern blot analysis or by means of RT-PCR (Reverse Transcription Polymerase Chain Reaction). Plant cells according to the invention and plants according to the invention which are expressing an antisense transcript and/or an RNAi transcript can be detected, for example, using specific nucleic acid probes which are complementary to the RNA (which naturally occurs in the plant cell) which encodes the protein.

In connection with the present invention, the term "potato plant" or "potato" means plant species of the genus *Solanum*, particularly tuber-producing species of the genus *Solanum* and, in particular, *Solanum tuberosum*.

The present invention furthermore relates to a method for producing a genetically modified plant according to the invention in which a) a plant cell is genetically modified, with the genetic modification leading to a reduction in the activity of one or more SSIII proteins which occur endogenously in the plant and of one or more BEI proteins which occur endogenously in the plant and of one or more BEII proteins which occur endogenously in the plant and of one or more proteins which occur endogenously in the plant and exhibit at least 80% identity with the amino acid sequence specified under SEQ ID NO 12 or SEQ ID NO 14, as compared with corresponding wild-type plant cells which have not been genetically modified;

b) a plant is regenerated from plant cells derived from step a); and c) where appropriate, further plants are generated using the plants in accordance with step b).

Preferred embodiments of the invention are methods for producing a genetically plant according to the invention wherein said genetically modified plant produces a starch according to the invention.

The genetic modification which is introduced into the plant cell in accordance with step a) can in principle be any type of modification which leads to a reduction in the activity of one or more SSIII proteins which occur endogenously in the plant and of one or more BEI proteins which occur endogenously in the plant and of one or more BEII proteins which occur endogenously in the plant and of one or more proteins which occur endogenously in the plant and which exhibit at least 80% identity with the under SEQ ID NO 12 or SEQ ID NO 14.

Methods known to the skilled person (e.g. described in "Plant Cell Culture Protocols", 1999, edt. by R. D. Hall, Humana Press, ISBN 0-89603-549-2) can be used to regenerate the plants in accordance with step (b).

The generation of further plants in accordance with step (c) of the method according to the invention can be effected, for example, by means of vegetative propagation (for example by way of cuttings or tubers or by way of callus culture and regeneration of whole plants) or by means of sexual propagation. In this connection, the sexual propagation preferably takes place in a controlled manner, i.e. selected plants possessing particular properties are crossed with each other and propagated. In this connection, the selection preferably takes place such that the further plants which are obtained in accordance with step c) exhibit the genetic modification which was introduced in step a).

DESCRIPTION OF THE SEQUENCES

SEQ ID 1: Nucleic acid sequence for a potato (*solanum tuberosum*) SSIII starch synthase, with the sequences which encode the corresponding SSIII protein being indicated.

SEQ ID 2: Amino acid sequence of a potato SSIII protein.

SEQ ID 3: Amino acid sequence of the Pfam cbm25 binding domain of a potato (*solanum tuberosum*) SSIII protein.

SEQ ID 4: Nucleic acid sequence encoding a potato (*solanum tuberosum*) BEI branching enzyme.

SEQ ID 5: Amino acid sequence of a potato (*solanum tuberosum*) BEI branching enzyme.

SEQ ID 6: Nucleic acid sequence encoding a potato (*solanum tuberosum*) BEII branching enzyme.

SEQ ID 7: Amino acid sequence of a potato (*solanum tuberosum*) BEII branching enzyme.

SEQ ID 8: PCR-amplified nucleic acid sequence encoding a potato (*solanum tuberosum*) BEII branching enzyme.

SEQ ID NO 9: Nucleic acid sequence containing the region encoding the 3' region of a *solanum tuberosum* (cv Désirée) protein involved in starch biosynthesis. This sequence is inserted in plasmid AN 46-196.

SEQ ID NO 10: Nucleic acid sequence containing the region encoding the 5' region of a *solanum tuberosum* (cv Désirée) protein involved in starch biosynthesis. This sequence is inserted in plasmid AN 47-196.

SEQ ID NO 11: Nucleic acid sequence containing the complete region encoding a *solanum tuberosum* (cv Désirée) protein involved in starch biosynthesis. This sequence is inserted in plasmid AN 49 and was deposited on 15 Sep. 2003, under the number DSM 15926, in the Deutschen Sammlung von Mikroorganismen und Zellkulturen [German collection of microorganisms and cell cultures] GmbH, Mascheroder Weg 1b, 38124 Braunschweig, Germany, in accordance with the Budapest Treaty.

SEQ ID NO 12: Amino acid sequence encoding a *solanum tuberosum* (cv Désirée) protein involved in starch biosynthesis. This sequence can be deduced from the nucleic acid sequence inserted in plasmid AN 49 or from the nucleic acid sequence which is described under SEQ ID NO 11.

SEQ ID NO 13: Nucleic acid sequence containing the complete region encoding a *solanum tuberosum* (cv Désirée) protein involved in starch biosynthesis. This sequence was obtained by joining the nucleic acid sequences described under SEQ ID NO 9 and SEQ ID NO 10. This nucleic acid sequence is an allelic variant of the nucleic acid sequence which is described under SEQ ID NO 11 and which encodes a protein which is involved in starch biosynthesis.

SEQ ID NO 14: Amino acid sequence encoding a *solanum tuberosum* (cv Désirée) protein involved in starch biosynthesis. This sequence can be deduced from the nucleic acid sequence which is described under SEQ ID NO 13 and is the amino acid sequence of an allelic variant of the amino acid sequence which is described under SEQ ID NO 12 and which encodes a protein which is involved in starch biosynthesis.

GENERAL METHODS

Starch Analysis

Figure 1:
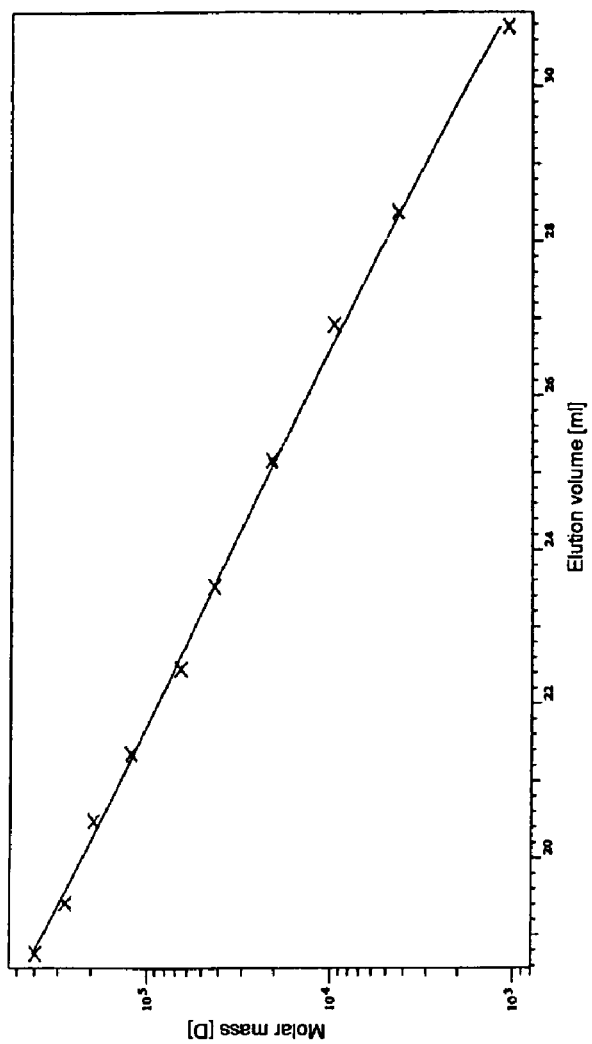
FIG. 1: Calibration curve and table containing appurtenant dextran standards

1. Determining the Amylose Content or the Amylose/Amylopectin Ratio

Starch was isolated from potato plants using standard methods and the amylose content, and the amylose to amylopectin ratio, were determined using the method described by Hovenkamp-Hermelink et al. (Potato Research 31, (1988), 241-246). The amylose content is calculated by applying the formula cited on page 243 of this article.

2. Determining the Phosphate Content

Positions C2, C3 and C6 of the glucose units in the starch can be phosphorylated. In order to determine the C6-P content of the starch, 50 mg of starch are hydrolyzed, at 95° C. for 4 h, in 500 µl of 0.7 M HCl. The assays are then centrifuged at 15500×g for 10 min and the supernatants are taken off. 7 µl from the supernatants are mixed with 193 µl of imidazole buffer (100 mM imidazole, pH 7.4; 5 mM $MgCl_2$, 1 mM EDTA and 0.4 mM NAD). The measurement was carried out at 340 nm in a photometer. After a basal absorption had been established, the enzyme reaction was started by adding 2 units of glucose-6-phosphate dehydrogenase (from *Leuconostoc mesenteroides*, Boehringer Mannheim). The change in absorption is directly proportional to the concentration of the G-6-P content in the starch.

The total phosphate content was determined by the Ames method (Methods in Enzymology VIII, (1966), 115-118).

30 µl of ethanolic magnesium nitrate solution are added to approx. 50 mg of starch and the mixture is incinerated at 500° C. for 3 hours in a muffle furnace. 300 µl of 0.5 M hydrochloric acid are added to the residue and the whole is incubated at 60° C. for 30 min. Subsequently, an aliquot is made up to 300 µl 0.5 M hydrochloric acid and the whole is added to a mixture of 100 µl of 10% ascorbic acid and 600 µl of 0.42% ammonium molybdate in 2 M sulfuric acid and incubated at 45° C. for 20 min.

This is followed by a photometric determination at 820 nm using a phosphate calibration series as standard.

3. Determining the Gel Strength (Texture Analyzer)

1.5 g of starch (TS) are pasted, in 25 ml of aqueous suspension, in an RVA appliance (for the conditions, see general methods, item 4: RVA analytical method 1) and then stored at room temperature for 24 h in a closed vessel. The samples are fixed under the probe (cylindrical piston with planar surface) of a TA-XT2 texture analyzer from Stable Micro Systems (Surrey, UK), and the gel strength is determined using the following parameters:

| | |
|---|---|
| test rate | 0.5 mm/s |
| depth of penetration | 7 mm |
| contact area | 113 $mm^2$ |
| pressure | 2 g |

4. Using a Rapid Visco Analyzer (RVA) to Determine the Viscosity Properties

Standard Method 2 g of starch (TS) are taken out in 25 ml of $H_2O$ (deionized water, conductivity of at least 15 megaohms) and used for analysis in a rapid visco analyzer (Newport Scientific Pty Ltd., Investmet Support Group, Warriewod NSW 2102, Australia). The appliance is operated in accordance with the manufacturers instructions. In this connection, the viscosity values are given in RVUs in accordance with the manufacturers operating instructions, which, in this respect, are hereby incorporated into the description by reference. In order to determine the viscosity of the aqueous solution of the starch, the starch suspension is first of all heated at 50° C. for 1 minute (step 1), after which it is heated from 50° C. to 95° C. at a rate of 12° C. per minute (step 2). The temperature is then maintained at 95° C. for 2.5 min (step 3). After that, the solution is cooled down from 95° C. to 50° C. at a rate of 12° C. per minute (step 4). The viscosity is determined during the entire period.

Only 1.5 g of starch (TS) were taken up in 25 ml of $H_2O$ (deionized water, conductivity of at least 15 megaohms) when, in particular, the limits of the RVA measurement range were insufficient when an initial weight of 2.0 g (TS) of starch were taken up in 25 ml of $H_2O$ (deionized water, conductivity of at least 15 megaohms).

RVA Analytical Method 1:

In order to determine the viscosity of a 6% aqueous solution of the starch, the starch suspension is first of all stirred at 960 rpm for 10 seconds after which it is heated at 50° C. for initially 1 minute and at a stirring speed of 160 rpm (step 1). After that, the temperature is raised from 50° C. to 95° C. at a heating rate of 12° C. per minute (step 2). The temperature is kept at 95° C. for 2.5 minutes (step 3) and, after that, lowered from 95° C. to 50° C. at a rate of 12° C. per minute (step 4). The last step (step 5) maintains the temperature of 50° C. for 2 minutes.

After the program has come to an end, the stirrer is removed and the beaker is covered. The pasted starch is now available for the texture analysis after 24 h.

RVA Analytical Method 2:

In order to determine the viscosity of a 6% aqueous solution of the starch containing 2.7 M calcium chloride, the starch suspension is first of all stirred at 960 rpm and at 30° C. for 10 seconds (step 1). After that, the temperature is raised, at a stirring speed of 160 rpm, from 30° C. to 95° C. at a heating rate of 12° C. per minute (step 2). The temperature is kept at 95° C. for 2 minutes and 30 seconds (step 3) and, after that, lowered from 95° C. to 50° C. at a rate of 12° C. per minute (step 4). The last step (step 5) maintains the temperature of 50° C. for 2 minutes.

After the program has come to an end, the stirrer is removed and the beaker is covered. The pasted starch is now available for the texture analysis after 24 h.

In some cases, an altered temperature profile was also used in order to clearly depict an increase in the pasting temperature.

The following temperature profile was employed:

RVA Analytical Method 3:

In order to determine the viscosity of a 6% aqueous solution of the starch, the starch suspension is first of all stirred at 960 rpm for 10 seconds after which it is heated at 50° C. for initially 2 minutes and at a stirring speed of 160 rpm (step 1). After that, the temperature is raised from 50° C. to 95° C. at a heating rate of 1.5° C. per minute (step 2). The temperature is kept at 95° C. for 15 minutes (step 3) and, after that, lowered from 95° C. to 50° C. at a rate of 1.5° C. per minute (step 4). The last step (step 5) maintains the temperature of 50° C. for 30 minutes.

After the program has come to an end, the stirrer is removed and the beaker is covered. The pasted starch is now available for the texture analysis after 24 h.

In the profile of the RVA analysis, there are characteristic values which are depicted for comparing different measurements and substances. In connection with the present invention, the following terms are to be understood as follows:

Maximum Viscosity (RVA Max)

The maximum viscosity is understood as being the highest viscosity value, as measured in RVUs, which is reached in step 2 or 3 of the temperature profile.

Minimum Viscosity (RVA Min)

The minimum viscosity is understood as being the lowest viscosity value, as measured in RVUs, which occurs in the temperature profile after the maximum viscosity. This normally occurs in step 3 of the temperature profile.

Final Viscosity (RVA Fin)

The final viscosity is understood as being the viscosity value, as measured in RVUs, which occurs at the end of the measurement.

Setback (RVA Set)

What is termed the "setback" is calculated by subtracting the final viscosity value from that of the minimum which occurs in the curve after the maximum viscosity has been reached.

Pasting Temperature

The pasting temperature is understood as being the temperature in the RVA profile at which the viscosity increases strongly within a short period for the first time.

Peak Time (RVA T)

The peak time is understood as being the time in the temperature profile at which the viscosity has reached the maximum value.

5. Process for Extracting the Starch from Potato Tubers

All the tubers belonging to a line (from 4 to 5 kg) are processed jointly in a commercially available juice extractor (Multipress automatic MP80, Braun). The starch-containing juice is collected in a 10 L bucket (height of the bucket/diameter of the bucket ratio=approx. 1.1) into which 200 ml of tap water containing a spoon tip (approx. 3-4 g) of sodium disulfite have been initially introduced. The bucket is then completely filled with tap water. After the starch has settled for a period of 2 hours, the supernatant is decanted off and the starch is resuspended in 10 l of tap water and passed through a sieve having a mesh width of 125 μm. After 2 hours (the starch has once again settled on the bottom of the bucket) the aqueous supernatant is decanted once again. This washing process is repeated a further 3 times such that the starch is in all resuspended five times in fresh tap water. These starches are then dried at 37° C. down to a water content of 12-17% and homogenized in a mortar. The starches are now available for analyses.

6. Using Gel Permeation Chromatography to Analyze the Side-Chain Distribution of the Amylopectin In order to separate amylose and amylopectin, 100 mg of starch are dissolved in 6 ml of 90% (v/v) DMSO while stirring continuously. After 3 volumes of ethanol have been added, the precipitate is separated off by centrifuging for 10 minutes at 1 800 g and at room temperature. The pellet is then washed with 30 ml of ethanol, dried and dissolved, at 60° C., in 10 ml of 1% (w/v) NaCl solution. After the solution has been cooled down to 30° C., approximately 50 mg of thymol are added slowly and this solution is incubated at 30° C. for from 2 to 3 days. After that, the solution is centrifuged for 30 min at 2000 g and at room temperature. 3 volumes of ethanol are added to the supernatant and the amylopectin which precipitates out is separated off by centrifuging for 5 minutes at 2000×g and at room temperature. The pellet (amylopectin) is washed with 10 ml of 70% (v/v) ethanol, centrifuged for 10 min at 2000×g and at room temperature, and dried with acetone.

10 mg of amylopectin are then stirred at 70° C. for 10 minutes in 250 µl of 90% (v/v) DMSO. 375 µl of water are added to the solution at 80° C. so as to achieve complete dissolution.

300 µl of a 16.6 mM sodium acetate solution, pH 3.5, and 2 µl of isoamylase (0.24 u/µl, Megazyme, Sydney, Australia) are added to 200 µl of this solution and the whole is incubated at 37° C. for 15 hours.

A 1:4 dilution of this aqueous isoamylase reaction mixture with DMSO containing 90 mM Na nitrate is then filtered using an 0.2 µm filter after which 24 µl of the filtrate is analyzed chromatographically. The separation is carried out using two columns which are connected in series, i.e. first of all a Gram PSS3000 (Polymer Standards Service, together with appropriate precolumn), with this then being followed by a Gram PSS100. The detection was effected using a refraction index detector (RI 71, Shodex). The column was equilibrated with DMSO containing 90 mM sodium nitrate. It was eluted with DMSO containing 90 mM sodium nitrate at a flow rate of 0.7 ml/min and over a period of 1 hour.

In order to correlate the elution volume with the molar mass and thus with the chain length of the side chains, the column which was used was calibrated with dextran standards. The dextrans which were used, their pertinent molar masses, and the elution volumes, are given in FIG. 1. Version 6 of the Wingpc program from Polymer Standards Service GmbH, Mainz, Germany was used for the further evaluation of the chromatograms which were obtained.

The total area below the line of the GPC chromatogram was divided into individual sections which in each case represent side-chain groups of differing length. The sections which were chosen contained glucan chains having the following degrees of polymerization (DP=number of glucose monomers within a side chain): DP less than 11, DP11-18, DP19-24, DP25-30, DP31-36, DP37-42, DP43-48, DP49-55, DP56-61, DP62-123 and DP greater than 123). For the purpose of determining the molecular weights of the individual side chains, glucose was assumed to have a molecular weight of 162. The total area below the line in the GPC chromatogram was stipulated to be 100% and the proportion of the areas of the individual sections was calculated based on the proportion of the total area.

EXAMPLES

1. Preparing the Expression Vector ME5/6 pGSV71 is a derivative of the plasmid pGSV7, which is derived from the intermediary vector pGSV1. pGSV1 is a derivative of pGSC1700, whose construction was described by Cornelissen and Vanderwiele (Nucleic Acid Research 17, (1989), 19-25). pGSV1 was obtained from pGSC1700 by deleting the carbenicillin resistance gene and deleting the T-DNA sequences of the TL-DNA region of the plasmid pTiB6S3.

pGSV7 contains the origin of replication of the plasmid pBR322 (Bolivar et al., Gene 2, (1977), 95-113) and also the origin of replication of the *pseudomonas* plasmid pVS1 (Itoh et al., Plasmid 11, (1984), 206). pGSV7 also contains the selectable marker gene aadA from the *Klebsiella pneumoniae* transposon Tn1331, which mediates resistance to the antibiotics spectinomycin and streptomycin (Tolmasky, Plasmid 24 (3), (1990), 218-226; Tolmasky and Crosa, Plasmid 29(1), (1993), 31-40). Plasmid pGSV71 was obtained by cloning a chimeric bar gene between the border regions of pGSV7. The chimeric bar gene contains the cauliflower mosaic virus promoter sequence for initiating transcription (Odell et al., Nature 313, (1985), 180), the *streptomyces hygroscopicus* bar gene (Thompson et al., Embo J. 6, (1987), 2519-2523) and the 3'-untranslated region of the nopaline synthase gene of the pTiT37 T-DNA for transcription termination and polyadenylation. The bar gene mediates tolerance to the herbicide glufosinate ammonium.

At position 198-222, the T-DNA contains the right-hand border sequence of the TL-DNA from the plasmid pTiB6S3 (Gielen et al., EMBO J. 3, (1984), 835-846). A polylinker sequence is located between nucleotides 223-249. Nucleotides 250-1634 contain the P35S3 promoter region of the cauliflower mosaic virus (Odell et al., see above). The coding sequence of the *streptomyces hygroscopicus* phosphinothricin resistance gene (bar) (Thompson et al., 1987, see above) is located between nucleotides 1635-2186. In this connection, the two terminal codons at the 5' end of the bar wild-type gene were replaced with the codons ATG and GAC. A polylinker sequence is located between nucleotides 2187-2205. The 260 bp TaqI fragment of the untranslated 3' end of the nopaline synthase gene (3'nos) from the T-DNA of plasmid pTiT37 (Depicker et al., J. Mol. Appl. Genet. 1, (1982), 561-573) is located between nucleotides 2206 and 2465. Nucleotides 2466-2519 contain a polylinker sequence. The left-hand border sequence of the pTiB6S3 TL-DNA (Gielen et al., EMBO J. 3, (1984), 835-846) is located between nucleotides 2520-2544.

The vector pGSV71 was then cut with the enzyme PstI and blunted. The B33 promoter and the ocs cassette were excised, as an EcoRI-HindIII fragment, from the vector pB33-Kan and blunted and inserted into the PstI-cut and blunted vector pGSV71. The resulting vector served as the starting vector for constructing ME5/6: an oligonucleotide containing the cleavage sites EcoRI, PacI, SpeI, SrfI, SpeI, NotI, PacI and EcoRI was introduced, with the PstI cleavage site being duplicated, into the PstI cleavage site in vector ME4/6 which was located between the B33 promoter and the ocs element. The resulting expression vector was designated ME5/6.

Description of the Vector pSK-Pac:

pSK-Pac is a derivative of the pSK-Bluescript (Stratagene, USA) in which a flanking PacI cleavage site has been introduced at each end of the multiple cloning site (MCS).

2. Producing Transgenic Potato Plants in which the Activities of a BEI Protein, of an SSIII Protein and of a BEII Protein are Reduced In order to generate transgenic plants in which the activities of a BEI protein, of an SSIII protein and of a BEII protein are reduced, transgenic plants in which the activities of a BEI protein and of an SSIII protein were reduced were first of all generated. For this purpose, agrobacteria were used, as described in Rocha-Sosa et al. (EMBO J. 8, (1989), 23-29), to transfer the T-DNA of the plasmid pB33-alpha-BEI-alpha-SSIII-Kan into potato plants.

In order to construct the plasmid pB33-alpha-BEI-alpha-SSIII-Kan, the expression vector pBin33-Kan was first of all constructed. For this, the promoter of the *solanum tuberosum* patatin gene B33 (Rocha-Sosa et al., 1989, see above) was ligated, as a DraI fragment (nucleotides-1512-+14), into the vector pUC19 (Genbank Acc. No. M77789), which had been cut with SstI and whose ends had been blunted using T4 DNA polymerase. This resulted in the plasmid pUC19-B33. The B33 promoter was excised from this plasmid using EcoRI and SmaI and ligated into the vector pBinAR, which had been cut correspondingly. This resulted in the plant expression vector pBin33-Kan. The plasmid pBinAR is a derivative of the vector plasmid pBin19 (Bevan, Nucl. Acid Research 12, (1984), 8711-8721) and was constructed by Höfgen and Willmitzer (Plant Sci. 66, (1990), 221-230). A HindII fragment of 1631 bp in length, which contains a partial cDNA encoding the potato BEI enzyme (Kossmann et al., 1991, Mol. & Gen. Genetics 230(1-2):39-44), was then blunted and introduced into vector pBinB33, which had been previously cut with SmaI, in the antisense orientation in regard to the B33 promoter (promoter of the *solanum tuberosum* patatin gene B33; Rocha-Sosa et al., 1989). The resulting plasmid was cut with BamHI. A BamHI fragment of 1363 bp in length, containing a partial cDNA encoding the potato SSIII protein (Abel et al., 1996, loc. cit.), was introduced into the cleavage site, likewise in the antisense orientation with regard to the B33 promoter.

Following the transformation, it was possible to identify different lines of transgenic potato plants in whose tubers the activities of a BEI protein and of an SSIII protein were clearly reduced. The plants resulting from this transformation were designated by 038VL.

In order to detect the activity of soluble starch synthases by means of nondenaturing gel electrophoresis, tissue samples of potato tubers were disrupted in 50 mM Tris-HCl, pH 7.6, 2 mM DTT, 2.5 mM EDTA, 10% glycerol and 0.4 mM PMSF. The electrophoresis was carried out in a MiniProtean II chamber (BioRAD). The monomer concentration of the gels, which were 1.5 mm thick, was 7.5% (w/v), while 25 mM Tris-glycine, pH 8.4, served as the gel buffer and running buffer. Equal quantities of protein extract were loaded on and fractionated for 2 h at 10 mA per gel. The activity gels were then incubated in 50 mM Tricine-NaOH, pH 8.5, 25 mM potassium acetate, 2 mM EDTA, 2 mM DTT, 1 mM ADP-glucose, 0.1% (w/v) amylopectin and 0.5 M sodium citrate. Glucans which were formed were stained with Lugol's solution.

BEI activity was likewise detected using nondenaturing gel electrophoresis: in order to isolate proteins from plants, the sample material was triturated in liquid nitrogen, taken up in extraction buffer (50 mM Na citrate, pH 6.5; 1 mM EDTA, 4 mM DTT) and, after centrifugation (10 min, 14 000 g, 4° C.), used directly for measuring the protein concentration as described by Bradford. From 5 to 20 μg, as required, of total protein extract were then treated with 4-fold loading buffer (20% glycerol, 125 mM Tris HCl, pH 6.8) and loaded onto a "BE activity gel". The composition of the running buffer (RB) was as follows: RB=30.2 g of Tris base, pH 8.0, 144 g of glycine made up to 1 l with $H_2O$.

After the gel run had come to an end, the gels were in each case incubated overnight at 37° C. in 25 ml of "phosphorylase buffer" (25 ml of 1 M Na citrate, pH 7.0, 0.47 g of glucose-1-phosphate, 12.5 mg of AMP, 2.5 mg of rabbit phosphorylase a/b). The gels were stained with Lugol's solution.

Further analyses showed that starches isolated from the lines 038VL008 and 038VL107, in which both the BEI protein and the SSIII protein were reduced, exhibited the highest phosphate content of all the independent transformants which were examined.

Plants of these lines were then transformed with the plasmid pGSV71-alpha-BEII-basta as described in Rocha-Sosa et al, (EMBO J. 8, (1989), 23-29). Plasmid pGSV71-alpha-BEII-basta was constructed by using standard methods to screen a tuber-specific potato cDNA library with a DNA fragment which was amplified by means of RT-PCR (primers: 5'-ggggtgttggcttgacta (SEQ ID NO. 15) and 5'-cccttctcctc-ctaatccca (SEQ ID NO. 16); stratagene ProSTAR™ HF single-tube RT-PCR system) using tuber total RNA as template. This resulted in the isolation of a DNA fragment of about 1 250 bp in size (SEQ ID NO. 8), which was then subcloned, as an EcoRV-SmaI fragment, into the EcoRV cleavage site of the cloning vector pSK-Pac (see above) and finally ligated, as a PacI fragment, into the expression vector ME5/6 in the antisense orientation with regard to the promoter. This gave rise to the plasmid pGSV71-alpha-BEH-basta (see FIG. 6).

Tuber tissue samples were taken from the independent transformant plants which were obtained by transformation with plasmid pGSV71-alpha-BEII-basta, and which were designated 108CF and, respectively, 110CF, and the amylose content of the samples was determined (see methods). The starches of the independent lines whose tubers exhibited the highest amylose content were used for further analysis of the starch properties. In order to demonstrate that, in addition to exhibiting reduced activity of a BEI protein and of an SSIII protein, these plants also exhibited reduced activity of a BEII protein, an analysis was also carried out using nondenaturing gel electrophoresis. The analysis was carried out using the same method as that already described above for analyzing the reduced BEI activity except that the nondenaturing polyacrylamide gel contains 0.5% maltodextrin (Beba, 15% maltodextrin solution for neonates, Nestle) in addition to the above-described composition. Adding the dextrin made it possible to display the different activities of the BEI proteins and BEII proteins in a gel after incubating the gels in "phosphorylase buffer" (25 ml of 1 M Na citrate, pH 7.0, 0.47 g of glucose-1-phosphate, 12.5 mg of AMP, 2.5 mg of rabbit phosphorylase a/b) at 37° C. overnight and then staining with Lugol's solution.

3. Cloning a Full-Length Sequence of a *Solanum Tuberosum* Protein Having the Sequence Specified Under SEQ ID NO 12 or SEQ ID NO 14

The gene sequence encoding a *solanum tuberosum* protein having the sequence specified under SEQ ID NO 12 or SEQ ID NO 14 has not previously been described.

By making sequence comparisons using different branching enzymes, it was possible to identify a domain which was used to screen EST databases. The potato EST TC73137 (TIGR database) was identified in this connection.

The primers B1_Asp (GAT GGG TAC CAG CAC TTC TAC TTG GCA GAG G) (SEQ ID NO. 17) and B2_Sal (TCA AGT CGA CCA CAA CCA GTC CAT TTC TGG) (SEO ID NO. 18) were used to amplify a sequence, which corresponded to this EST sequence, from a tuber-specific *solanum tuberosum* (cv Désirée) cDNA library. Attempts to use leaf-specific, sink or source tissue-specific cDNA libraries as templates for the PCR reaction did not give rise to any amplificate. Primers which were complementary to the ends of the previously known sequence and vector sequences of the relevant cDNA libraries were prepared for the purpose of amplifying the entire sequence encoding the protein concerned, which sequence also comprised previously unknown sequences. None of the primer combinations for amplifying a full-length sequence which were used when taking this approach led to any further region being amplified. Tomato EST databases were consequently screened once again.

In this connection, it was possible to identify two tomato ESTs (TIGR database; BG127920 and TC130382) which either exhibited a high degree of homology with the above-described amplificate of the potato protein (TC130382) or (BG127920) or with a putative branching enzyme derived from *Arabidopsis* (Genbank: GP9294564dbjBAB02827.1).

Primers were now prepared once again in order to also amplify previously unknown sequences of the protein having the amino acid sequence depicted under SEQ ID NO 12 or SEQ ID NO 14. The 3' region of the protein concerned was amplified by means of PCR, using the primers KM2_Spe (5'-TCAAACTAGTCACAACCAGTCCATTTCTGG-3') (SEQ ID NO. 19) and SoputE (5'-CACTTTAGAAGGTAT-CAGAGC-3') (SEQ ID NO. 20), from a cDNA library which was prepared from *solanum tuberosum* (cv Désirée) tubers. The resulting fragment, of approx. 1 kb in size, was cloned in an undirected manner into the pCR4-TOPO vector supplied by Invitrogen (product number: 45-0030). The resulting plasmid was designated AN 46-196. The sequence of the fragment inserted in plasmid AN 46-196 is depicted under SEQ ID NO 9.

The 5' region was likewise amplified by means of the PCR technique from the same cDNA library using the primers So_put5' (5-GTATTTCTGCGAAGGAACGACC-3') (SEQ ID NO. 21) and So_putA (5'-AACAATGCTCTCTCT-GTCGG-3') (SEQ ID NO. 22). The resulting fragment, of approx. 2 kb in size, was cloned in an undirected manner into the pCR4-TOPO invitrogen vector (product number: 45-0030). The resulting plasmid was designated AN 47-196. The sequence of the fragment inserted in plasmid AN 47-196 is depicted under SEQ ID NO 10. Primers were now prepared once again in order to amplify a full-length sequence.

The following primers were used: SOputA (AACAAT-GCTCTCTCTGTCGG) (SEQ ID NO. 22) and SO_putE (CACTTTAGAAGGTATCAGAGC) (SEQ ID NO. 20). A PCR product of approximately 3.2 kb in size was obtained and cloned into the Invitrogen vector pCR2.1 (product number: 45-0030). The resulting plasmid (deposited under DSM 15926) was designated AN 49. The sequence of the fragment inserted in plasmid AN 49 is depicted under SEQ ID NO 11.

4. Producing Transgenic Potato Plants in which the Activities of a BEI Protein, of an SSIII Protein, of a BEII Protein and of a Protein Having the Amino Acid Sequence Depicted Under SEQ ID NO 12 or SEQ ID NO 14 are Reduced a) Information Concerning Vector pBinB33-Hyg The EcoRI-HindIII fragment comprising the B33 promoter, a part of the polylinker and the ocs terminator, was excised from plasmid pBinB33 and ligated into the vector pBIB-Hyg (Becker, 1990), which had been cut correspondingly.

The plasmid pBinB33 was obtained by ligating the promoter of the *solanum tuberosum* patatin gene B33 (Rocha-Sosa et al., 1989), as a DraI fragment (nucleotides-1512-+14), into the SstI-cut vector pUC19, whose ends had been blunted using T4 DNA polymerase. This resulted in the plasmid pUC19-B33. The B33 promoter was excised from this plasmid using EcoRI and SmaI and ligated into vector pBinAR, which had been cut correspondingly. This resulted in the plant expression vector pBinB33.

The plasmid pBinAR is a derivative of the vector plasmid pBin19 (Bevan, 1984) and was constructed as follows:

A fragment of 529 bp in length, which comprises nucleotides 6909-7437 of the cauliflower mosaic virus 35S RNA promoter (Pietrzak et al., 1986, Nucleic Acids Research 14, 5857-5868), was isolated, as an EcoRI/KpnI fragment, from the plasmid pDH51 (Pietrzak et al., 1986) and ligated between the EcoRI and KpnI cleavage sites of the pUC18 polylinker. This resulted in the plasmid pUC18-35S.

A fragment of 192 bp in length, which comprises the polyadenylation signal (3' end) of the octopin synthase gene (gene 3) of the T-DNA of the Ti-plasmid pTiACH5 (Gielen et al., 1984) (nucleotides 11749-11939), was isolated from the plasmid pAGV40 (Herrera-Estrella et al., 1983) using the restriction endonucleases HindIII and PvuII. After SspI linkers had been added to the PvuII cleavage site, the fragment was ligated between the SphI and HindIII cleavage sites of pUC18-35S. This resulted in the plasmid pA7.

The entire polylinker, containing the 35S promoter and the ocs terminator, was excised from pA7 using EcoRI and HindIII and ligated into pBin19, which had been cut correspondingly. This resulted in the plant expression vector pBinAR (Höfgen and Willmitzer, 1990).

b) Information Concerning Vector AN 54-196

AN 54-196 is a derivative of plasmid pBinB33-Hyg, into which a constituent sequence of the nucleic acid sequence encoding the protein having the amino acid sequence specified under SEQ ID NO 12 or SEQ ID NO 14 was inserted as an inverted repeat (RNAi technology) under the control of the promoter of the *solanum tuberosum* patatin gene B33 (Rocha-Sosa et al., 1989). For this, a PCR product was first of all amplified from a tuber-specific *solanum tuberosum* (cv Désirée) cDNA library using the primers B1_Asp (GAT GGG TAC CAG CAC TTC TAC TTG GCA GAG G) (SEQ ID NO. 17) and B2_Sal (TCA AGT CGA CCA CAA CCA GTC CAT TTC TGG) (SEQ ID NO. 18) resulting in the cleavage sites Asp718 and SalI being added. The PCR product (625 bp) which was obtained was cloned, in the antisense orientation with regard to the B33 promoter, by way of these two cleavage sites. A second PCR fragment, which was amplified from a tuber-specific *solanum tuberosum* (cv Désirée) cDNA library using the primers B3_Sal (GCT TGT CGA CGG GAG AAT TTT GTC CAG AGG) (SEQ ID NO. 23) and B4_Sal (GAT CGT CGA CAG CAC TTC TAC TTG GCA GAG G) (SEQ ID NO. 24), and which was identical to 301 bp of the first fragment, was cloned, by way of the SalI cleavage site, downstream of the first fragment but in the sense orientation with regard to the B33 promoter. This arrangement is designated an inverted repeat (RNAi technology).

c) Producing Transgenic Potato Plants

In order to generate transgenic potato plants in which the activities of a BEI protein, of an SSIII protein, of a BEII protein and of a protein having the amino acid sequence depicted under SEQ ID NO 12 or SEQ ID NO 14 were reduced, agrobacteria were used, as described in Rocha-Sosa et al. (EMBO J. 8, (1989), 23-29), to transfer the T-DNA of plasmid AN 54-196 into transgenic potato plants belonging to the line 110CF-003. The plants obtained as a result of being transformed with plasmid AN 53-196 were designated 376SO.

5. Analyzing the Starch in Plants in which the Activities of a BEI Protein, of an SSIII Protein, of a BEII Protein and of a Protein which Exhibits the Amino Acid Sequence Depicted in SEQ ID NO 12 or SEQ ID NO 14 are Reduced Starch was isolated from the tubers of different independent lines derived from the transformations 110CF and 376SO, described in the abovementioned examples, and from the tubers of wild-type plants (cv Désirée). The physiochemical properties of these starches were then analyzed.

a) RVA Analysis

The viscosity profile of starches which were isolated from the tubers of the lines derived from the transformations 110CF and 376SO, described in the abovementioned examples, and from the tubers of wild-type plants (cv Désirée) were determined using RVA analytic method 2 as described under item 4 in the general methods. The gel strength was then determined using the method described under item 3 in the general methods.

Table 1 below summarizes the results of the RVA analysis and of the gel strength analysis. The values which are given are the measured values which were in each case determined expressed as a percentage based on the corresponding measured value, which was in each case stipulated to be 100%, of starch which was isolated from the tubers of wild-type plants.

TABLE 1

RVA in accordance with method 2, TA strength of CaCl₂-pasted starches

|  | RVA Max (%) | RVA Min (%) | RVA Fin (%) | RVA Set (%) | RVA T (%) | RVA Pasting temperature | TA "strength 1" |
|---|---|---|---|---|---|---|---|
| Wild type (Désirée) | 100.0% | 100.0% | 100.0% | 100.0% | 100.0% | 100.0% | 100% |
| 110CF-003 | 97.1% | 314.5% | 165.9% | 83.6% | 167.2% | 115.6% | 159.4% |
| 376SO-010 | 103.9% | 284.4% | 153.7% | 81.7% | 143.7% | 115.8% | 195.3% |
| 376SO-047 | 94.1% | 292.4% | 163.3% | 92.9% | 164.3% | 134.2% | 175.5% |
| 376SO-087 | 82.5% | 252.9% | 147.1% | 89.4% | 157.6% | 125.7% | 173.4% |

The viscosity profiles of starches which were isolated from the tubers of the lines 110CF-003 and 376SO-010 were determined using RVA analytical method 3, which is described under item 4 in the general methods.

Table 2 below gives the values which are obtained for the pasting temperatures of the lines which were measured:

TABLE 2

|  | Pasting temperature |
|---|---|
| 110CF-003 | 78.8° C. |
| 376SO-010 | 93.6° C. | b) Analyzing the Contents of Phosphate and Amylose

The C6 phosphate content of starches which were isolated from the tubers of the lines derived from the transformations 110CF and 376SO described in the abovementioned examples, and from the tubers of wild-type plants (cv Désirée) was determined using the method described under item 2 in the general methods.

The total phosphate content of starches which were isolated from the tubers of the lines derived from the transformations 110CF and 376SO, described in the abovementioned examples, and from the tubers of wild-type plants (cv Désirée) was determined using the method described under item 2 in the general methods.

The amylose content of starches which were isolated from the tubers of individual lines derived from the transformations 110CF and 376SO, described in the abovementioned examples, and from the tubers of wild-type plants (cv Désirée) was determined using the method described under item 1 in the General Methods.

The results obtained from representative lines are depicted in table 3.

The quantity of C6 phosphate or total phosphate was first of all determined in μmol/g of starch. All the other values given in table 3 relating to the C6 phosphate content or the total phosphate content can be calculated from the initially determined value (μmol/g of starch). For these calculations, 31 is used as the value for the molecular weight of phosphorus.

The "quantity [%]" values in each case indicate the quantity of the substance concerned expressed as a percentage of the total quantity of the starch.

The "based on wild type [%]" values in each case indicate the quantity of the substance concerned expressed as a percentage of the corresponding quantity of the same substance in starch which has been isolated from the tubers of wild-type plants.

6. Analyzing the Side Chain Distribution of the Amylopectin

The side chain distribution of starches which were isolated from the tubers of individual lines derived from the transformations 110CF and 376SO, as described in the abovementioned examples, and from the tubers of wild-type plants (cv Désirée) was determined using the method described under item 6 in the General Methods. The results are summarized in table 4.

TABLE 4

|  | Desi | 110-CF | 376-SO-10 | 376-SO-47 | 376-SO-87 |
|---|---|---|---|---|---|
| <dp11 | 100.0% | 24.2% | 14.3% | 15.8% | 13.5% |
| dp11-dp18 | 100.0% | 45.7% | 36.3% | 40.1% | 37.5% |
| dp19-dp24 | 100.0% | 77.6% | 68.8% | 72.2% | 71.3% |
| dp25-dp30 | 100.0% | 100.2% | 93.6% | 96.2% | 94.8% |
| dp31-dp36 | 100.0% | 101.9% | 98.5% | 100.0% | 98.3% |
| dp37-dp42 | 100.0% | 98.4% | 96.8% | 97.4% | 96.6% |
| dp43-dp48 | 100.0% | 103.6% | 103.1% | 103.2% | 103.1% |
| dp49-dp55 | 100.0% | 118.7% | 119.8% | 119.3% | 119.9% |
| dp56-dp61 | 100.0% | 139.6% | 143.4% | 142.1% | 143.2% |
| dp62-dp123 | 100.0% | 231.1% | 256.3% | 246.5% | 252.0% |
| >123dp | 100.0% | 929.4% | 1236.3% | 1135.4% | 1209.4% |

TABLE 3

|  | C6 Position | | | Total Quantity | | |
|---|---|---|---|---|---|---|
|  | [μmol of phosphate/g of starch] | [μg of phosphorus/g of starch] | Based on wild type [%] | [μmol of phosphate/g of starch] | [mg of phosphorus/ 100 g] | [μg of phosphorus/g of starch] |
| wt-1 | 10.30 | 319.30 |  | 21.10 | 65.41 | 654.10 |
| wt-2 | 8.60 | 266.60 |  | 19.90 | 61.69 | 616.90 |
| wt mean | 9.45 | 292.95 |  | 20.50 | 63.55 | 635.50 |
| 110CF 003-1 | 44.3 | 1373.30 |  | 74.30 | 230.33 | 2303.30 |
| 110CF 003-2 | 42.8 | 1326.80 |  | 75.10 | 232.81 | 2328.10 |
| 110 CF 003 mean | 43.55 | 1350.05 | 461% | 74.70 | 231.57 | 2315.70 |

TABLE 3-continued

| | | | | | | |
|---|---|---|---|---|---|---|
| 396SO 010 | 55.20 | 1711.20 | 584% | 90.80 | 281.48 | 2814.80 |
| 396SO 047 | 46.80 | 1450.80 | 495% | 87.00 | 269.70 | 2697.00 |
| 396SO 087 | 54.00 | 1674.00 | 571% | 88.80 | 275.28 | 2752.80 |

| | Total Quantity | | Amylose | |
|---|---|---|---|---|
| | Quantity [%] | Based on wild type [%] | Quantity [%] | Based on wild type [%] |
| wt-1 | 0.07 | | 23.1 | |
| wt-2 | 0.06 | | 23.3 | |
| wt mean | 0.06 | | 23.20 | |
| 110CF 003-1 | 0.23 | | 40.6 | |
| 110CF 003-2 | 0.23 | | 39.2 | |
| 110 CF 003 mean | 0.23 | 364% | 39.9 | 172% |
| 396SO 010 | 0.28 | 443% | 45.5 | 196% |
| 396SO 047 | 0.27 | 424% | 45.3 | 195% |
| 396SO 087 | 0.28 | 433% | 41.9 | 181% |

What is claimed:

1. A modified starch isolated from potato plants comprising an amylose content, as measured by the method of Hovenkamp-Hermelink et al. of between 40% and 50%, a phosphorus content of from 80 to 95 μmol of phosphate per gram of starch (dry weight), and an altered amylopectin side-chain distribution as compared with starch isolated from corresponding wild-type potato plants,
wherein the proportion of side chains having a DP of less than 11 and/or a DP of from 11 to 18 is reduced, and the proportion of side chains having a DP of from 56 to 61 and a DP of from 62 to 123 is increased, as compared with starch isolated from corresponding wild-type potato plants, and
wherein the proportion of the amylopectin side chains having a DP of from 62 to 123 is increased by at least 150%, based on the quantity of the amylopectin side chains having a DP of from 62 to 123 in starch isolated from corresponding wild-type plants.

2. The modified starch of claim 1, further comprising a C6 phosphorus content of from 45 to 60 μmol of phosphate per gram of starch (dry weight).

3. The modified starch of claim 1, wherein the proportion of the amylopectin side chains having a DP of from 62 to 123 is increased by between 150% and 200%, based on the quantity of the amylopectin side chains having a DP of from 62 to 123 in starch isolated from corresponding wild-type plants.

4. The modified starch of claim 2, wherein the proportion of the amylopectin side chains having a DP of from 62 to 123 is increased by between 150% and 200%, based on the quantity of the amylopectin side chains having a DP of from 62 to 123 in starch isolated from corresponding wild-type plants.

5. A method for preparing a derivatized starch comprising derivatizing the modified starch of claim 1 by altering said starch via a chemical, enzymatic, thermal, or mechanical method.

6. The method of claim 5, wherein the chemical method is an acid treatment, etherification, oxidation, esterification, crosslinking, or graft polymerization.

7. The modified starch of claim 1, wherein the proportion of side chains having a DP of from 56 to 61 is increased by at least 40%, based on the quantity of the amylopectin side chains having a DP of from 56 to 61 in starch isolated from corresponding wild-type potato plants.

8. Starch obtainable from a potato plant cell which exhibits an activity
   (a) of one or more SSIII proteins which occur endogenously in the plant cell;
   (b) of one or more BEI proteins which occur endogenously in the plant cell;
   (c) of one or more BEII proteins which occur endogenously in the plant cell; and
   (d) of one or more proteins which occur endogenously in the plant cell and which exhibit an at least 80% identity with the amino acid sequence of SEQ ID NO 12 or SEQ ID NO 14,
   which is reduced as compared with that of corresponding wild-type plant cells,
   wherein said starch comprises an altered amylopectin side-chain distribution as compared with starch isolated from corresponding wild-type potato plants, and
   further wherein the proportion of the amylopectin side chains having a DP of from 62 to 123 is increased by at least 150%, based on the quantity of the amylopectin side chains having a DP of from 62 to 123 in starch isolated from corresponding wild-type plants.

9. The starch of claim 8, wherein said potato plant cell comprises
   (a) a first foreign nucleic acid molecule that reduces the expression of at least one endogenous gene encoding a SSIII protein;
   (b) a second foreign nucleic acid molecule that reduces the expression of at least one endogenous gene encoding a BEI protein; and
   (c) a third foreign nucleic acid molecule that reduces the expression of at least one endogenous gene encoding a BEII protein; and (d) a fourth foreign nucleic acid molecule that reduces the expression of at least one nucleic acid molecule that has an identity of at least 80% with SEQ ID NO 11 or SEQ ID NO 13.

10. The starch of claim 9, wherein
(a) said first foreign nucleic acid molecule is
   (i) a nucleic acid molecule, which encodes a protein with the amino acid sequence of SEQ ID NO 2;
   (ii) a nucleic acid molecule, which encodes a protein, the sequence of which has an identity of at least 95% with the amino acid sequence of SEQ ID NO 2;
   (iii) a nucleic acid molecule, which comprises the nucleotide sequence of SEQ ID NO 1 or a complementary sequence thereof;
   (iv) a nucleic acid molecule, which has an identity of at least 95% with nucleic acid sequence with SEQ ID NO 1; or
   (v) a nucleic acid molecule, which hybridizes with at least with one strand of the nucleic acid molecules described under (i) or (iii) under stringent conditions;
(b) said second foreign nucleic acid molecule is
   (i) a nucleic acid molecule, which encodes a protein with the amino acid sequence of SEQ ID NO 5;
   (ii) a nucleic acid molecule, which encodes a protein, the sequence of which has an identity of at least 95% with the amino acid sequence of SEQ ID NO 5;
   (iii) a nucleic acid molecule, which comprises the nucleotide sequence of SEQ ID NO 4 or a complementary sequence thereof;
   (iv) a nucleic acid molecule, which has an identity of at least 95% with nucleic acid sequence with SEQ ID NO 4; or
   (v) a nucleic acid molecule, which hybridizes with at least with one strand of the nucleic acid molecules described under (i) or (iii) under stringent conditions;
(c) said third foreign nucleic acid molecule is
   (i) a nucleic acid molecule, which encodes a protein with the amino acid sequence of SEQ ID NO 7;
   (ii) a nucleic acid molecule, which encodes a protein, the sequence of which has an identity of at least 95% with the amino acid sequence of SEQ ID NO 7;
   (iii) a nucleic acid molecule, which comprises the nucleotide sequence of SEQ ID NO 6 or a complementary sequence thereof;
   (iv) a nucleic acid molecule, which has an identity of at least 95% with nucleic acid sequence with SEQ ID NO 6; or
   (v) a nucleic acid molecule, which hybridizes with at least with one strand of the nucleic acid molecules described under (i) or (iii) under stringent conditions; and
(d) said fourth foreign nucleic acid molecule is
   (i) a nucleic acid molecule, which encodes a protein with the amino acid sequence of SEQ ID NO 12 or 14;
   (ii) a nucleic acid molecule, which encodes a protein, the sequence of which has an identity of at least 95% with the amino acid sequence of SEQ ID NO 12 or 14;
   (iii) a nucleic acid molecule, which comprises the nucleotide sequence of SEQ ID NO 11 or 13 or a complementary sequence thereof;
   (iv) a nucleic acid molecule, which has an identity of at least 95% with nucleic acid sequence with SEQ ID NO 11 or 13; or
   (v) a nucleic acid molecule, which hybridizes with at least with one strand of the nucleic acid molecules described under (i) or (iii) under stringent conditions.

11. The starch of claim 9, wherein
(a) said first foreign nucleic acid molecule is
   (i) a DNA molecule encoding at least one antisense RNA that reduces the expression of at least one endogenous gene encoding a SSIII protein;
   (ii) a DNA molecule which, via a co-suppression effect, reduces the expression of at least one endogenous gene encoding a SSIII protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
(b) said second foreign nucleic acid molecule is
   (i) a DNA molecule encoding at least one antisense RNA that reduces the expression of at least one endogenous gene encoding a BEI protein;
   (ii) a DNA molecule which, via a co-suppression effect, reduces the expression of at least one endogenous gene encoding a BEI protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein;
(c) said third foreign nucleic acid molecule is
   (i) a DNA molecule encoding at least one antisense RNA that reduces the expression of at least one endogenous gene encoding a BEII protein;
   (ii) a DNA molecule which, via a co-suppression effect, reduces the expression of at least one endogenous gene encoding a BEII protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein; and
(d) said fourth foreign nucleic acid molecule is
   (i) a DNA molecule encoding at least one antisense RNA that reduces the expression of at least one endogenous gene encoding SEQ ID NO 12 or 14;
   (ii) a DNA molecule which, via a co-suppression effect, reduces the expression of at least one endogenous gene encoding SEQ ID NO 12 or 14; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO 12 or 14.

12. A plant cell or plant which exhibits an activity
(a) of one or more SSIII proteins which occur endogenously in the plant;
(b) of one or more BEI proteins which occur endogenously in the plant;
(c) of one or more BEII proteins which occur endogenously in the plant; and
(d) of one or more proteins which occur endogenously in the plant and which exhibit an at least 80% identity with the amino acid sequence of SEQ ID NO. 12 or SEQ ID NO. 14,
which is reduced as compared with that of corresponding wild-type plants, wherein said plant cell or plant synthesizes a starch comprising an altered amylopectin side-chain distribution as compared with starch isolated from corresponding wild-type potato plants, and further wherein the proportion of the amylopectin side chains having a DP of from 62 to 123 is increased by at least 150%, based on the quantity of the amylopectin side chains having a DP of from 62 to 123 in starch isolated from corresponding wild-type plants.

13. The plant cell or plant of claim 12, wherein said plant cell or plant comprises
   (a) a first foreign nucleic acid molecule that reduces the expression of at least one endogenous gene encoding a SSIII protein;
   (b) a second foreign nucleic acid molecule that reduces the expression of at least one endogenous gene encoding a BEI protein; and
   (c) a third foreign nucleic acid molecule that reduces the expression of at least one endogenous gene encoding a BEII protein; and
   (d) a fourth foreign nucleic acid molecule that reduces the expression of at least one nucleic acid molecule that has an identity of at least 80% with SEQ ID NO 11 or SEQ ID NO 13.

14. The plant cell or plant of claim 13, wherein
   (a) said first foreign nucleic acid molecule is
      (i) a nucleic acid molecule, which encodes a protein with the amino acid sequence of SEQ ID NO 2;
      (ii) a nucleic acid molecule, which encodes a protein, the sequence of which has an identity of at least 95% with the amino acid sequence of SEQ ID NO 2;
      (iii) a nucleic acid molecule, which comprises the nucleotide sequence of SEQ ID NO 1 or a complementary sequence thereof;
      (iv) a nucleic acid molecule, which has an identity of at least 95% with nucleic acid sequence with SEQ ID NO 1; or
      (v) a nucleic acid molecule, which hybridizes with at least with one strand of the nucleic acid molecules described under (i) or (iii) under stringent conditions;
   (b) said second foreign nucleic acid molecule is
      (i) a nucleic acid molecule, which encodes a protein with the amino acid sequence of SEQ ID NO 5;
      (ii) a nucleic acid molecule, which encodes a protein, the sequence of which has an identity of at least 95% with the amino acid sequence of SEQ ID NO 5;
      (iii) a nucleic acid molecule, which comprises the nucleotide sequence of SEQ ID NO 4 or a complementary sequence thereof;
      (iv) a nucleic acid molecule, which has an identity of at least 95% with nucleic acid sequence with SEQ ID NO 4; or
      (v) a nucleic acid molecule, which hybridizes with at least with one strand of the nucleic acid molecules described under (i) or (iii) under stringent conditions;
   (c) said third foreign nucleic acid molecule is
      (i) a nucleic acid molecule, which encodes a protein with the amino acid sequence of SEQ ID NO 7;
      (ii) a nucleic acid molecule, which encodes a protein, the sequence of which has an identity of at least 95% with the amino acid sequence of SEQ ID NO 7;
      (iii) a nucleic acid molecule, which comprises the nucleotide sequence of SEQ ID NO 6 or a complementary sequence thereof;
      (iv) a nucleic acid molecule, which has an identity of at least 95% with nucleic acid sequence with SEQ ID NO 6; or
      (v) a nucleic acid molecule, which hybridizes with at least with one strand of the nucleic acid molecules described under (i) or (iii) under stringent conditions; and
   (d) said fourth foreign nucleic acid molecule is
      (i) a nucleic acid molecule, which encodes a protein with the amino acid sequence of SEQ ID NO 12 or 14;
      (ii) a nucleic acid molecule, which encodes a protein, the sequence of which has an identity of at least 95% with the amino acid sequence of SEQ ID NO 12 or 14;
      (iii) a nucleic acid molecule, which comprises the nucleotide sequence of SEQ ID NO 11 or 13 or a complementary sequence thereof;
      (iv) a nucleic acid molecule, which has an identity of at least 95% with nucleic acid sequence with SEQ ID NO 11 or 13; or
      (v) a nucleic acid molecule, which hybridizes with at least with one strand of the nucleic acid molecules described under (i) or (iii) under stringent conditions.

15. The plant cell or plant of claim 13, wherein
   (a) said first foreign nucleic acid molecule is
      (i) a DNA molecule encoding at least one antisense RNA that reduces the expression of at least one endogenous gene encoding a SSIII protein;
      (ii) a DNA molecule which, via a co-suppression effect, reduces the expression of at least one endogenous gene encoding a SSIII protein; or
      (iii) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
   (b) said second foreign nucleic acid molecule is
      (i) a DNA molecule encoding at least one antisense RNA that reduces the expression of at least one endogenous gene encoding a BEI protein;
      (ii) a DNA molecule which, via a co-suppression effect, reduces the expression of at least one endogenous gene encoding a BEI protein; or
      (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein;
   (c) said third foreign nucleic acid molecule is
      (i) a DNA molecule encoding at least one antisense RNA that reduces the expression of at least one endogenous gene encoding a BEII protein;
      (ii) a DNA molecule which, via a co-suppression effect, reduces the expression of at least one endogenous gene encoding a BEII protein; or
      (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein; and
   (d) said fourth foreign nucleic acid molecule is
      (i) a DNA molecule encoding at least one antisense RNA that reduces the expression of at least one endogenous gene encoding SEQ ID NO 12 or 14;
      (ii) a DNA molecule which, via a co-suppression effect, reduces the expression of at least one endogenous gene encoding SEQ ID NO 12 or 14; or (iii) a DNA molecule that simultaneously encodes at least one antisense RNA and at least one sense RNA, where said antisense RNA and said sense RNA form a double-stranded RNA molecule that reduces the expression of at least one endogenous gene encoding SEQ II) NO 12 or 14.

16. A method of manufacturing starch comprising extracting starch from a potato plant cell, wherein said plant cell exhibits an activity
   (a) of one or more SSIII proteins which occur endogenously in the plant cell;
   (b) of one or more BEI proteins which occur endogenously in the plant cell;
   (c) of one or more BEII proteins which occur endogenously in the plant cell; and
   (d) of one or more proteins which occur endogenously in the plant cell and which exhibit an at least 80% identity with the amino acid sequence of SEQ ID NO 12 or SEQ ID NO 14,
   which is reduced as compared with that of corresponding wild-type plant cells,
   wherein said starch comprises an altered amylopectin side-chain distribution as compared with starch isolated from corresponding wild-type potato plants, and
   further wherein the proportion of the amylopectin side chains having a DP of from 62 to 123 is increased by at least 150%, based on the quantity of the amylopectin side chains having a DP of from 62 to 123 in starch isolated from corresponding wild-type plants.

17. The method of claim 16, wherein said plant cell comprises
   (a) a first foreign nucleic acid molecule that reduces the expression of at least one endogenous gene encoding a SSIII protein;
   (b) a second foreign nucleic acid molecule that reduces the expression of at least one endogenous gene encoding a BEI protein; and
   (c) a third foreign nucleic acid molecule that reduces the expression of at least one endogenous gene encoding a BEII protein; and
   (d) a fourth foreign nucleic acid molecule that reduces the expression of at least one nucleic acid molecule that has an identity of at least 80% with SEQ ID NO 11 or SEQ ID NO 13.

18. The method of claim 17, wherein
   (a) said first foreign nucleic acid molecule is
      (i) a nucleic acid molecule, which encodes a protein with the amino acid sequence of SEQ ID NO 2;
      (ii) a nucleic acid molecule, which encodes a protein, the sequence of which has an identity of at least 95% with the amino acid sequence of SEQ ID NO 2;
      (iii) a nucleic acid molecule, which comprises the nucleotide sequence of SEQ ID NO 1 or a complementary sequence thereof;
      (iv) a nucleic acid molecule, which has an identity of at least 95% with nucleic acid sequence with SEQ ID NO 1; or
      (v) a nucleic acid molecule, which hybridizes with at least with one strand of the nucleic acid molecules described under (i) or (iii) under stringent conditions;
   (b) said second foreign nucleic acid molecule is
      (i) a nucleic acid molecule, which encodes a protein with the amino acid sequence of SEQ ID NO 5;
      (ii) a nucleic acid molecule, which encodes a protein, the sequence of which has an identity of at least 95% with the amino acid sequence of SEQ ID NO 5;
      (iii) a nucleic acid molecule, which comprises the nucleotide sequence of SEQ ID NO 4 or a complementary sequence thereof;
      (iv) a nucleic acid molecule, which has an identity of at least 95% with nucleic acid sequence with SEQ ID NO 4; or
      (v) a nucleic acid molecule, which hybridizes with at least with one strand of the nucleic acid molecules described under (i) or (iii) under stringent conditions;
   (c) said third foreign nucleic acid molecule is
      (i) a nucleic acid molecule, which encodes a protein with the amino acid sequence of SEQ ID NO 7;
      (ii) a nucleic acid molecule, which encodes a protein, the sequence of which has an identity of at least 95% with the amino acid sequence of SEQ ID NO 7;
      (iii) a nucleic acid molecule, which comprises the nucleotide sequence of SEQ ID NO 6 or a complementary sequence thereof;
      (iv) a nucleic acid molecule, which has an identity of at least 95% with nucleic acid sequence with SEQ ID NO 6; or
      (v) a nucleic acid molecule, which hybridizes with at least with one strand of the nucleic acid molecules described under (i) or (iii) under stringent conditions; and
   (d) said fourth foreign nucleic acid molecule is
      (i) a nucleic acid molecule, which encodes a protein with the amino acid sequence of SEQ ID NO 12 or 14;
      (ii) a nucleic acid molecule, which encodes a protein, the sequence of which has an identity of at least 95% with the amino acid sequence of SEQ ID NO 12 or 14;
      (iii) a nucleic acid molecule, which comprises the nucleotide sequence of SEQ ID NO 11 or 13 or a complementary sequence thereof;
      (iv) a nucleic acid molecule, which has an identity of at least 95% with nucleic acid sequence with SEQ ID NO 11 or 13; or
      (v) a nucleic acid molecule, which hybridizes with at least with one strand of the nucleic acid molecules described under (i) or (iii) under stringent conditions.

19. The method of claim 17, wherein
   (a) said first foreign nucleic acid molecule is
      (i) a DNA molecule encoding at least one antisense RNA that reduces the expression of at least one endogenous gene encoding a SSIII protein;
      (ii) a DNA molecule which, via a co-suppression effect, reduces the expression of at least one endogenous gene encoding a SSIII protein; or
      (iii) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
   (b) said second foreign nucleic acid molecule is
      (i) a DNA molecule encoding at least one antisense RNA that reduces the expression of at least one endogenous gene encoding a BEI protein;
      (ii) a DNA molecule which, via a co-suppression effect, reduces the expression of at least one endogenous gene encoding a BEI protein; or
      (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein;

(c) said third foreign nucleic acid molecule is
  (i) a DNA molecule encoding at least one antisense RNA that reduces the expression of at least one endogenous gene encoding a BEII protein;
  (ii) a DNA molecule which, via a co-suppression effect, reduces the expression of at least one endogenous gene encoding a BEII protein; or
  (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein; and (d) said fourth foreign nucleic acid molecule is
  (i) a DNA molecule encoding at least one antisense RNA that reduces the expression of at least one endogenous gene encoding SEQ ID NO 12 or 14;
  (ii) a DNA molecule which, via a co-suppression effect, reduces the expression of at least one endogenous gene encoding SEQ ID NO 12 or 14; or
  (iii) a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO 12 or 14.

\* \* \* \* \*

SEQUENCE LISTING

<160> NUMBER OF SEQ ID NOS: 24

<210> SEQ ID NO 1
<211> LENGTH: 4167
<212> TYPE: DNA
<213> ORGANISM: Solanum tuberosum
<220> FEATURE:
<221> NAME/KEY: CDS
<222> LOCATION: (207)..(3899)
<223> OTHER INFORMATION: Soluble starch synthase III
<300> PUBLICATION INFORMATION:
<301> AUTHORS: Abel,G.J., Springer,F., Willmitzer,L. and Kossmann,J.
<302> TITLE: Cloning and functional analysis of a cDNA encoding a novel 139 kDa
<303> JOURNAL: Plant J.
<304> VOLUME: 10
<305> ISSUE: 6
<306> PAGES: 981-991
<307> DATE: 1996
<308> DATABASE ACCESSION NUMBER: X94400
<309> DATABASE ENTRY DATE: 1995-12-22
<313> RELEVANT RESIDUES IN SEQ ID NO: (1)..(4167)
<300> PUBLICATION INFORMATION:
<308> DATABASE ACCESSION NUMBER: EMBL / X94400
<309> DATABASE ENTRY DATE: 1997-04-16
<313> RELEVANT RESIDUES IN SEQ ID NO: (1)..(4167)

<400> SEQUENCE: 1

```
tttttaata gattttaaa accccattaa agcaaatacg tatataattg cagcacagat      60
acagagaggg agagagaaag atagtgtgtt gatgaaggag aagagagata tttcacatgg     120
gatgttctat tgattctgt ggtgaacaag agttttacaa agaacattcc tttttctttt     180
tttcttggtt cttgtgtggg tcagcc atg gat gtt cca ttt cca ctg cat aga     233
                               Met Asp Val Pro Phe Pro Leu His Arg
                                 1               5 cca ttg agt tgc aca agt gtc tcc aat gca ata acc cac ctc aag atc     281
Pro Leu Ser Cys Thr Ser Val Ser Asn Ala Ile Thr His Leu Lys Ile
 10              15                  20                  25 aaa cct ttt ctt ggg ttt gtc tct cat gga acc aca agt cta tca gta     329
Lys Pro Phe Leu Gly Phe Val Ser His Gly Thr Thr Ser Leu Ser Val
                 30                  35                  40 caa tct tct tca tgg agg aag gat gga atg gtt act ggg gtt tca ttt     377
Gln Ser Ser Ser Trp Arg Lys Asp Gly Met Val Thr Gly Val Ser Phe
             45                  50                  55 cca ttt tgt gca aat ctc tcg gga aga aga cgg aga aaa gtt tca act     425
```

```
        Pro Phe Cys Ala Asn Leu Ser Gly Arg Arg Arg Lys Val Ser Thr
                    60                  65                  70 act agg agt caa gga tct tca cct aag ggg ttt gtg cca agg aag ccc     473
Thr Arg Ser Gln Gly Ser Ser Pro Lys Gly Phe Val Pro Arg Lys Pro
 75                  80                  85 tca ggg atg agc acg caa aga aag gtt cag aag agc aat ggt gat aaa     521
Ser Gly Met Ser Thr Gln Arg Lys Val Gln Lys Ser Asn Gly Asp Lys
 90                  95                 100                 105 gaa agt caa agt act tca aca tct aaa gaa tct gaa att tcc aac cag     569
Glu Ser Gln Ser Thr Ser Thr Ser Lys Glu Ser Glu Ile Ser Asn Gln
                    110                 115                 120 aag acg gtt gaa gca aga gtt gaa act agt gac gat gac act aaa gta     617
Lys Thr Val Glu Ala Arg Val Glu Thr Ser Asp Asp Asp Thr Lys Val
                    125                 130                 135 gtg gtg agg gac cac aag ttt ctg gag gat gag gat gaa atc aat ggt     665
Val Val Arg Asp His Lys Phe Leu Glu Asp Glu Asp Glu Ile Asn Gly
                    140                 145                 150 tct act aaa tca ata agt atg tca cct gtt cgt gta tca tct caa ttt    713
Ser Thr Lys Ser Ile Ser Met Ser Pro Val Arg Val Ser Ser Gln Phe
                    155                 160                 165 gtt gaa agt gaa gaa act ggt ggt gat gac aag gat gct gta aag tta    761
Val Glu Ser Glu Glu Thr Gly Gly Asp Asp Lys Asp Ala Val Lys Leu
170                 175                 180                 185 aac aaa tca aag aga tcg gaa gag agt gat ttt cta att gat tct gta    809
Asn Lys Ser Lys Arg Ser Glu Glu Ser Asp Phe Leu Ile Asp Ser Val
                    190                 195                 200 ata aga gaa caa agt gga tct cag ggg gaa act aat gcc agt agc aag    857
Ile Arg Glu Gln Ser Gly Ser Gln Gly Glu Thr Asn Ala Ser Ser Lys
                    205                 210                 215 gga agc cat gct gtg ggt aca aaa ctt tat gag ata ttg cag gtg gat    905
Gly Ser His Ala Val Gly Thr Lys Leu Tyr Glu Ile Leu Gln Val Asp
                    220                 225                 230 gtt gag cca caa caa ttg aaa gaa aat aat gct ggg aat gtt gaa tac    953
Val Glu Pro Gln Gln Leu Lys Glu Asn Asn Ala Gly Asn Val Glu Tyr
                    235                 240                 245 aaa gga cct gta gca agt aag cta ttg gaa att act aag gct agt gat   1001
Lys Gly Pro Val Ala Ser Lys Leu Leu Glu Ile Thr Lys Ala Ser Asp
250                 255                 260                 265 gtg gaa cac act gaa agc aat gag att gat gac tta gac act aat agt   1049
Val Glu His Thr Glu Ser Asn Glu Ile Asp Asp Leu Asp Thr Asn Ser
                    270                 275                 280 ttc ttt aaa tca gat tta att gaa gag gat gag cca tta gct gca gga   1097
Phe Phe Lys Ser Asp Leu Ile Glu Glu Asp Glu Pro Leu Ala Ala Gly
                    285                 290                 295 aca gtg gag act gga gat tct tct cta aac tta aga ttg gag atg gaa   1145
Thr Val Glu Thr Gly Asp Ser Ser Leu Asn Leu Arg Leu Glu Met Glu
                    300                 305                 310 gca aat cta cgt agg cag gct ata gaa agg ctt gcc gag gaa aat tta   1193
Ala Asn Leu Arg Arg Gln Ala Ile Glu Arg Leu Ala Glu Glu Asn Leu
                    315                 320                 325 ttg caa ggg atc aga tta ttt tgt ttt cca gag gtt gta aaa cct gat   1241
Leu Gln Gly Ile Arg Leu Phe Cys Phe Pro Glu Val Val Lys Pro Asp
330                 335                 340                 345 gaa gat gtc gag ata ttt ctt aac aga ggt ctt tcc act ttg aag aat   1289
Glu Asp Val Glu Ile Phe Leu Asn Arg Gly Leu Ser Thr Leu Lys Asn
                    350                 355                 360 gag tct gat gtc ttg att atg gga gct ttt aat gag tgg cgc tat agg   1337
Glu Ser Asp Val Leu Ile Met Gly Ala Phe Asn Glu Trp Arg Tyr Arg
                    365                 370                 375 tct ttt act aca agg cta act gag act cat ctc aat gga gat tgg tgg   1385
```

-continued

```
Ser Phe Thr Thr Arg Leu Thr Glu Thr His Leu Asn Gly Asp Trp Trp
        380                 385                 390 tct tgc aag atc cat gtt ccc aag gaa gca tac agg gct gat ttt gtg        1433
Ser Cys Lys Ile His Val Pro Lys Glu Ala Tyr Arg Ala Asp Phe Val
395                 400                 405 ttt ttt aat gga caa gat gtc tat gac aac aat gat gga aat gac ttc        1481
Phe Phe Asn Gly Gln Asp Val Tyr Asp Asn Asn Asp Gly Asn Asp Phe
410                 415                 420                 425 agt ata act gtg aaa ggt ggt atg caa atc att gac ttt gaa aat ttc        1529
Ser Ile Thr Val Lys Gly Gly Met Gln Ile Ile Asp Phe Glu Asn Phe
        430                 435                 440 ttg ctt gag gag aaa tgg aga gaa cag gag aaa ctt gct aaa gaa caa        1577
Leu Leu Glu Glu Lys Trp Arg Glu Gln Glu Lys Leu Ala Lys Glu Gln
        445                 450                 455 gct gaa aga gaa aga cta gcg gaa gaa caa aga cga ata gaa gca gag        1625
Ala Glu Arg Glu Arg Leu Ala Glu Glu Gln Arg Arg Ile Glu Ala Glu
        460                 465                 470 aaa gct gaa att gaa gct gac aga gca caa gca aag gaa gag gct gca        1673
Lys Ala Glu Ile Glu Ala Asp Arg Ala Gln Ala Lys Glu Glu Ala Ala
        475                 480                 485 aag aaa aag aaa gta ttg cga gaa ttg atg gta aaa gcc acg aag act        1721
Lys Lys Lys Lys Val Leu Arg Glu Leu Met Val Lys Ala Thr Lys Thr
490                 495                 500                 505 cgt gat atc acg tgg tac ata gag cca agt gaa ttt aaa tgc gag gac        1769
Arg Asp Ile Thr Trp Tyr Ile Glu Pro Ser Glu Phe Lys Cys Glu Asp
        510                 515                 520 aag gtc agg tta tac tat aac aaa agt tca ggt cct ctc tcc cat gct        1817
Lys Val Arg Leu Tyr Tyr Asn Lys Ser Ser Gly Pro Leu Ser His Ala
        525                 530                 535 aag gac ttg tgg atc cac gga gga tat aat aat tgg aag gat ggt ttg        1865
Lys Asp Leu Trp Ile His Gly Gly Tyr Asn Asn Trp Lys Asp Gly Leu
        540                 545                 550 tct att gtc aaa aag ctt gtt aaa tct gag aga ata gat ggt gat tgg        1913
Ser Ile Val Lys Lys Leu Val Lys Ser Glu Arg Ile Asp Gly Asp Trp
555                 560                 565 tgg tat aca gag gtt gtt att cct gat cag gca ctt ttc ttg gat tgg        1961
Trp Tyr Thr Glu Val Val Ile Pro Asp Gln Ala Leu Phe Leu Asp Trp
570                 575                 580                 585 gtt ttt gct gat ggt cca ccc aag cat gcc att gct tat gat aac aat        2009
Val Phe Ala Asp Gly Pro Pro Lys His Ala Ile Ala Tyr Asp Asn Asn
            590                 595                 600 cac cgc caa gac ttc cat gcc att gtc ccc aac cac att ccg gag gaa        2057
His Arg Gln Asp Phe His Ala Ile Val Pro Asn His Ile Pro Glu Glu
        605                 610                 615 tta tat tgg gtt gag gaa gaa cat cag atc ttt aag aca ctt cag gag        2105
Leu Tyr Trp Val Glu Glu Glu His Gln Ile Phe Lys Thr Leu Gln Glu
        620                 625                 630 gag aga agg ctt aga gaa gcg gct atg cgt gct aag gtt gaa aaa aca        2153
Glu Arg Arg Leu Arg Glu Ala Ala Met Arg Ala Lys Val Glu Lys Thr
        635                 640                 645 gca ctt ctg aaa act gaa aca aag gaa aga act atg aaa tca ttt tta        2201
Ala Leu Leu Lys Thr Glu Thr Lys Glu Arg Thr Met Lys Ser Phe Leu
650                 655                 660                 665 ctg tct cag aag cat gta gta tat act gag cct ctt gat atc caa gct        2249
Leu Ser Gln Lys His Val Val Tyr Thr Glu Pro Leu Asp Ile Gln Ala
        670                 675                 680 gga agc agc gtc aca gtt tac tat aat ccc gcc aat aca gta ctt aat        2297
Gly Ser Ser Val Thr Val Tyr Tyr Asn Pro Ala Asn Thr Val Leu Asn
        685                 690                 695 ggt aaa cct gaa att tgg ttc aga tgt tca ttt aat cgc tgg act cac        2345
```

```
                Gly Lys Pro Glu Ile Trp Phe Arg Cys Ser Phe Asn Arg Trp Thr His
                        700                 705                 710 cgc ctg ggt cca ttg cca cct cag aaa atg tcg cct gct gaa aat ggc      2393
Arg Leu Gly Pro Leu Pro Pro Gln Lys Met Ser Pro Ala Glu Asn Gly
715                 720                 725 acc cat gtc aga gca act gtg aag gtt cca ttg gat gca tat atg atg      2441
Thr His Val Arg Ala Thr Val Lys Val Pro Leu Asp Ala Tyr Met Met
730                 735                 740                 745 gat ttt gta ttt tcc gag aga gaa gat ggt ggg att ttt gac aat aag      2489
Asp Phe Val Phe Ser Glu Arg Glu Asp Gly Gly Ile Phe Asp Asn Lys
                750                 755                 760 agc gga atg gac tat cac ata cct gtg ttt gga gga gtc gct aaa gaa      2537
Ser Gly Met Asp Tyr His Ile Pro Val Phe Gly Gly Val Ala Lys Glu
            765                 770                 775 cct cca atg cat att gtc cat att gct gtc gaa atg gca cca att gca      2585
Pro Pro Met His Ile Val His Ile Ala Val Glu Met Ala Pro Ile Ala
        780                 785                 790 aag gtg gga ggc ctt ggt gat gtt gtt act agt ctt tcc cgt gct gtt      2633
Lys Val Gly Gly Leu Gly Asp Val Val Thr Ser Leu Ser Arg Ala Val
795                 800                 805 caa gat tta aac cat aat gtg gat att atc tta cct aag tat gac tgt      2681
Gln Asp Leu Asn His Asn Val Asp Ile Ile Leu Pro Lys Tyr Asp Cys
810                 815                 820                 825 ttg aag atg aat aat gtg aag gac ttt cgg ttt cac aaa aac tac ttt      2729
Leu Lys Met Asn Asn Val Lys Asp Phe Arg Phe His Lys Asn Tyr Phe
                830                 835                 840 tgg ggt ggg act gaa ata aaa gta tgg ttt gga aag gtg gaa ggt ctc      2777
Trp Gly Gly Thr Glu Ile Lys Val Trp Phe Gly Lys Val Glu Gly Leu
            845                 850                 855 tcg gtc tat ttt ttg gag cct caa aac ggg tta ttt tcg aaa ggg tgc      2825
Ser Val Tyr Phe Leu Glu Pro Gln Asn Gly Leu Phe Ser Lys Gly Cys
        860                 865                 870 gtc tat ggt tgt agc aat gat ggt gaa cga ttt ggt ttc ttc tgt cac      2873
Val Tyr Gly Cys Ser Asn Asp Gly Glu Arg Phe Gly Phe Phe Cys His
875                 880                 885 gcg gct ttg gag ttt ctt ctg caa ggt gga ttt agt ccg gat atc att      2921
Ala Ala Leu Glu Phe Leu Leu Gln Gly Gly Phe Ser Pro Asp Ile Ile
890                 895                 900                 905 cat tgc cat gat tgg tct agt gct cct gtt gct tgg ctc ttt aag gaa      2969
His Cys His Asp Trp Ser Ser Ala Pro Val Ala Trp Leu Phe Lys Glu
                910                 915                 920 caa tat aca cac tat ggt cta agc aaa tct cgt ata gtc ttc acg ata      3017
Gln Tyr Thr His Tyr Gly Leu Ser Lys Ser Arg Ile Val Phe Thr Ile
            925                 930                 935 cat aat ctt gaa ttt ggg gca gat ctc att ggg aga gca atg act aac      3065
His Asn Leu Glu Phe Gly Ala Asp Leu Ile Gly Arg Ala Met Thr Asn
        940                 945                 950 gca gac aaa gct aca aca gtt tca cca act tac tca cag gag gtg tct      3113
Ala Asp Lys Ala Thr Thr Val Ser Pro Thr Tyr Ser Gln Glu Val Ser
955                 960                 965 gga aac cct gta att gcg cct cac ctt cac aag ttc cat ggt ata gtg      3161
Gly Asn Pro Val Ile Ala Pro His Leu His Lys Phe His Gly Ile Val
970                 975                 980                 985 aat ggg att gac cca gat att tgg gat cct tta aac gat aag ttc att      3209
Asn Gly Ile Asp Pro Asp Ile Trp Asp Pro Leu Asn Asp Lys Phe Ile
                990                 995                 1000 ccg att ccg tac  acc tca gaa aac gtt  gtt gaa ggc aaa aca  gca      3254
Pro Ile Pro Tyr Thr Ser Glu Asn Val  Val Glu Gly Lys Thr  Ala
                1005                1010                1015 gcc aag gaa gct  ttg cag cga aaa ctt  gga ctg aaa cag gct  gac      3299
```

-continued

```
                Ala Lys Glu Ala Leu Gln Arg Lys Leu Gly Leu Lys Gln Ala Asp
                    1020                1025                1030 ctt cct ttg gta gga att atc acc cgc tta act cac cag aaa gga          3344
Leu Pro Leu Val Gly Ile Ile Thr Arg Leu Thr His Gln Lys Gly
            1035                1040                1045 atc cac ctc att aaa cat gct att tgg cgc acc ttg gaa cgg aac          3389
Ile His Leu Ile Lys His Ala Ile Trp Arg Thr Leu Glu Arg Asn
        1050                1055                1060 gga cag gta gtc ttg ctt ggt tct gct cct gat cct agg gta caa          3434
Gly Gln Val Val Leu Leu Gly Ser Ala Pro Asp Pro Arg Val Gln
    1065                1070                1075 aac gat ttt gtt aat ttg gca aat caa ttg cac tcc aaa tat aat          3479
Asn Asp Phe Val Asn Leu Ala Asn Gln Leu His Ser Lys Tyr Asn
1080                1085                1090 gac cgc gca cga ctc tgt cta aca tat gac gag cca ctt tct cac          3524
Asp Arg Ala Arg Leu Cys Leu Thr Tyr Asp Glu Pro Leu Ser His
                1095                1100                1105 ctg ata tat gct ggt gct gat ttt att cta gtt cct tca ata ttt          3569
Leu Ile Tyr Ala Gly Ala Asp Phe Ile Leu Val Pro Ser Ile Phe
            1110                1115                1120 gag cca tgt gga cta aca caa ctt acc gct atg aga tat ggt tca          3614
Glu Pro Cys Gly Leu Thr Gln Leu Thr Ala Met Arg Tyr Gly Ser
        1125                1130                1135 att cca gtc gtg cgt aaa act gga gga ctt tat gat act gta ttt          3659
Ile Pro Val Val Arg Lys Thr Gly Gly Leu Tyr Asp Thr Val Phe
    1140                1145                1150 gat gtt gac cat gac aaa gag aga gca caa cag tgt ggt ctt gaa          3704
Asp Val Asp His Asp Lys Glu Arg Ala Gln Gln Cys Gly Leu Glu
1155                1160                1165 cca aat gga ttc agc ttt gat gga gca gat gct ggc gga gtt gat          3749
Pro Asn Gly Phe Ser Phe Asp Gly Ala Asp Ala Gly Gly Val Asp
                1170                1175                1180 tat gct ctg aat aga gct ctc tct gct tgg tac gat ggt cgg gat          3794
Tyr Ala Leu Asn Arg Ala Leu Ser Ala Trp Tyr Asp Gly Arg Asp
            1185                1190                1195 tgg ttc aac tct tta tgc aag cag gtc atg gaa caa gat tgg tct          3839
Trp Phe Asn Ser Leu Cys Lys Gln Val Met Glu Gln Asp Trp Ser
        1200                1205                1210 tgg aac cga cct gct ctt gat tat ttg gag ctt tac cat gct gct          3884
Trp Asn Arg Pro Ala Leu Asp Tyr Leu Glu Leu Tyr His Ala Ala
    1215                1220                1225 aga aag tta gaa tag ttagtttgtg agatgctagc agaaaaattc acgagatctg      3939
Arg Lys Leu Glu
1230 caatctgtac aggttcagtg tttgcgtctg acagctttt ttatttccta tatcaaagta     3999 taaatcaagt ctacactgag atcaatagca gacagtcctc agttcatttc attttttgtg    4059 caacatatga aagagcttag cctctaataa tgtagtcatt gatgattatt tgttttggga    4119 agaaatgaga aatcaaagga tgcaaaatac tctgaaaaaa aaaaaaaa                 4167

<210> SEQ ID NO 2
<211> LENGTH: 1230
<212> TYPE: PRT
<213> ORGANISM: Solanum tuberosum

<400> SEQUENCE: 2

Met Asp Val Pro Phe Pro Leu His Arg Pro Leu Ser Cys Thr Ser Val
1               5                   10                  15

Ser Asn Ala Ile Thr His Leu Lys Ile Lys Pro Phe Leu Gly Phe Val
            20                  25                  30
```

```
Ser His Gly Thr Thr Ser Leu Ser Val Gln Ser Ser Trp Arg Lys
         35                  40                  45

Asp Gly Met Val Thr Gly Val Ser Phe Pro Phe Cys Ala Asn Leu Ser
 50                  55                  60

Gly Arg Arg Arg Lys Val Ser Thr Thr Arg Ser Gln Gly Ser Ser
 65                  70                  75                  80

Pro Lys Gly Phe Val Pro Arg Lys Pro Ser Gly Met Ser Thr Gln Arg
                 85                  90                  95

Lys Val Gln Lys Ser Asn Gly Asp Lys Glu Ser Gln Ser Thr Ser Thr
             100                 105                 110

Ser Lys Glu Ser Glu Ile Ser Asn Gln Lys Thr Val Glu Ala Arg Val
             115                 120                 125

Glu Thr Ser Asp Asp Thr Lys Val Val Arg Asp His Lys Phe
             130                 135                 140

Leu Glu Asp Glu Asp Glu Ile Asn Gly Ser Thr Lys Ser Ile Ser Met
145                 150                 155                 160

Ser Pro Val Arg Val Ser Ser Gln Phe Val Glu Ser Glu Thr Gly
                 165                 170                 175

Gly Asp Asp Lys Asp Ala Val Lys Leu Asn Lys Ser Lys Arg Ser Glu
                 180                 185                 190

Glu Ser Asp Phe Leu Ile Asp Ser Val Ile Arg Glu Gln Ser Gly Ser
             195                 200                 205

Gln Gly Glu Thr Asn Ala Ser Ser Lys Gly Ser His Ala Val Gly Thr
             210                 215                 220

Lys Leu Tyr Glu Ile Leu Gln Val Asp Val Glu Pro Gln Gln Leu Lys
225                 230                 235                 240

Glu Asn Asn Ala Gly Asn Val Glu Tyr Lys Gly Pro Val Ala Ser Lys
                 245                 250                 255

Leu Leu Glu Ile Thr Lys Ala Ser Asp Val Glu His Thr Glu Ser Asn
                 260                 265                 270

Glu Ile Asp Asp Leu Asp Thr Asn Ser Phe Phe Lys Ser Asp Leu Ile
             275                 280                 285

Glu Glu Asp Glu Pro Leu Ala Ala Gly Thr Val Glu Thr Gly Asp Ser
             290                 295                 300

Ser Leu Asn Leu Arg Leu Glu Met Glu Ala Asn Leu Arg Arg Gln Ala
305                 310                 315                 320

Ile Glu Arg Leu Ala Glu Glu Asn Leu Leu Gln Gly Ile Arg Leu Phe
                 325                 330                 335

Cys Phe Pro Glu Val Val Lys Pro Asp Glu Asp Val Glu Ile Phe Leu
                 340                 345                 350

Asn Arg Gly Leu Ser Thr Leu Lys Asn Glu Ser Asp Val Leu Ile Met
             355                 360                 365

Gly Ala Phe Asn Glu Trp Arg Tyr Arg Ser Phe Thr Thr Arg Leu Thr
 370                 375                 380

Glu Thr His Leu Asn Gly Asp Trp Trp Ser Cys Lys Ile His Val Pro
385                 390                 395                 400

Lys Glu Ala Tyr Arg Ala Asp Phe Val Phe Phe Asn Gly Gln Asp Val
                 405                 410                 415

Tyr Asp Asn Asn Asp Gly Asn Asp Phe Ser Ile Thr Val Lys Gly Gly
             420                 425                 430

Met Gln Ile Ile Asp Phe Glu Asn Phe Leu Glu Glu Lys Trp Arg
             435                 440                 445

Glu Gln Glu Lys Leu Ala Lys Glu Gln Ala Glu Arg Glu Arg Leu Ala
```

-continued

```
            450                 455                 460
Glu Glu Gln Arg Arg Ile Glu Ala Glu Lys Ala Glu Ile Glu Ala Asp
465                 470                 475                 480

Arg Ala Gln Ala Lys Glu Ala Ala Lys Lys Lys Val Leu Arg
                485                 490                 495

Glu Leu Met Val Lys Ala Thr Lys Thr Arg Asp Ile Thr Trp Tyr Ile
                500                 505                 510

Glu Pro Ser Glu Phe Lys Cys Glu Asp Lys Val Arg Leu Tyr Tyr Asn
                515                 520                 525

Lys Ser Ser Gly Pro Leu Ser His Ala Lys Asp Leu Trp Ile His Gly
530                 535                 540

Gly Tyr Asn Asn Trp Lys Asp Gly Leu Ser Ile Val Lys Lys Leu Val
545                 550                 555                 560

Lys Ser Glu Arg Ile Asp Gly Asp Trp Trp Tyr Thr Glu Val Val Ile
                565                 570                 575

Pro Asp Gln Ala Leu Phe Leu Asp Trp Val Phe Ala Asp Gly Pro Pro
                580                 585                 590

Lys His Ala Ile Ala Tyr Asp Asn Asn His Arg Gln Asp Phe His Ala
                595                 600                 605

Ile Val Pro Asn His Ile Pro Glu Glu Leu Tyr Trp Val Glu Glu Glu
610                 615                 620

His Gln Ile Phe Lys Thr Leu Gln Glu Glu Arg Leu Arg Glu Ala
625                 630                 635                 640

Ala Met Arg Ala Lys Val Glu Lys Thr Ala Leu Leu Lys Thr Glu Thr
                645                 650                 655

Lys Glu Arg Thr Met Lys Ser Phe Leu Leu Ser Gln Lys His Val Val
                660                 665                 670

Tyr Thr Glu Pro Leu Asp Ile Gln Ala Gly Ser Ser Val Thr Val Tyr
                675                 680                 685

Tyr Asn Pro Ala Asn Thr Val Leu Asn Gly Lys Pro Glu Ile Trp Phe
690                 695                 700

Arg Cys Ser Phe Asn Arg Trp Thr His Arg Leu Gly Pro Leu Pro Pro
705                 710                 715                 720

Gln Lys Met Ser Pro Ala Glu Asn Gly Thr His Val Arg Ala Thr Val
                725                 730                 735

Lys Val Pro Leu Asp Ala Tyr Met Met Asp Phe Val Phe Ser Glu Arg
                740                 745                 750

Glu Asp Gly Gly Ile Phe Asp Asn Lys Ser Gly Met Asp Tyr His Ile
                755                 760                 765

Pro Val Phe Gly Gly Val Ala Lys Glu Pro Pro Met His Ile Val His
                770                 775                 780

Ile Ala Val Glu Met Ala Pro Ile Ala Lys Val Gly Gly Leu Gly Asp
785                 790                 795                 800

Val Val Thr Ser Leu Ser Arg Ala Val Gln Asp Leu Asn His Asn Val
                805                 810                 815

Asp Ile Ile Leu Pro Lys Tyr Asp Cys Leu Lys Met Asn Asn Val Lys
                820                 825                 830

Asp Phe Arg Phe His Lys Asn Tyr Phe Trp Gly Gly Thr Glu Ile Lys
                835                 840                 845

Val Trp Phe Gly Lys Val Glu Gly Leu Ser Val Tyr Phe Leu Glu Pro
                850                 855                 860

Gln Asn Gly Leu Phe Ser Lys Gly Cys Val Tyr Gly Cys Ser Asn Asp
865                 870                 875                 880
```

```
Gly Glu Arg Phe Gly Phe Phe Cys His Ala Ala Leu Glu Phe Leu Leu
            885                 890                 895

Gln Gly Gly Phe Ser Pro Asp Ile Ile His Cys His Asp Trp Ser Ser
        900                 905                 910

Ala Pro Val Ala Trp Leu Phe Lys Glu Gln Tyr Thr His Tyr Gly Leu
            915                 920                 925

Ser Lys Ser Arg Ile Val Phe Thr Ile His Asn Leu Glu Phe Gly Ala
        930                 935                 940

Asp Leu Ile Gly Arg Ala Met Thr Asn Ala Asp Lys Ala Thr Thr Val
945                 950                 955                 960

Ser Pro Thr Tyr Ser Gln Glu Val Ser Gly Asn Pro Val Ile Ala Pro
            965                 970                 975

His Leu His Lys Phe His Gly Ile Val Asn Gly Ile Asp Pro Asp Ile
        980                 985                 990

Trp Asp Pro Leu Asn Asp Lys Phe Ile Pro Ile Pro Tyr Thr Ser Glu
            995                 1000                1005

Asn Val Val Glu Gly Lys Thr Ala Ala Lys Glu Ala Leu Gln Arg
        1010                1015                1020

Lys Leu Gly Leu Lys Gln Ala Asp Leu Pro Leu Val Gly Ile Ile
        1025                1030                1035

Thr Arg Leu Thr His Gln Lys Gly Ile His Leu Ile Lys His Ala
        1040                1045                1050

Ile Trp Arg Thr Leu Glu Arg Asn Gly Gln Val Val Leu Leu Gly
        1055                1060                1065

Ser Ala Pro Asp Pro Arg Val Gln Asn Asp Phe Val Asn Leu Ala
        1070                1075                1080

Asn Gln Leu His Ser Lys Tyr Asn Asp Arg Ala Arg Leu Cys Leu
        1085                1090                1095

Thr Tyr Asp Glu Pro Leu Ser His Leu Ile Tyr Ala Gly Ala Asp
        1100                1105                1110

Phe Ile Leu Val Pro Ser Ile Phe Glu Pro Cys Gly Leu Thr Gln
        1115                1120                1125

Leu Thr Ala Met Arg Tyr Gly Ser Ile Pro Val Val Arg Lys Thr
        1130                1135                1140

Gly Gly Leu Tyr Asp Thr Val Phe Asp Val Asp His Asp Lys Glu
        1145                1150                1155

Arg Ala Gln Gln Cys Gly Leu Glu Pro Asn Gly Phe Ser Phe Asp
        1160                1165                1170

Gly Ala Asp Ala Gly Gly Val Asp Tyr Ala Leu Asn Arg Ala Leu
        1175                1180                1185

Ser Ala Trp Tyr Asp Gly Arg Asp Trp Phe Asn Ser Leu Cys Lys
        1190                1195                1200

Gln Val Met Glu Gln Asp Trp Ser Trp Asn Arg Pro Ala Leu Asp
        1205                1210                1215

Tyr Leu Glu Leu Tyr His Ala Ala Arg Lys Leu Glu
        1220                1225                1230

<210> SEQ ID NO 3
<211> LENGTH: 61
<212> TYPE: PRT
<213> ORGANISM: Solanum tuberosum

<400> SEQUENCE: 3

Arg Ser Phe Thr Thr Arg Leu Thr Glu Thr His Leu Asn Gly Asp Trp
1               5                   10                  15
```

```
Trp Ser Cys Lys Ile His Val Pro Lys Glu Ala Tyr Arg Ala Asp Phe
             20                  25                  30

Val Phe Phe Asn Gly Gln Asp Val Tyr Asp Asn Asn Asp Gly Asn Asp
             35                  40                  45

Phe Ser Ile Thr Val Lys Gly Gly Met Gln Ile Ile Asp
             50                  55                  60

<210> SEQ ID NO 4
<211> LENGTH: 1641
<212> TYPE: DNA
<213> ORGANISM: Solanum tuberosum

<400> SEQUENCE: 4
atgaagcaca gttcagctat ttccgctgtt ttgaccgatg acaattcgac aatggcaccc      60
ctagaggaag atgtcaacac tgaaaatatt ggcctcctaa atttggatcc aactttggaa     120
ccttatctag atcacttcag acacagaatg aagagatatg tggatcagaa atgctcatt     180 gaaaaatatg agggaccccct tgaggaattt gctcaaggtt atttaaaatt tggattcaac     240
agggaagatg gttgcatagt ctatcgtgaa tgggctcctg ctgctcagga agcagaagtt     300
attggcgatt tcaatggtag gaacggttct aaccacatga tggagaagga ccagtttggt     360
gtttggagta ttagaattcc tgatgttgac agtaagccag tcattccaca caactccaga     420
gttaagtttc gtttcaaaca tggtaatgga gtgtgggtag atcgtatccc tgcttggata     480
aagtatgcca ctgcagacgc cacaaagttt gcagcaccat atgatggtgt ctactgggac     540
ccaccacctt cagaaaggta ccacttcaaa taccctcgcc ctcccaaacc ccgagcccca     600
cgaatctacg aagcacatgt cggcatgagc agctctgagc acgtgtaaa ttcgtatcgt      660 gagtttgcag atgatgtttt acctcggatt aaggcaaata actataatac tgtccagttg     720
atggccataa tggaacattc ttactatgga tcatttggat atcatgttac aaactttttt     780
gctgtgagca atagatatgg aaacccggag gacctaaagt atctgataga taaagcacat     840
agcttgggtt tacaggttct ggtggatgta gttcacagtc atgcaagcaa taatgtcact     900
gatggcctca atggctttga tattggccaa ggttctcaag aatcctactt tcatgctgga     960
gagcgagggt accataagtt gtgggatagc aggctgttca actatgccaa tgggaggtt    1020 cttcgttccc ttctttccaa cttgaggtgg tggctagaag agtataactt tgacggattt    1080
cgatttgatg gaataacttc tatgctgtat gttcatcatg aatcaatat gggatttaca    1140 ggaaactata atgagtattt cagcgaggct acagatgttg atgctgtggt ctatttaatg    1200
ttggccaata atctgattca caagattttc ccagacgcaa ctgttattgc cgaagatgtt    1260
tctggtatgc cgggccttag ccggcctgtt tctgagggag gaattggttt tgattaccgc    1320
ctggcaatgg caatcccaga taagtggata gattatttaa agaataagaa tgatgaagat    1380
tggtccatga aggaagtaac atcgagtttg acaaatagga gatatacaga gaagtgtata    1440
gcatatgcgg agagccatga tcagtctatt gtcggtgaca agaccattgc atttctccta    1500
atgaacaaag agatgtattc tggcatgtct tgcttgacag atgcttctcc tgttgttgat    1560
gcaggaattg cgcttgacaa gatgatccat tttttttcaca atggccttgg gaggagaggg    1620
gtacctcaat ttcatgggta a                                             1641

<210> SEQ ID NO 5
<211> LENGTH: 546
<212> TYPE: PRT
<213> ORGANISM: Solanum tuberosum
<300> PUBLICATION INFORMATION:
<308> DATABASE ACCESSION NUMBER: Swiss Prot / P30924
```

<309> DATABASE ENTRY DATE: 1993-07-26

<400> SEQUENCE: 5

```
Met Lys His Ser Ser Ala Ile Ser Ala Val Leu Thr Asp Asp Asn Ser
1               5                   10                  15

Thr Met Ala Pro Leu Glu Glu Asp Val Asn Thr Glu Asn Ile Gly Leu
            20                  25                  30

Leu Asn Leu Asp Pro Thr Leu Glu Pro Tyr Leu Asp His Phe Arg His
        35                  40                  45

Arg Met Lys Arg Tyr Val Asp Gln Lys Met Leu Ile Glu Lys Tyr Glu
    50                  55                  60

Gly Pro Leu Glu Glu Phe Ala Gln Gly Tyr Leu Lys Phe Gly Phe Asn
65                  70                  75                  80

Arg Glu Asp Gly Cys Ile Val Tyr Arg Glu Trp Ala Pro Ala Ala Gln
                85                  90                  95

Glu Ala Glu Val Ile Gly Asp Phe Asn Gly Arg Asn Gly Ser Asn His
            100                 105                 110

Met Met Glu Lys Asp Gln Phe Gly Val Trp Ser Ile Arg Ile Pro Asp
        115                 120                 125

Val Asp Ser Lys Pro Val Ile Pro His Asn Ser Arg Val Lys Phe Arg
    130                 135                 140

Phe Lys His Gly Asn Gly Val Trp Val Asp Arg Ile Pro Ala Trp Ile
145                 150                 155                 160

Lys Tyr Ala Thr Ala Asp Ala Thr Lys Phe Ala Ala Pro Tyr Asp Gly
                165                 170                 175

Val Tyr Trp Asp Pro Pro Ser Glu Arg Tyr His Phe Lys Tyr Pro
            180                 185                 190

Arg Pro Pro Lys Pro Arg Ala Pro Arg Ile Tyr Glu Ala His Val Gly
        195                 200                 205

Met Ser Ser Ser Glu Pro Arg Val Asn Ser Tyr Arg Glu Phe Ala Asp
    210                 215                 220

Asp Val Leu Pro Arg Ile Lys Ala Asn Asn Tyr Asn Thr Val Gln Leu
225                 230                 235                 240

Met Ala Ile Met Glu His Ser Tyr Tyr Gly Ser Phe Gly Tyr His Val
                245                 250                 255

Thr Asn Phe Phe Ala Val Ser Asn Arg Tyr Gly Asn Pro Glu Asp Leu
            260                 265                 270

Lys Tyr Leu Ile Asp Lys Ala His Ser Leu Gly Leu Gln Val Leu Val
        275                 280                 285

Asp Val Val His Ser His Ala Ser Asn Asn Val Thr Asp Gly Leu Asn
    290                 295                 300

Gly Phe Asp Ile Gly Gln Gly Ser Gln Glu Ser Tyr Phe His Ala Gly
305                 310                 315                 320

Glu Arg Gly Tyr His Lys Leu Trp Asp Ser Arg Leu Phe Asn Tyr Ala
                325                 330                 335

Asn Trp Glu Val Leu Arg Phe Leu Leu Ser Asn Leu Arg Trp Trp Leu
            340                 345                 350

Glu Glu Tyr Asn Phe Asp Gly Phe Arg Phe Asp Gly Ile Thr Ser Met
        355                 360                 365

Leu Tyr Val His His Gly Ile Asn Met Gly Phe Thr Gly Asn Tyr Asn
    370                 375                 380

Glu Tyr Phe Ser Glu Ala Thr Asp Val Asp Ala Val Val Tyr Leu Met
385                 390                 395                 400

Leu Ala Asn Asn Leu Ile His Lys Ile Phe Pro Asp Ala Thr Val Ile
```

|     |     |     |     |     | 405 |     |     |     |     | 410 |     |     |     |     | 415 |     |
| --- | --- | --- | --- | --- | --- | --- | --- | --- | --- | --- | --- | --- | --- | --- | --- | --- |
| Ala | Glu | Asp | Val | Ser | Gly | Met | Pro | Gly | Leu | Ser | Arg | Pro | Val | Ser | Glu |     |
|     |     |     | 420 |     |     |     |     | 425 |     |     |     |     | 430 |     |     |     |

Gly Gly Ile Gly Phe Asp Tyr Arg Leu Ala Met Ala Ile Pro Asp Lys
            435                 440                 445

Trp Ile Asp Tyr Leu Lys Asn Lys Asn Asp Glu Asp Trp Ser Met Lys
        450                 455                 460

Glu Val Thr Ser Ser Leu Thr Asn Arg Arg Tyr Thr Glu Lys Cys Ile
465                 470                 475                 480

Ala Tyr Ala Glu Ser His Asp Gln Ser Ile Val Gly Asp Lys Thr Ile
                485                 490                 495

Ala Phe Leu Leu Met Asn Lys Glu Met Tyr Ser Gly Met Ser Cys Leu
                500                 505                 510

Thr Asp Ala Ser Pro Val Val Asp Ala Gly Ile Ala Leu Asp Lys Met
            515                 520                 525

Ile His Phe Phe His Asn Gly Leu Gly Arg Arg Gly Val Pro Gln Phe
        530                 535                 540

His Gly
545

```
<210> SEQ ID NO 6
<211> LENGTH: 2649
<212> TYPE: DNA
<213> ORGANISM: Solanum tuberosum
<300> PUBLICATION INFORMATION:
<308> DATABASE ACCESSION NUMBER: EMBL / AJ011890
<309> DATABASE ENTRY DATE: 1999-04-07
<300> PUBLICATION INFORMATION:
<302> TITLE: Improvments in or relating to plant starch composition
<308> DATABASE ACCESSION NUMBER: EMBL / A58164
<309> DATABASE ENTRY DATE: 1998-03-05
<310> PATENT DOCUMENT NUMBER: WO 96 34968
<311> PATENT FILING DATE: 1996-05-03
<312> PUBLICATION DATE: 1996-11-07

<400> SEQUENCE: 6
atggtgtata cactctctgg agttcgtttt cctactgttc catcagtgta caaatctaat      60
ggattcagca gtaatggtga tcggaggaat gctaatgttt ctgtattctt gaaaaagcac     120
tctctttcac ggaagatctt ggctgaaaag tcttcttaca attccgaatt ccgaccttct     180
acagttgcag catcggggaa agtccttgtg cctggaaccc agagtgatag ctcctcatcc     240
tcaacagacc aatttgagtt cactgagaca ctcccagaaa attccccagc atcaactgat     300
gtagatagtt caacaatgga acacgctagc cagattaaaa ctgagaacga tgacgttgag     360
ccgtcaagtg atcttacagg aagtgttgaa gagctggatt tgcttcatc actacaacta     420 caagaaggtg gtaaactgga ggagtctaaa acattaaata cttctgaaga gacaattatt     480
gatgaatctg ataggatcag agagaggggc atccctccac ctggacttgg tcagaagatt     540
tatgaaatag acccccttt gacaaactat cgtcaacacc ttgattacag gtattcacag     600
tacaagaaac tgagggaggc aattgacaag tatgagggtg gtttggaagc ctttttctcgt     660 ggttatgaaa aatgggttt cactcgtagt gctacaggta tcacttaccg tgagtgggct     720
cttggtgccc agtcagctgc cctcattgga gatttcaaca attgggacgc aaatgctgac     780
attatgactc ggaatgaatt tggtgtctgg gagattttc tgccaaataa tgtggatggt     840
tctcctgcaa ttcctcatgg gtccagagtg aagatacgta tggacactcc atcaggtgtt     900
aaggattcca ttcctgcttg gatcaactac tctttacagc ttcctgatga aattccatat     960
aatggaatac attatgatcc acccgaagag gagaggtata tcttccaaca cccacggcca    1020
```

```
aagaaaccaa agtcgctgag aatatatgaa tctcatattg gaatgagtag tccggagcct    1080
aaaattaact catacgtgaa ttttagagat gaagttcttc ctcgcataaa aaagctttggg   1140 tacaatgcgc tgcaaattat ggctattcaa gagcattctt attacgctag ttttggttat   1200
catgtcacaa atttttttgc accaagcagc cgttttggaa cgcccgacga ccttaagtct   1260
ttgattgata aagctcatga gctaggaatt gttgttctca tggacattgt tcacagccat   1320
gcatcaaata atactttaga tggactgaac atgtttgact gcaccgatag ttgttacttt   1380
cactctggag ctcgtggtta tcattggatg tgggattccc gcctctttaa ctatggaaac   1440
tgggaggtac ttaggtatct tctctcaaat gcgagatggt ggttggatgc gttcaaattt   1500
gatggattta gatttgatgg tgtgacatca atgatgtata ttcaccacgg attatcggtg   1560
ggattcactg ggaactacga ggaatacttt ggactcgcaa ctgatgtgga tgctgttgtg   1620
tatctgatgc tggtcaacga tcttattcat gggcttttcc cagatgcaat taccattggt   1680
gaagatgtta gcggaatgcc gacatttgt attcccgtcc aagagggggg tgttggcttt    1740
gactatcggc tgcatatggc aattgctgat aaacggattg agttgctcaa gaaacgggat   1800
gaggattgga gagtgggtga tattgttcat acactgacaa atagaagatg gtcggaaaag   1860
tgtgtttcat acgctgaaag tcatgatcaa gctctagtcg gtgataaaac tatagcattc   1920
tggctgatgg acaaggatat gtatgatttt atggctctgg atagaccgtc aacatcatta   1980
atagatcgtg ggatagcatt gcacaagatg attaggcttg taactatggg attaggagga   2040
gaagggtacc taaatttcat gggaaatgaa ttcggccacc ctgagtggat tgatttccct   2100
agggctgaac aacacctctc tgatggctca gtaatccccg gaaaccaatt ccgttatgat   2160
aaatgcagac ggagatttga cctgggagat gcagaatatt taagataccg tgggttgcaa   2220
gaatttgacc ggcctatgca gtatcttgaa gataaatatg agtttatgac ttcagaacac   2280
cagttcatat cacgaaagga tgaaggagat aggatgattg tatttgaaaa aggaaaccta   2340 gttttttgtct ttaattttca ctggacaaaa agctattcag actatcgcat agcctgcctg   2400
aagcctggaa ataccccggt tgccttggac tcagatgatc cacttttttgg tggcttcggg   2460 agaattgatc ataatgccga atatttcacc tttgaaggat ggtatgatga tcgtcctcgt   2520
tcaattatgg tgtatgcacc ttgtaaaaca gcagtggtct atgcactagt agacaaagaa   2580
gaagaagaag aagaagaaga agaagaagaa gtagcagcag tagaagaagt agtagtagaa   2640
gaagaatga                                                            2649
```

<210> SEQ ID NO 7
<211> LENGTH: 882
<212> TYPE: PRT
<213> ORGANISM: Solanum tuberosum

<400> SEQUENCE: 7

```
Met Val Tyr Thr Leu Ser Gly Val Arg Phe Pro Thr Val Pro Ser Val
1               5                   10                  15

Tyr Lys Ser Asn Gly Phe Ser Ser Asn Gly Asp Arg Arg Asn Ala Asn
            20                  25                  30

Val Ser Val Phe Leu Lys Lys His Ser Leu Ser Arg Lys Ile Leu Ala
        35                  40                  45

Glu Lys Ser Ser Tyr Asn Ser Glu Phe Arg Pro Ser Thr Val Ala Ala
    50                  55                  60

Ser Gly Lys Val Leu Val Pro Gly Thr Gln Ser Asp Ser Ser Ser Ser
65                  70                  75                  80
```

```
Ser Thr Asp Gln Phe Glu Phe Thr Glu Thr Ser Pro Glu Asn Ser Pro
                85                  90                  95

Ala Ser Thr Asp Val Asp Ser Ser Thr Met Glu His Ala Ser Gln Ile
            100                 105                 110

Lys Thr Glu Asn Asp Asp Val Glu Pro Ser Ser Asp Leu Thr Gly Ser
        115                 120                 125

Val Glu Glu Leu Asp Phe Ala Ser Ser Leu Gln Leu Gln Glu Gly Gly
    130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Gly Leu
                165                 170                 175

Gly Gln Lys Ile Tyr Glu Ile Asp Pro Leu Leu Thr Asn Tyr Arg Gln
            180                 185                 190

His Leu Asp Tyr Arg Tyr Ser Gln Tyr Lys Lys Leu Arg Glu Ala Ile
        195                 200                 205

Asp Lys Tyr Glu Gly Gly Leu Glu Ala Phe Ser Arg Gly Tyr Glu Lys
    210                 215                 220

Met Gly Phe Thr Arg Ser Ala Thr Gly Ile Thr Tyr Arg Glu Trp Ala
225                 230                 235                 240

Leu Gly Ala Gln Ser Ala Ala Leu Ile Gly Asp Phe Asn Asn Trp Asp
                245                 250                 255

Ala Asn Ala Asp Ile Met Thr Arg Asn Glu Phe Gly Val Trp Glu Ile
            260                 265                 270

Phe Leu Pro Asn Asn Val Asp Gly Ser Pro Ala Ile Pro His Gly Ser
        275                 280                 285

Arg Val Lys Ile Arg Met Asp Thr Pro Ser Gly Val Lys Asp Ser Ile
    290                 295                 300

Pro Ala Trp Ile Asn Tyr Ser Leu Gln Leu Pro Asp Glu Ile Pro Tyr
305                 310                 315                 320

Asn Gly Ile His Tyr Asp Pro Pro Glu Glu Glu Arg Tyr Ile Phe Gln
                325                 330                 335

His Pro Arg Pro Lys Lys Pro Lys Ser Leu Arg Ile Tyr Glu Ser His
            340                 345                 350

Ile Gly Met Ser Ser Pro Glu Pro Lys Ile Asn Ser Tyr Val Asn Phe
        355                 360                 365

Arg Asp Glu Val Leu Pro Arg Ile Lys Lys Leu Gly Tyr Asn Ala Leu
    370                 375                 380

Gln Ile Met Ala Ile Gln Glu His Ser Tyr Tyr Ala Ser Phe Gly Tyr
385                 390                 395                 400

His Val Thr Asn Phe Phe Ala Pro Ser Ser Arg Phe Gly Thr Pro Asp
                405                 410                 415

Asp Leu Lys Ser Leu Ile Asp Lys Ala His Glu Leu Gly Ile Val Val
            420                 425                 430

Leu Met Asp Ile Val His Ser His Ala Ser Asn Asn Thr Leu Asp Gly
        435                 440                 445

Leu Asn Met Phe Asp Cys Thr Asp Ser Cys Tyr Phe His Ser Gly Ala
    450                 455                 460

Arg Gly Tyr His Trp Met Trp Asp Ser Arg Leu Phe Asn Tyr Gly Asn
465                 470                 475                 480

Trp Glu Val Leu Arg Tyr Leu Leu Ser Asn Ala Arg Trp Trp Leu Asp
                485                 490                 495

Ala Phe Lys Phe Asp Gly Phe Arg Phe Asp Gly Val Thr Ser Met Met
            500                 505                 510
```

```
Tyr Ile His His Gly Leu Ser Val Gly Phe Thr Gly Asn Tyr Glu Glu
            515                 520                 525

Tyr Phe Gly Leu Ala Thr Asp Val Asp Ala Val Tyr Leu Met Leu
        530                 535                 540

Val Asn Asp Leu Ile His Gly Leu Phe Pro Asp Ala Ile Thr Ile Gly
545                 550                 555                 560

Glu Asp Val Ser Gly Met Pro Thr Phe Cys Ile Pro Val Gln Glu Gly
                565                 570                 575

Gly Val Gly Phe Asp Tyr Arg Leu His Met Ala Ile Ala Asp Lys Arg
            580                 585                 590

Ile Glu Leu Leu Lys Lys Arg Asp Glu Asp Trp Arg Val Gly Asp Ile
        595                 600                 605

Val His Thr Leu Thr Asn Arg Arg Trp Ser Glu Lys Cys Val Ser Tyr
    610                 615                 620

Ala Glu Ser His Asp Gln Ala Leu Val Gly Asp Lys Thr Ile Ala Phe
625                 630                 635                 640

Trp Leu Met Asp Lys Asp Met Tyr Asp Phe Met Ala Leu Asp Arg Pro
                645                 650                 655

Ser Thr Ser Leu Ile Asp Arg Gly Ile Ala Leu His Lys Met Ile Arg
            660                 665                 670

Leu Val Thr Met Gly Leu Gly Gly Glu Gly Tyr Leu Asn Phe Met Gly
        675                 680                 685

Asn Glu Phe Gly His Pro Glu Trp Ile Asp Phe Pro Arg Ala Glu Gln
    690                 695                 700

His Leu Ser Asp Gly Ser Val Ile Pro Gly Asn Gln Phe Arg Tyr Asp
705                 710                 715                 720

Lys Cys Arg Arg Arg Phe Asp Leu Gly Asp Ala Glu Tyr Leu Arg Tyr
                725                 730                 735

Arg Gly Leu Gln Glu Phe Asp Arg Pro Met Gln Tyr Leu Glu Asp Lys
            740                 745                 750

Tyr Glu Phe Met Thr Ser Glu His Gln Phe Ile Ser Arg Lys Asp Glu
        755                 760                 765

Gly Asp Arg Met Ile Val Phe Glu Lys Gly Asn Leu Val Phe Val Phe
    770                 775                 780

Asn Phe His Trp Thr Lys Ser Tyr Ser Asp Tyr Arg Ile Ala Cys Leu
785                 790                 795                 800

Lys Pro Gly Lys Tyr Pro Val Ala Leu Asp Ser Asp Pro Leu Phe
                805                 810                 815

Gly Gly Phe Gly Arg Ile Asp His Asn Ala Glu Tyr Phe Thr Phe Glu
            820                 825                 830

Gly Trp Tyr Asp Asp Arg Pro Arg Ser Ile Met Val Tyr Ala Pro Cys
        835                 840                 845

Lys Thr Ala Val Val Tyr Ala Leu Val Asp Lys Glu Glu Glu Glu
    850                 855                 860

Glu Glu Glu Glu Glu Glu Val Ala Ala Val Glu Glu Val Val Val Glu
865                 870                 875                 880

Glu Glu

<210> SEQ ID NO 8
<211> LENGTH: 1255
<212> TYPE: DNA
<213> ORGANISM: Solanum tuberosum

<400> SEQUENCE: 8
```

```
attttgtatt cccgttcaag atggggggtgt tggctttgac tatcggctgc atatggcaat      60
tgctgataaa tggattgagt tgctcaagaa acgggatgag gattggagag tgggtgatat     120
tgttcataca ctgacaaata gaagatggtc ggaaaagtgt gtttcatacg ctgaaagtca     180
tgatcaagct ctagtcggtg ataaaactat agcattctgg ctgatggaca aggatatgta     240
tgattttatg gctttggata gaccgtcaac atcattaata gatcgtggga tagcattgca     300
caagatgatt aggcttgtaa ctatgggatt aggaggagaa gggtacctaa atttcatggg     360
aaatgaattc ggccacccctg agtggattga tttccctagg gctgaacaac acctctctga     420
tggctcagta attcccggaa accaattcag ttatgataaa tgcagacgga gatttgacct     480
gggagatgca gaatatttaa gataccgtgg gttgcaagaa tttgaccggg ctatgcagta     540
tcttgaagat aaatatgagt ttatgacttc agaacaccag ttcatatcac gaaaggatga     600
aggagatagg atgattgtat tgaaaaagg aaacctagtt tttgtcttta attttcactg     660
gacaaaaagc tattcagact atcgcatagg ctgcctgaag cctggaaaat acaaggttgc     720
cttggactca gatgatccac ttttggtgg cttcgggaga attgatcata tgccgaatg     780
tttcaccttt gaaggatggt atgatgatcg tcctcgttca attatggtgt atgcacctag     840
tagaacagca gtggtctatg cactagtaga caaagaagaa gaagaagaag aagtagcagt     900
agtagaagaa gtagtagtag aagaagaatg aacgaacttg tgatcgcgtt gaaagatttg     960
aacgctacat agagcttctt gacgtatctg gcaatattgc atcagtcttg gcggaatttc    1020
atgtgacaaa aggtttgcaa ttcttttccac tattagtagt gcaacgatat acgcagagat    1080
gaagtgctga acaaacatat gtaaaatcga tgaatttatg tcgaatgctg ggacgggctt    1140
cagcaggttt tgcttagtga gttctgtaaa ttgtcatctc tttatatgta cagccaacta    1200
gaaatcaatt atgtgagacc taaaatacaa taaccataaa atggaaatag tgctg          1255
```

<210> SEQ ID NO 9
<211> LENGTH: 1004
<212> TYPE: DNA
<213> ORGANISM: Solanum tuberosum

<400> SEQUENCE: 9

```
tcaaactagt cacaaccagt ccatttctgg aggtcgttcc ttcgcagaaa tactgattgg      60
taactccttg gggaaatcct ccatatcaca agagtcatta cttagaggct gctcgttaca     120
caagatgatc agattaatta catctacaat tggtggtcat gcatacctca acttcatggg     180
caatgaattt ggtcacccaa agagagtaga gtttccaatg tcaagcaaca atttctcctt     240
ttcactggct aaccgtcgct gggatctatt ggaagatgtt gtacattatc aattgttctc     300
atttgataag ggtatgatgg acttggataa aaatgggaga atttttgtcca gaggtcttgc     360
caacattcac catgtcaatg atactaccat ggtgatttct tacttgagag gtcccaatct     420
ctttgtgttc aactttcatc ctgtcaattc atatgaaaga tacattatag gtgtggaaga     480
agctggagag tatcaagtca cattaaatac agatgaaaac aagtatggtg gtagaggact     540
acttggccat gatcagaata ttcaaagaac cattagtaga agagctgatg gaatgagatt     600
tgcttggaa gtgcctctgc caagtagaag tgctcaggtc tacaagttga cccgaattct     660
aagagcatga tcactctagt aatcaaagtg cctcatatga tgcacaaaaa ggaaaggttc     720
tacattgccc ttacactgat caatattgac acctttccga ggtgagtttc tgtgattctt     780
gagcagactg ttggctagtc aattatcatg aacttttgcc ttcagcatcc ggatagtcgc     840
ttctcctgtg caatgagggc atggacgaat tttttttggg cttgtcatgg gggtcataag     900
```

| | |
|---|---:|
| catccgccag attaagattt cacaggcctc gagtaaaacc atcacttact ttaaggatac | 960 |
| acaaacacac caacggggtg caggctctga taccttctaa agtg | 1004 |

<210> SEQ ID NO 10
<211> LENGTH: 2096
<212> TYPE: DNA
<213> ORGANISM: Solanum tuberosum

<400> SEQUENCE: 10

| | |
|---|---:|
| aacaatgctc tctctgtcgg attcaattcg aatttcttca ccattgagcg attctcgtct | 60 |
| tagttttcta tctcaaaccg gaagcagaac cagtcgccag cttaaatttg ttcgcagccg | 120 |
| ccgggctcga gtttcgaggt gtagatgctc agcaacggag caaccgccac cgcaacgacg | 180 |
| gaagcaacga ccggagaagt acaaacagtc ggaggaaggg aaaggaatcg atcctgttgg | 240 |
| atttctcagc aaatacggca ttactcataa agcgtttgct caatttcttc gtgaaagata | 300 |
| taaatcattg aaggacttga aggatgaaat attgactcgt catttcagtc tcaaggagat | 360 |
| gtctactggg tatgaattaa tgggtatgca tcgcaacata caacatcgag tggatttctt | 420 |
| ggaatgggct ccaggtgctc gctactgtgc tctgattggt gacttcaatg ggtggtcaac | 480 |
| aactggtaac tgtgccagag agggtcattt tggtcatgac gattatgggt attggtttat | 540 |
| tattcttgaa gataaattac gtgaaggaga agaacctgat aaattgtatt ttcaacagta | 600 |
| caattatgcg gaggactatg gtaaaggtga cacgggtatt accgtcgagg aaatctttaa | 660 |
| aaaagcaaat gatgagtatt gggaacctgg agaagatcgc ttcattaaat cacgttatga | 720 |
| ggtggcagca aagttatatg aggaaatgtt cggaccaaat ggacctcaaa cagaagagga | 780 |
| actagaagca atgcctgatg cagctacacg atacaaaact tggaaagagc aacaaaaaga | 840 |
| ggatccggca agcaatttgc catcgtatga tgtggtagat agtggaaaag aatatgatat | 900 |
| ttacaatatt ataggtgatc ctgaatcgtt taagaaattt cgtatgaaac agcctcctat | 960 |
| tgcttactgg ttagaaacta aaaagggaag gaaaggctgg ttacagaaat atatgcctgc | 1020 |
| tttacctcat ggaagcaaat acagggtgta ttttaacaca ccaaatgggc ctcttgaacg | 1080 |
| agttcctgcg tgggccaatt ttgtcattcc agatgcaggc gggatggcat tagcagtcca | 1140 |
| ttgggaacca cctcctgaat atgcttataa atggaaacac aagctaccag tcaagcctaa | 1200 |
| gtccttgcgc atatatgaat gtcatgttgg catctctggc caggaaccaa agtttcatc | 1260 |
| tttcaatgat tttattagca aggtccttcc gcatgtaaaa gaagctggat acaatgcaat | 1320 |
| acaaattatt ggagttgttg agcacaagga ttatttcact gttggatata gagtgaccaa | 1380 |
| ttttttatgct gttagtagcc gttatggcac accggatgac ttcaagcgct tggttgatga | 1440 |
| agcacatggg cttggactgc ttgtcttttt ggagattgtg cactcttatg cagcagcaga | 1500 |
| tgaaatggtt gggttatctc tttttgatgg agcaaatgat tgctatttcc acactggtaa | 1560 |
| acgtggacac cacaaattct ggggcacacg gatgttcaaa tatggagatc ttgatgttct | 1620 |
| gcactttctt ctttcaaatc tgaactggtg ggtggaggag tatcatgtcg atggcttcca | 1680 |
| ttttcattcg ctctcgtcca tgttgtatac gcataatgga tttgcttcat ttactggtga | 1740 |
| catggatgaa tactgtaacc aatatgttga caaggaggcc ttattgtacc tcatattagc | 1800 |
| aaatgaagta ttcatgctc ttcatcctaa tgtgatcacg attgctgagg atgcaactct | 1860 |
| gtatcctgga ctctgcgatc caacatctca aggtggactg ggctttgatt attttgccaa | 1920 |
| tctttctgcc tcagagatgt ggcttgcatt acttgaaaat actcctgatc atgaatggtg | 1980 |
| catgagtaag attgttagca cattagtggg cgatagacaa aatactgata aaatgctttt | 2040 |

```
gtatgcagaa aatcacaacc agtccatttc tggaggtcgt tccttcgcag aaatac         2096
```

```
<210> SEQ ID NO 11
<211> LENGTH: 3204
<212> TYPE: DNA
<213> ORGANISM: Solanum tuberosum
<220> FEATURE:
<221> NAME/KEY: CDS
<222> LOCATION: (99)..(2804)
<223> OTHER INFORMATION: Solanum tuberosum (cv Desiree) protein involved
      in starch biosynthesis

<400> SEQUENCE: 11
gaattgtaat acgactcact atagggcgaa ttgggccctc tagatgcatg ctcgagcggc         60
cgccagtgtg atggatatct gcagaattcg gcttaaca atg ctc tct ctg tcg gat        116
                                           Met Leu Ser Leu Ser Asp
                                             1               5 tca att cga att tct tca cca ttg agc gat tct cgt ctt agt ttt cta         164
Ser Ile Arg Ile Ser Ser Pro Leu Ser Asp Ser Arg Leu Ser Phe Leu
         10                  15                  20 tct caa acc gga agc aga acc agt cgc cag ctt aaa ttt gtt cgc agc         212
Ser Gln Thr Gly Ser Arg Thr Ser Arg Gln Leu Lys Phe Val Arg Ser
     25                  30                  35 cgc cgg gct cga gtt tcg agg tgt aga tgc tca gca acg gag caa ccg         260
Arg Arg Ala Arg Val Ser Arg Cys Arg Cys Ser Ala Thr Glu Gln Pro
 40                  45                  50 cca ccg caa cga cgg aag caa cga ccg gag aag tac aaa cag tcg gag         308
Pro Pro Gln Arg Arg Lys Gln Arg Pro Glu Lys Tyr Lys Gln Ser Glu
55                  60                  65                  70 gaa gag aaa gga atc gat cct gtt gga ttt ctc agc aaa tac ggc att         356
Glu Glu Lys Gly Ile Asp Pro Val Gly Phe Leu Ser Lys Tyr Gly Ile
                 75                  80                  85 act cat aaa gcg ttt gct caa ttt ctt cgt gaa aga tat aaa tca ttg         404
Thr His Lys Ala Phe Ala Gln Phe Leu Arg Glu Arg Tyr Lys Ser Leu
             90                  95                 100 aag gac ttg aag gat gaa ata ttg act cgt cat ttc agt ctc aag gag         452
Lys Asp Leu Lys Asp Glu Ile Leu Thr Arg His Phe Ser Leu Lys Glu
        105                 110                 115 atg tct act ggg tat gaa tta atg ggt atg cat cgc aac ata caa cat         500
Met Ser Thr Gly Tyr Glu Leu Met Gly Met His Arg Asn Ile Gln His
    120                 125                 130 cga gtg gat ttc ttg gaa tgg gct cca ggt gct cgc tac tgt gct ctg         548
Arg Val Asp Phe Leu Glu Trp Ala Pro Gly Ala Arg Tyr Cys Ala Leu
135                 140                 145                 150 att ggt gac ttc aat ggg tgg tca aca act ggt aac tgt gcc aga gag         596
Ile Gly Asp Phe Asn Gly Trp Ser Thr Thr Gly Asn Cys Ala Arg Glu
                155                 160                 165 ggt cat ttt ggt cat gac gat tat ggg tat tgg ttt att att ctt gaa         644
Gly His Phe Gly His Asp Asp Tyr Gly Tyr Trp Phe Ile Ile Leu Glu
            170                 175                 180 gat aaa tta cgt gaa gga gaa gaa cct gat aaa ttg tat ttt caa cag         692
Asp Lys Leu Arg Glu Gly Glu Glu Pro Asp Lys Leu Tyr Phe Gln Gln
        185                 190                 195 tac aat tat gcg gag gac tat gat aaa ggt gac acg ggt att acc gtc         740
Tyr Asn Tyr Ala Glu Asp Tyr Asp Lys Gly Asp Thr Gly Ile Thr Val
    200                 205                 210 gag gaa atc ttt aaa aaa gca aat gat gag tat tgg gaa cct gga gaa         788
Glu Glu Ile Phe Lys Lys Ala Asn Asp Glu Tyr Trp Glu Pro Gly Glu
215                 220                 225                 230 gat cgc ttc att aaa tca cgt tat gag gtg gca gca aag tta tat gag         836
Asp Arg Phe Ile Lys Ser Arg Tyr Glu Val Ala Ala Lys Leu Tyr Glu
                235                 240                 245
```

```
gaa atg ttc gga cca aat gga cct caa aca gaa gag gaa cta gaa gca        884
Glu Met Phe Gly Pro Asn Gly Pro Gln Thr Glu Glu Glu Leu Glu Ala
    250                 255                 260 atg cct gat gca gct aca cga tac aaa act tgg aaa gag caa caa aaa        932
Met Pro Asp Ala Ala Thr Arg Tyr Lys Thr Trp Lys Glu Gln Gln Lys
265                 270                 275 aag gat ccg gca agc aat ttg cca tcg tat gat gtg gta gat agt gga        980
Lys Asp Pro Ala Ser Asn Leu Pro Ser Tyr Asp Val Val Asp Ser Gly
        280                 285                 290 aaa gaa tat gat att tac aat att ata ggt gat cct gaa tcg ttt aag       1028
Lys Glu Tyr Asp Ile Tyr Asn Ile Ile Gly Asp Pro Glu Ser Phe Lys
295                 300                 305                 310 aaa ttt cgt atg aaa cag cct cct att gct tac tgg tta gaa act aaa       1076
Lys Phe Arg Met Lys Gln Pro Pro Ile Ala Tyr Trp Leu Glu Thr Lys
                315                 320                 325 aag gga agg aaa ggc tgg tta cag aaa tat atg cct gct tta cct cat       1124
Lys Gly Arg Lys Gly Trp Leu Gln Lys Tyr Met Pro Ala Leu Pro His
            330                 335                 340 gga agc aaa cac agg gtg tat ttt aac aca cca aat ggg cct ctt gaa       1172
Gly Ser Lys His Arg Val Tyr Phe Asn Thr Pro Asn Gly Pro Leu Glu
        345                 350                 355 cga gtt cct gcg tgg gcc aat ttt gtc att cca gat gca gac ggg atg       1220
Arg Val Pro Ala Trp Ala Asn Phe Val Ile Pro Asp Ala Asp Gly Met
    360                 365                 370 gca tta gca gtc cat tgg gaa cca cct cct gaa tat gct tat aaa tgg       1268
Ala Leu Ala Val His Trp Glu Pro Pro Pro Glu Tyr Ala Tyr Lys Trp
375                 380                 385                 390 aaa cac aag cta cca gtc aag cct aag tcc ttg cgc ata tat gaa tgt       1316
Lys His Lys Leu Pro Val Lys Pro Lys Ser Leu Arg Ile Tyr Glu Cys
                395                 400                 405 cat gtt ggc atc tct ggc cag gaa cca aaa gtt tca tct ttc aat gat       1364
His Val Gly Ile Ser Gly Gln Glu Pro Lys Val Ser Ser Phe Asn Asp
            410                 415                 420 ttt att agc aag gtc ctt ccg cat gta aaa gaa gct gga tac aat gca       1412
Phe Ile Ser Lys Val Leu Pro His Val Lys Glu Ala Gly Tyr Asn Ala
        425                 430                 435 acg caa att att gga gtt gtt gag cac aag gat tat ttc act gtt gga       1460
Thr Gln Ile Ile Gly Val Val Glu His Lys Asp Tyr Phe Thr Val Gly
    440                 445                 450 tat aga gtg acc aat ttt tat gct gtt agt agc cgt tat ggc aca ccg       1508
Tyr Arg Val Thr Asn Phe Tyr Ala Val Ser Ser Arg Tyr Gly Thr Pro
455                 460                 465                 470 gat gac ttc aag cgc ttg gtt gat gaa gca cat ggg ctt gga ctg ctt       1556
Asp Asp Phe Lys Arg Leu Val Asp Glu Ala His Gly Leu Gly Leu Leu
                475                 480                 485 gtc ttt ttg gag att gtg cac tcc tat gca gca gca gat gaa atg gtt       1604
Val Phe Leu Glu Ile Val His Ser Tyr Ala Ala Ala Asp Glu Met Val
            490                 495                 500 ggg tta tct ctt ttt gat gga gca aat gat tgc tat ttc cac act ggt       1652
Gly Leu Ser Leu Phe Asp Gly Ala Asn Asp Cys Tyr Phe His Thr Gly
        505                 510                 515 aaa cgt gga cac cac aaa ttc tgg ggc aca cgg atg ttc aaa tat gga       1700
Lys Arg Gly His His Lys Phe Trp Gly Thr Arg Met Phe Lys Tyr Gly
    520                 525                 530 gat cct gat gtt ctg cac ttt ctt ctt tca aat ctg aac tgg tgg gtg       1748
Asp Pro Asp Val Leu His Phe Leu Leu Ser Asn Leu Asn Trp Trp Val
535                 540                 545                 550 gag gag tat cat gtc gat ggc ttc cat ttt cat tcg ctc tcg tcc atg       1796
Glu Glu Tyr His Val Asp Gly Phe His Phe His Ser Leu Ser Ser Met
                555                 560                 565
```

| | | | | | | | | | | | | | | | | |
|---|---|---|---|---|---|---|---|---|---|---|---|---|---|---|---|---|
| ttg | tat | acg | cat | aat | gga | ttt | gct | tca | ttt | act | ggt | gac | atg | gat | gaa | 1844 |
| Leu | Tyr | Thr | His | Asn | Gly | Phe | Ala | Ser | Phe | Thr | Gly | Asp | Met | Asp | Glu | |
| | | | 570 | | | | 575 | | | | | 580 | | | | |
| tac | tgt | aac | caa | tat | gtt | gac | aag | gag | gcc | tta | ttg | tac | ctc | ata | tta | 1892 |
| Tyr | Cys | Asn | Gln | Tyr | Val | Asp | Lys | Glu | Ala | Leu | Leu | Tyr | Leu | Ile | Leu | |
| | | 585 | | | | 590 | | | | | 595 | | | | | |
| gca | aat | gaa | gta | tta | cat | gct | ctt | cat | cct | aat | gtg | atc | acg | att | gct | 1940 |
| Ala | Asn | Glu | Val | Leu | His | Ala | Leu | His | Pro | Asn | Val | Ile | Thr | Ile | Ala | |
| 600 | | | | | 605 | | | | | 610 | | | | | | |
| gtg | gat | gca | act | ctg | tat | cct | gga | ctc | tgc | gat | cca | aca | tct | caa | ggt | 1988 |
| Val | Asp | Ala | Thr | Leu | Tyr | Pro | Gly | Leu | Cys | Asp | Pro | Thr | Ser | Gln | Gly | |
| 615 | | | | | 620 | | | | | 625 | | | | | 630 | |
| gga | ctg | ggc | ttt | gat | tat | ttt | gcc | aat | ctt | tct | gcc | tca | gag | atg | tgg | 2036 |
| Gly | Leu | Gly | Phe | Asp | Tyr | Phe | Ala | Asn | Leu | Ser | Ala | Ser | Glu | Met | Trp | |
| | | | | 635 | | | | 640 | | | | | 645 | | | |
| ctt | gca | tta | ctt | gaa | aat | act | cct | gat | cat | gaa | tgg | tgc | atg | agt | aag | 2084 |
| Leu | Ala | Leu | Leu | Glu | Asn | Thr | Pro | Asp | His | Glu | Trp | Cys | Met | Ser | Lys | |
| | | | 650 | | | | | 655 | | | | | 660 | | | |
| att | gtt | agc | aca | tta | gtg | ggc | gat | aga | caa | aat | act | gat | aaa | atg | ctt | 2132 |
| Ile | Val | Ser | Thr | Leu | Val | Gly | Asp | Arg | Gln | Asn | Thr | Asp | Lys | Met | Leu | |
| | | | 665 | | | | | 670 | | | | | 675 | | | |
| ttg | tat | gca | gaa | aat | cac | aac | cag | tcc | att | tct | gga | ggt | cgt | tcc | ttc | 2180 |
| Leu | Tyr | Ala | Glu | Asn | His | Asn | Gln | Ser | Ile | Ser | Gly | Gly | Arg | Ser | Phe | |
| | 680 | | | | | 685 | | | | | 690 | | | | | |
| gca | gaa | ata | ctg | att | ggt | aac | tcc | ttg | ggg | aaa | tct | tcc | ata | tca | caa | 2228 |
| Ala | Glu | Ile | Leu | Ile | Gly | Asn | Ser | Leu | Gly | Lys | Ser | Ser | Ile | Ser | Gln | |
| 695 | | | | | 700 | | | | | 705 | | | | | 710 | |
| gag | tca | tta | ctt | aga | ggc | tgc | tcg | tta | cac | aag | atg | atc | aga | tta | att | 2276 |
| Glu | Ser | Leu | Leu | Arg | Gly | Cys | Ser | Leu | His | Lys | Met | Ile | Arg | Leu | Ile | |
| | | | | 715 | | | | | 720 | | | | | 725 | | |
| aca | tct | aca | att | ggt | ggt | cat | gca | tac | ctc | aac | ttc | atg | ggc | aat | gaa | 2324 |
| Thr | Ser | Thr | Ile | Gly | Gly | His | Ala | Tyr | Leu | Asn | Phe | Met | Gly | Asn | Glu | |
| | | | 730 | | | | | 735 | | | | | 740 | | | |
| ttt | ggt | cac | cca | aag | aga | gta | gag | ttt | cca | atg | tca | agc | aac | aat | ttc | 2372 |
| Phe | Gly | His | Pro | Lys | Arg | Val | Glu | Phe | Pro | Met | Ser | Ser | Asn | Asn | Phe | |
| | | 745 | | | | | 750 | | | | | 755 | | | | |
| tcc | ttt | tca | ctg | gct | aac | cgt | cgc | tgg | gat | cta | ttg | gaa | gat | gtt | gta | 2420 |
| Ser | Phe | Ser | Leu | Ala | Asn | Arg | Arg | Trp | Asp | Leu | Leu | Glu | Asp | Val | Val | |
| | 760 | | | | | 765 | | | | | 770 | | | | | |
| cat | tat | caa | tta | ttc | tca | ttt | gat | aag | gat | atg | atg | gac | ttg | gat | aaa | 2468 |
| His | Tyr | Gln | Leu | Phe | Ser | Phe | Asp | Lys | Asp | Met | Met | Asp | Leu | Asp | Lys | |
| 775 | | | | | 780 | | | | | 785 | | | | | 790 | |
| aat | ggg | aga | att | ttg | tcc | aga | ggt | ctt | gcc | aac | att | cac | cat | gtc | aat | 2516 |
| Asn | Gly | Arg | Ile | Leu | Ser | Arg | Gly | Leu | Ala | Asn | Ile | His | His | Val | Asn | |
| | | | | 795 | | | | | 800 | | | | | 805 | | |
| gat | act | acc | atg | gtg | att | tct | tac | ttg | aga | ggt | ccc | aat | ctc | ttt | gtg | 2564 |
| Asp | Thr | Thr | Met | Val | Ile | Ser | Tyr | Leu | Arg | Gly | Pro | Asn | Leu | Phe | Val | |
| | | | 810 | | | | | 815 | | | | | 820 | | | |
| ttc | aac | ttt | cat | cct | gtc | aat | tca | tat | gaa | aga | tac | att | ata | ggt | gtg | 2612 |
| Phe | Asn | Phe | His | Pro | Val | Asn | Ser | Tyr | Glu | Arg | Tyr | Ile | Ile | Gly | Val | |
| | | 825 | | | | | 830 | | | | | 835 | | | | |
| gaa | gaa | gct | gga | gag | tat | caa | gtc | aca | tta | aat | aca | gat | gaa | aac | aag | 2660 |
| Glu | Glu | Ala | Gly | Glu | Tyr | Gln | Val | Thr | Leu | Asn | Thr | Asp | Glu | Asn | Lys | |
| | 840 | | | | | 845 | | | | | 850 | | | | | |
| tat | ggt | ggt | aga | gga | cta | ctt | ggc | cat | gat | cag | aat | act | caa | aga | acc | 2708 |
| Tyr | Gly | Gly | Arg | Gly | Leu | Leu | Gly | His | Asp | Gln | Asn | Thr | Gln | Arg | Thr | |
| 855 | | | | | 860 | | | | | 865 | | | | | 870 | |
| att | agt | aga | aga | gct | gat | gga | atg | aga | ttt | tgc | ttg | gaa | gta | cct | ctg | 2756 |
| Ile | Ser | Arg | Arg | Ala | Asp | Gly | Met | Arg | Phe | Cys | Leu | Glu | Val | Pro | Leu | |
| | | | | 875 | | | | | 880 | | | | | 885 | | |

-continued

```
cca agt aga agt gct cag gtc tac aag ttg acc cga att cta aga gca    2804
Pro Ser Arg Ser Ala Gln Val Tyr Lys Leu Thr Arg Ile Leu Arg Ala
            890                 895                 900 tgatcactct agcaatcaaa gtgcctcata tgatcacaca aaagggaagg ttctacattg    2864
cccttatact gaccaatatt gtggcctttc gaggtgagt ttctgtgatt cttgagcaca    2924
ggctgttggc tagtcagtta tcatgaactt ttgccttcag catctggata agcgcttctc    2984
ctgtgcaatg agggcatgga cgaaattttt ttggttcgtc atgggagtca aaagcatctg    3044
ccagattaag atttcacagg cctcgagtaa aaccatcact tacttaggat acacaaacac    3104
atcaacgggg tgcaggctct gataccttct aaagtgaagc cgaattccag cacactggcg    3164
gccgttacta gtggatccga gctcggtacc aagcttggcg                         3204
```

<210> SEQ ID NO 12
<211> LENGTH: 902
<212> TYPE: PRT
<213> ORGANISM: Solanum tuberosum

<400> SEQUENCE: 12

```
Met Leu Ser Leu Ser Asp Ser Ile Arg Ile Ser Ser Pro Leu Ser Asp
1               5                   10                  15

Ser Arg Leu Ser Phe Leu Ser Gln Thr Gly Ser Arg Thr Ser Arg Gln
            20                  25                  30

Leu Lys Phe Val Arg Ser Arg Arg Ala Arg Val Ser Arg Cys Arg Cys
        35                  40                  45

Ser Ala Thr Glu Gln Pro Pro Gln Arg Arg Lys Gln Arg Pro Glu
    50                  55                  60

Lys Tyr Lys Gln Ser Glu Glu Lys Gly Ile Asp Pro Val Gly Phe
65              70                  75                  80

Leu Ser Lys Tyr Gly Ile Thr His Lys Ala Phe Ala Gln Phe Leu Arg
                85                  90                  95

Glu Arg Tyr Lys Ser Leu Lys Asp Leu Lys Asp Glu Ile Leu Thr Arg
            100                 105                 110

His Phe Ser Leu Lys Glu Met Ser Thr Gly Tyr Glu Leu Met Gly Met
        115                 120                 125

His Arg Asn Ile Gln His Arg Val Asp Phe Leu Glu Trp Ala Pro Gly
    130                 135                 140

Ala Arg Tyr Cys Ala Leu Ile Gly Asp Phe Asn Gly Trp Ser Thr Thr
145                 150                 155                 160

Gly Asn Cys Ala Arg Glu Gly His Phe Gly His Asp Asp Tyr Gly Tyr
                165                 170                 175

Trp Phe Ile Ile Leu Glu Asp Lys Leu Arg Glu Gly Glu Pro Asp
            180                 185                 190

Lys Leu Tyr Phe Gln Gln Tyr Asn Tyr Ala Glu Asp Tyr Asp Lys Gly
        195                 200                 205

Asp Thr Gly Ile Thr Val Glu Glu Ile Phe Lys Lys Ala Asn Asp Glu
    210                 215                 220

Tyr Trp Glu Pro Gly Glu Asp Arg Phe Ile Lys Ser Arg Tyr Glu Val
225                 230                 235                 240

Ala Ala Lys Leu Tyr Glu Glu Met Phe Gly Pro Asn Gly Pro Gln Thr
                245                 250                 255

Glu Glu Glu Leu Glu Ala Met Pro Asp Ala Ala Thr Arg Tyr Lys Thr
            260                 265                 270

Trp Lys Glu Gln Gln Lys Lys Asp Pro Ala Ser Asn Leu Pro Ser Tyr
        275                 280                 285
```

```
Asp Val Val Asp Ser Gly Lys Glu Tyr Asp Ile Tyr Asn Ile Ile Gly
    290                 295                 300

Asp Pro Glu Ser Phe Lys Lys Phe Arg Met Lys Gln Pro Pro Ile Ala
305                 310                 315                 320

Tyr Trp Leu Glu Thr Lys Lys Gly Arg Lys Gly Trp Leu Gln Lys Tyr
                325                 330                 335

Met Pro Ala Leu Pro His Gly Ser Lys His Arg Val Tyr Phe Asn Thr
        340                 345                 350

Pro Asn Gly Pro Leu Glu Arg Val Pro Ala Trp Ala Asn Phe Val Ile
            355                 360                 365

Pro Asp Ala Asp Gly Met Ala Leu Ala Val His Trp Glu Pro Pro
370                 375                 380

Glu Tyr Ala Tyr Lys Trp Lys His Lys Leu Pro Val Lys Pro Lys Ser
385                 390                 395                 400

Leu Arg Ile Tyr Glu Cys His Val Gly Ile Ser Gly Gln Glu Pro Lys
                405                 410                 415

Val Ser Ser Phe Asn Asp Phe Ile Ser Lys Val Leu Pro His Val Lys
            420                 425                 430

Glu Ala Gly Tyr Asn Ala Thr Gln Ile Ile Gly Val Glu His Lys
                435                 440                 445

Asp Tyr Phe Thr Val Gly Tyr Arg Val Thr Asn Phe Tyr Ala Val Ser
    450                 455                 460

Ser Arg Tyr Gly Thr Pro Asp Asp Phe Lys Arg Leu Val Asp Glu Ala
465                 470                 475                 480

His Gly Leu Gly Leu Leu Val Phe Leu Glu Ile Val His Ser Tyr Ala
                485                 490                 495

Ala Ala Asp Glu Met Val Gly Leu Ser Leu Phe Asp Gly Ala Asn Asp
            500                 505                 510

Cys Tyr Phe His Thr Gly Lys Arg Gly His His Lys Phe Trp Gly Thr
                515                 520                 525

Arg Met Phe Lys Tyr Gly Asp Pro Asp Val Leu His Phe Leu Leu Ser
    530                 535                 540

Asn Leu Asn Trp Trp Val Glu Glu Tyr His Val Asp Gly Phe His Phe
545                 550                 555                 560

His Ser Leu Ser Ser Met Leu Tyr Thr His Asn Gly Phe Ala Ser Phe
                565                 570                 575

Thr Gly Asp Met Asp Glu Tyr Cys Asn Gln Tyr Val Asp Lys Glu Ala
            580                 585                 590

Leu Leu Tyr Leu Ile Leu Ala Asn Glu Val Leu His Ala Leu His Pro
                595                 600                 605

Asn Val Ile Thr Ile Ala Val Asp Ala Thr Leu Tyr Pro Gly Leu Cys
    610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
            660                 665                 670

Asn Thr Asp Lys Met Leu Leu Tyr Ala Glu Asn His Asn Gln Ser Ile
            675                 680                 685

Ser Gly Gly Arg Ser Phe Ala Glu Ile Leu Ile Gly Asn Ser Leu Gly
    690                 695                 700

Lys Ser Ser Ile Ser Gln Glu Ser Leu Leu Arg Gly Cys Ser Leu His
```

```
                705                 710                 715                 720
Lys Met Ile Arg Leu Ile Thr Ser Thr Ile Gly Gly His Ala Tyr Leu
                    725                 730                 735

Asn Phe Met Gly Asn Glu Phe Gly His Pro Lys Arg Val Glu Phe Pro
                    740                 745                 750

Met Ser Ser Asn Asn Phe Ser Phe Ser Leu Ala Asn Arg Arg Trp Asp
                    755                 760                 765

Leu Leu Glu Asp Val Val His Tyr Gln Leu Phe Ser Phe Asp Lys Asp
                    770                 775                 780

Met Met Asp Leu Asp Lys Asn Gly Arg Ile Leu Ser Arg Gly Leu Ala
785                 790                 795                 800

Asn Ile His His Val Asn Asp Thr Thr Met Val Ile Ser Tyr Leu Arg
                    805                 810                 815

Gly Pro Asn Leu Phe Val Phe Asn Phe His Pro Val Asn Ser Tyr Glu
                    820                 825                 830

Arg Tyr Ile Ile Gly Val Glu Glu Ala Gly Glu Tyr Gln Val Thr Leu
                    835                 840                 845

Asn Thr Asp Glu Asn Lys Tyr Gly Gly Arg Gly Leu Leu Gly His Asp
                    850                 855                 860

Gln Asn Thr Gln Arg Thr Ile Ser Arg Arg Ala Asp Gly Met Arg Phe
865                 870                 875                 880

Cys Leu Glu Val Pro Leu Pro Ser Arg Ser Ala Gln Val Tyr Lys Leu
                    885                 890                 895

Thr Arg Ile Leu Arg Ala
                900

<210> SEQ ID NO 13
<211> LENGTH: 3047
<212> TYPE: DNA
<213> ORGANISM: Solanum tuberosum
<220> FEATURE:
<221> NAME/KEY: CDS
<222> LOCATION: (5)..(2710)
<223> OTHER INFORMATION: Solanum tuberosum (cv Desiree) protein involved
      in starch biosynthesis

<400> SEQUENCE: 13 aaca atg ctc tct ctg tcg gat tca att cga att tct tca cca ttg agc        49
     Met Leu Ser Leu Ser Asp Ser Ile Arg Ile Ser Ser Pro Leu Ser
     1               5                   10                  15 gat tct cgt ctt agt ttt cta tct caa acc gga agc aga acc agt cgc        97
Asp Ser Arg Leu Ser Phe Leu Ser Gln Thr Gly Ser Arg Thr Ser Arg
                20                  25                  30 cag ctt aaa ttt gtt cgc agc cgc cgg gct cga gtt tcg agg tgt aga       145
Gln Leu Lys Phe Val Arg Ser Arg Arg Ala Arg Val Ser Arg Cys Arg
            35                  40                  45 tgc tca gca acg gag caa ccg cca ccg caa cga cgg aag caa cga ccg       193
Cys Ser Ala Thr Glu Gln Pro Pro Pro Gln Arg Arg Lys Gln Arg Pro
        50                  55                  60 gag aag tac aaa cag tcg gag gaa ggg aaa gga atc gat cct gtt gga       241
Glu Lys Tyr Lys Gln Ser Glu Glu Gly Lys Gly Ile Asp Pro Val Gly
    65                  70                  75 ttt ctc agc aaa tac ggc att act cat aaa gcg ttt gct caa ttt ctt       289
Phe Leu Ser Lys Tyr Gly Ile Thr His Lys Ala Phe Ala Gln Phe Leu
80                  85                  90                  95 cgt gaa aga tat aaa tca ttg aag gac ttg aag gat gaa ata ttg act       337
Arg Glu Arg Tyr Lys Ser Leu Lys Asp Leu Lys Asp Glu Ile Leu Thr
                100                 105                 110 cgt cat ttc agt ctc aag gag atg tct act ggg tat gaa tta atg ggt       385
```

```
                    -continued

Arg His Phe Ser Leu Lys Glu Met Ser Thr Gly Tyr Glu Leu Met Gly
            115                 120                 125 atg cat cgc aac ata caa cat cga gtg gat ttc ttg gaa tgg gct cca       433
Met His Arg Asn Ile Gln His Arg Val Asp Phe Leu Glu Trp Ala Pro
        130                 135                 140 ggt gct cgc tac tgt gct ctg att ggt gac ttc aat ggg tgg tca aca       481
Gly Ala Arg Tyr Cys Ala Leu Ile Gly Asp Phe Asn Gly Trp Ser Thr
145                 150                 155 act ggt aac tgt gcc aga gag ggt cat ttt ggt cat gac gat tat ggg       529
Thr Gly Asn Cys Ala Arg Glu Gly His Phe Gly His Asp Asp Tyr Gly
160                 165                 170                 175 tat tgg ttt att att ctt gaa gat aaa tta cgt gaa gga gaa gaa cct       577
Tyr Trp Phe Ile Ile Leu Glu Asp Lys Leu Arg Glu Gly Glu Glu Pro
                180                 185                 190 gat aaa ttg tat ttt caa cag tac aat tat gcg gag gac tat ggt aaa       625
Asp Lys Leu Tyr Phe Gln Gln Tyr Asn Tyr Ala Glu Asp Tyr Gly Lys
            195                 200                 205 ggt gac acg ggt att acc gtc gag gaa atc ttt aaa aaa gca aat gat       673
Gly Asp Thr Gly Ile Thr Val Glu Glu Ile Phe Lys Lys Ala Asn Asp
        210                 215                 220 gag tat tgg gaa cct gga gaa gat cgc ttc att aaa tca cgt tat gag       721
Glu Tyr Trp Glu Pro Gly Glu Asp Arg Phe Ile Lys Ser Arg Tyr Glu
225                 230                 235 gtg gca gca aag tta tat gag gaa atg ttc gga cca aat gga cct caa       769
Val Ala Ala Lys Leu Tyr Glu Glu Met Phe Gly Pro Asn Gly Pro Gln
240                 245                 250                 255 aca gaa gag gaa cta gaa gca atg cct gat gca gct aca cga tac aaa       817
Thr Glu Glu Glu Leu Glu Ala Met Pro Asp Ala Ala Thr Arg Tyr Lys
                260                 265                 270 act tgg aaa gag caa caa aaa gag gat ccg gca agc aat ttg cca tcg       865
Thr Trp Lys Glu Gln Gln Lys Glu Asp Pro Ala Ser Asn Leu Pro Ser
            275                 280                 285 tat gat gtg gta gat agt gga aaa gaa tat gat att tac aat att ata       913
Tyr Asp Val Val Asp Ser Gly Lys Glu Tyr Asp Ile Tyr Asn Ile Ile
        290                 295                 300 ggt gat cct gaa tcg ttt aag aaa ttt cgt atg aaa cag cct cct att       961
Gly Asp Pro Glu Ser Phe Lys Lys Phe Arg Met Lys Gln Pro Pro Ile
305                 310                 315 gct tac tgg tta gaa act aaa aag gga agg aaa ggc tgg tta cag aaa      1009
Ala Tyr Trp Leu Glu Thr Lys Lys Gly Arg Lys Gly Trp Leu Gln Lys
320                 325                 330                 335 tat atg cct gct tta cct cat gga agc aaa tac agg gtg tat ttt aac      1057
Tyr Met Pro Ala Leu Pro His Gly Ser Lys Tyr Arg Val Tyr Phe Asn
                340                 345                 350 aca cca aat ggg cct ctt gaa cga gtt cct gcg tgg gcc aat ttt gtc      1105
Thr Pro Asn Gly Pro Leu Glu Arg Val Pro Ala Trp Ala Asn Phe Val
            355                 360                 365 att cca gat gca ggc ggg atg gca tta gca gtc cat tgg gaa cca cct      1153
Ile Pro Asp Ala Gly Gly Met Ala Leu Ala Val His Trp Glu Pro Pro
        370                 375                 380 cct gaa tat gct tat aaa tgg aaa cac aag cta cca gtc aag cct aag      1201
Pro Glu Tyr Ala Tyr Lys Trp Lys His Lys Leu Pro Val Lys Pro Lys
385                 390                 395 tcc ttg cgc ata tat gaa tgt cat gtt ggc atc tct ggc cag gaa cca      1249
Ser Leu Arg Ile Tyr Glu Cys His Val Gly Ile Ser Gly Gln Glu Pro
400                 405                 410                 415 aaa gtt tca tct ttc aat gat ttt att agc aag gtc ctt ccg cat gta      1297
Lys Val Ser Ser Phe Asn Asp Phe Ile Ser Lys Val Leu Pro His Val
                420                 425                 430 aaa gaa gct gga tac aat gca ata caa att att gga gtt gtt gag cac      1345
Lys Glu Ala Gly Tyr Asn Ala Ile Gln Ile Ile Gly Val Val Glu His
```

```
                    Lys Glu Ala Gly Tyr Asn Ala Ile Gln Ile Ile Gly Val Val Glu His
                                    435                 440                 445 aag gat tat ttc act gtt gga tat aga gtg acc aat ttt tat gct gtt         1393
Lys Asp Tyr Phe Thr Val Gly Tyr Arg Val Thr Asn Phe Tyr Ala Val
            450                 455                 460 agt agc cgt tat ggc aca ccg gat gac ttc aag cgc ttg gtt gat gaa         1441
Ser Ser Arg Tyr Gly Thr Pro Asp Asp Phe Lys Arg Leu Val Asp Glu
    465                 470                 475 gca cat ggg ctt gga ctg ctt gtc ttt ttg gag att gtg cac tct tat         1489
Ala His Gly Leu Gly Leu Leu Val Phe Leu Glu Ile Val His Ser Tyr
480                 485                 490                 495 gca gca gca gat gaa atg gtt ggg tta tct ctt ttt gat gga gca aat         1537
Ala Ala Ala Asp Glu Met Val Gly Leu Ser Leu Phe Asp Gly Ala Asn
                500                 505                 510 gat tgc tat ttc cac act ggt aaa cgt gga cac cac aaa ttc tgg ggc         1585
Asp Cys Tyr Phe His Thr Gly Lys Arg Gly His His Lys Phe Trp Gly
            515                 520                 525 aca cgg atg ttc aaa tat gga gat ctt gat gtt ctg cac ttt ctt ctt         1633
Thr Arg Met Phe Lys Tyr Gly Asp Leu Asp Val Leu His Phe Leu Leu
    530                 535                 540 tca aat ctg aac tgg tgg gtg gag gag tat cat gtc gat ggc ttc cat         1681
Ser Asn Leu Asn Trp Trp Val Glu Glu Tyr His Val Asp Gly Phe His
545                 550                 555 ttt cat tcg ctc tcg tcc atg ttg tat acg cat aat gga ttt gct tca         1729
Phe His Ser Leu Ser Ser Met Leu Tyr Thr His Asn Gly Phe Ala Ser
560                 565                 570                 575 ttt act ggt gac atg gat gaa tac tgt aac caa tat gtt gac aag gag         1777
Phe Thr Gly Asp Met Asp Glu Tyr Cys Asn Gln Tyr Val Asp Lys Glu
                580                 585                 590 gcc tta ttg tac ctc ata tta gca aat gaa gta tta cat gct ctt cat         1825
Ala Leu Leu Tyr Leu Ile Leu Ala Asn Glu Val Leu His Ala Leu His
            595                 600                 605 cct aat gtg atc acg att gct gag gat gca act ctg tat cct gga ctc         1873
Pro Asn Val Ile Thr Ile Ala Glu Asp Ala Thr Leu Tyr Pro Gly Leu
    610                 615                 620 tgc gat cca aca tct caa ggt gga ctg ggc ttt gat tat ttt gcc aat         1921
Cys Asp Pro Thr Ser Gln Gly Gly Leu Gly Phe Asp Tyr Phe Ala Asn
625                 630                 635 ctt tct gcc tca gag atg tgg ctt gca tta ctt gaa aat act cct gat         1969
Leu Ser Ala Ser Glu Met Trp Leu Ala Leu Leu Glu Asn Thr Pro Asp
640                 645                 650                 655 cat gaa tgg tgc atg agt aag att gtt agc aca tta gtg ggc gat aga         2017
His Glu Trp Cys Met Ser Lys Ile Val Ser Thr Leu Val Gly Asp Arg
                660                 665                 670 caa aat act gat aaa atg ctt ttg tat gca gaa aat cac aac cag tcc         2065
Gln Asn Thr Asp Lys Met Leu Leu Tyr Ala Glu Asn His Asn Gln Ser
            675                 680                 685 att tct gga ggt cgt tcc ttc gca gaa ata ctg att ggt aac tcc ttg         2113
Ile Ser Gly Gly Arg Ser Phe Ala Glu Ile Leu Ile Gly Asn Ser Leu
    690                 695                 700 ggg aaa tcc tcc ata tca caa gag tca tta ctt aga ggc tgc tcg tta         2161
Gly Lys Ser Ser Ile Ser Gln Glu Ser Leu Leu Arg Gly Cys Ser Leu
705                 710                 715 cac aag atg atc aga tta att aca tct aca att ggt ggt cat gca tac         2209
His Lys Met Ile Arg Leu Ile Thr Ser Thr Ile Gly Gly His Ala Tyr
720                 725                 730                 735 ctc aac ttc atg ggc aat gaa ttt ggt cac cca aag aga gta gag ttt         2257
Leu Asn Phe Met Gly Asn Glu Phe Gly His Pro Lys Arg Val Glu Phe
                740                 745                 750 cca atg tca agc aac aat ttc tcc ttt tca ctg gct aac cgt cgc tgg         2305
```

```
       Pro Met Ser Ser Asn Asn Phe Ser Phe Ser Leu Ala Asn Arg Arg Trp
               755                 760                 765 gat cta ttg gaa gat gtt gta cat tat caa ttg ttc tca ttt gat aag            2353
Asp Leu Leu Glu Asp Val Val His Tyr Gln Leu Phe Ser Phe Asp Lys
       770                 775                 780 ggt atg atg gac ttg gat aaa aat ggg aga att ttg tcc aga ggt ctt            2401
Gly Met Met Asp Leu Asp Lys Asn Gly Arg Ile Leu Ser Arg Gly Leu
       785                 790                 795 gcc aac att cac cat gtc aat gat act acc atg gtg att tct tac ttg            2449
Ala Asn Ile His His Val Asn Asp Thr Thr Met Val Ile Ser Tyr Leu
800                 805                 810                 815 aga ggt ccc aat ctc ttt gtg ttc aac ttt cat cct gtc aat tca tat            2497
Arg Gly Pro Asn Leu Phe Val Phe Asn Phe His Pro Val Asn Ser Tyr
               820                 825                 830 gaa aga tac att ata ggt gtg gaa gaa gct gga gag tat caa gtc aca            2545
Glu Arg Tyr Ile Ile Gly Val Glu Glu Ala Gly Glu Tyr Gln Val Thr
       835                 840                 845 tta aat aca gat gaa aac aag tat ggt ggt aga gga cta ctt ggc cat            2593
Leu Asn Thr Asp Glu Asn Lys Tyr Gly Gly Arg Gly Leu Leu Gly His
       850                 855                 860 gat cag aat att caa aga acc att agt aga aga gct gat gga atg aga            2641
Asp Gln Asn Ile Gln Arg Thr Ile Ser Arg Arg Ala Asp Gly Met Arg
865                 870                 875 ttt tgc ttg gaa gtg cct ctg cca agt aga agt gct cag gtc tac aag            2689
Phe Cys Leu Glu Val Pro Leu Pro Ser Arg Ser Ala Gln Val Tyr Lys
880                 885                 890                 895 ttg acc cga att cta aga gca tgatcactct agtaatcaaa gtgcctcata              2740
Leu Thr Arg Ile Leu Arg Ala
                       900 tgatgacaca aaggaaagg ttctacattg cccttacact gatcaatatt gacacctttc           2800 cgaggtgagt ttctgtgatt cttgagcaga ctgttggcta gtcaattatc atgaactttt          2860 gccttcagca tccggatagt cgcttctcct gtgcaatgag ggcatggacg aattttttt           2920 tggcttgtca tgggggtcat aagcatccgc cagattaaga tttcacaggc ctcgagtaaa          2980 accatcactt actttaagga tacacaaaca caccaacggg gtgcaggctc tgatacttc           3040 taaagtg                                                                   3047
```

<210> SEQ ID NO 14
<211> LENGTH: 902
<212> TYPE: PRT
<213> ORGANISM: Solanum tuberosum

<400> SEQUENCE: 14

```
Met Leu Ser Leu Ser Asp Ser Ile Arg Ile Ser Ser Pro Leu Ser Asp
1               5                   10                  15

Ser Arg Leu Ser Phe Leu Ser Gln Thr Gly Ser Arg Thr Ser Arg Gln
           20                  25                  30

Leu Lys Phe Val Arg Ser Arg Ala Arg Val Ser Arg Cys Arg Cys
       35                  40                  45

Ser Ala Thr Glu Gln Pro Pro Pro Gln Arg Arg Lys Gln Arg Pro Glu
50                  55                  60

Lys Tyr Lys Gln Ser Glu Glu Gly Lys Gly Ile Asp Pro Val Gly Phe
65                  70                  75                  80

Leu Ser Lys Tyr Gly Ile Thr His Lys Ala Phe Ala Gln Phe Leu Arg
               85                  90                  95

Glu Arg Tyr Lys Ser Leu Lys Asp Leu Lys Asp Glu Ile Leu Thr Arg
               100                 105                 110
```

```
His Phe Ser Leu Lys Glu Met Ser Thr Gly Tyr Glu Leu Met Gly Met
    115                 120                 125

His Arg Asn Ile Gln His Arg Val Asp Phe Leu Glu Trp Ala Pro Gly
130                 135                 140

Ala Arg Tyr Cys Ala Leu Ile Gly Asp Phe Asn Gly Trp Ser Thr Thr
145                 150                 155                 160

Gly Asn Cys Ala Arg Glu Gly His Phe Gly His Asp Asp Tyr Gly Tyr
                165                 170                 175

Trp Phe Ile Ile Leu Glu Asp Lys Leu Arg Glu Gly Glu Pro Asp
            180                 185                 190

Lys Leu Tyr Phe Gln Gln Tyr Asn Tyr Ala Glu Asp Tyr Gly Lys Gly
                195                 200                 205

Asp Thr Gly Ile Thr Val Glu Glu Ile Phe Lys Lys Ala Asn Asp Glu
    210                 215                 220

Tyr Trp Glu Pro Gly Glu Asp Arg Phe Ile Lys Ser Arg Tyr Glu Val
225                 230                 235                 240

Ala Ala Lys Leu Tyr Glu Glu Met Phe Gly Pro Asn Gly Pro Gln Thr
                245                 250                 255

Glu Glu Glu Leu Glu Ala Met Pro Asp Ala Ala Thr Arg Tyr Lys Thr
            260                 265                 270

Trp Lys Glu Gln Gln Lys Glu Asp Pro Ala Ser Asn Leu Pro Ser Tyr
    275                 280                 285

Asp Val Val Asp Ser Gly Lys Glu Tyr Asp Ile Tyr Asn Ile Ile Gly
    290                 295                 300

Asp Pro Glu Ser Phe Lys Lys Phe Arg Met Lys Gln Pro Pro Ile Ala
305                 310                 315                 320

Tyr Trp Leu Glu Thr Lys Lys Gly Arg Lys Gly Trp Leu Gln Lys Tyr
                325                 330                 335

Met Pro Ala Leu Pro His Gly Ser Lys Tyr Arg Val Tyr Phe Asn Thr
            340                 345                 350

Pro Asn Gly Pro Leu Glu Arg Val Pro Ala Trp Ala Asn Phe Val Ile
    355                 360                 365

Pro Asp Ala Gly Gly Met Ala Leu Ala Val His Trp Glu Pro Pro
    370                 375                 380

Glu Tyr Ala Tyr Lys Trp Lys His Lys Leu Pro Val Lys Pro Lys Ser
385                 390                 395                 400

Leu Arg Ile Tyr Glu Cys His Val Gly Ile Ser Gly Gln Glu Pro Lys
                405                 410                 415

Val Ser Ser Phe Asn Asp Phe Ile Ser Lys Val Leu Pro His Val Lys
            420                 425                 430

Glu Ala Gly Tyr Asn Ala Ile Gln Ile Ile Gly Val Val Glu His Lys
    435                 440                 445

Asp Tyr Phe Thr Val Gly Tyr Arg Val Thr Asn Phe Tyr Ala Val Ser
    450                 455                 460

Ser Arg Tyr Gly Thr Pro Asp Asp Phe Lys Arg Leu Val Asp Glu Ala
465                 470                 475                 480

His Gly Leu Gly Leu Leu Val Phe Leu Glu Ile Val His Ser Tyr Ala
                485                 490                 495

Ala Ala Asp Glu Met Val Gly Leu Ser Leu Phe Asp Gly Ala Asn Asp
            500                 505                 510

Cys Tyr Phe His Thr Gly Lys Arg Gly His His Lys Phe Trp Gly Thr
    515                 520                 525

Arg Met Phe Lys Tyr Gly Asp Leu Asp Val Leu His Phe Leu Leu Ser
530                 535                 540
```

Asn Leu Asn Trp Trp Val Glu Glu Tyr His Val Asp Gly Phe His Phe
545                 550                 555                 560

His Ser Leu Ser Ser Met Leu Tyr Thr His Asn Gly Phe Ala Ser Phe
                565                 570                 575

Thr Gly Asp Met Asp Glu Tyr Cys Asn Gln Tyr Val Asp Lys Glu Ala
            580                 585                 590

Leu Leu Tyr Leu Ile Leu Ala Asn Glu Val Leu His Ala Leu His Pro
        595                 600                 605

Asn Val Ile Thr Ile Ala Glu Asp Ala Thr Leu Tyr Pro Gly Leu Cys
    610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
            660                 665                 670

Asn Thr Asp Lys Met Leu Leu Tyr Ala Glu Asn His Asn Gln Ser Ile
        675                 680                 685

Ser Gly Gly Arg Ser Phe Ala Glu Ile Leu Ile Gly Asn Ser Leu Gly
    690                 695                 700

Lys Ser Ser Ile Ser Gln Glu Ser Leu Leu Arg Gly Cys Ser Leu His
705                 710                 715                 720

Lys Met Ile Arg Leu Ile Thr Ser Thr Ile Gly Gly His Ala Tyr Leu
                725                 730                 735

Asn Phe Met Gly Asn Glu Phe Gly His Pro Lys Arg Val Glu Phe Pro
            740                 745                 750

Met Ser Ser Asn Asn Phe Ser Phe Ser Leu Ala Asn Arg Arg Trp Asp
        755                 760                 765

Leu Leu Glu Asp Val Val His Tyr Gln Leu Phe Ser Phe Asp Lys Gly
    770                 775                 780

Met Met Asp Leu Asp Lys Asn Gly Arg Ile Leu Ser Arg Gly Leu Ala
785                 790                 795                 800

Asn Ile His His Val Asn Asp Thr Thr Met Val Ile Ser Tyr Leu Arg
                805                 810                 815

Gly Pro Asn Leu Phe Val Phe Asn Phe His Pro Val Asn Ser Tyr Glu
            820                 825                 830

Arg Tyr Ile Ile Gly Val Glu Glu Ala Gly Glu Tyr Gln Val Thr Leu
        835                 840                 845

Asn Thr Asp Glu Asn Lys Tyr Gly Gly Arg Gly Leu Leu Gly His Asp
    850                 855                 860

Gln Asn Ile Gln Arg Thr Ile Ser Arg Ala Asp Gly Met Arg Phe
865                 870                 875                 880

Cys Leu Glu Val Pro Leu Pro Ser Arg Ser Ala Gln Val Tyr Lys Leu
                885                 890                 895

Thr Arg Ile Leu Arg Ala
            900

<210> SEQ ID NO 15
<211> LENGTH: 20
<212> TYPE: DNA
<213> ORGANISM: Artificial Sequence
<220> FEATURE:
<223> OTHER INFORMATION: RT-PCR primer

<400> SEQUENCE: 15

```
gggggtgttg gctttgacta                                               20

<210> SEQ ID NO 16
<211> LENGTH: 20
<212> TYPE: DNA
<213> ORGANISM: Artificial Sequence
<220> FEATURE:
<223> OTHER INFORMATION: RT-PCR primer

<400> SEQUENCE: 16
cccttctcct cctaatccca                                               20

<210> SEQ ID NO 17
<211> LENGTH: 31
<212> TYPE: DNA
<213> ORGANISM: Artificial Sequence
<220> FEATURE:
<223> OTHER INFORMATION: B1_Asp primer

<400> SEQUENCE: 17
gatgggtacc agcacttcta cttggcagag g                                  31

<210> SEQ ID NO 18
<211> LENGTH: 30
<212> TYPE: DNA
<213> ORGANISM: Artificial Sequence
<220> FEATURE:
<223> OTHER INFORMATION: B2_Sal primer

<400> SEQUENCE: 18
tcaagtcgac cacaaccagt ccatttctgg                                    30

<210> SEQ ID NO 19
<211> LENGTH: 30
<212> TYPE: DNA
<213> ORGANISM: Artificial Sequence
<220> FEATURE:
<223> OTHER INFORMATION: KM2_Spe primer

<400> SEQUENCE: 19
tcaaactagt cacaaccagt ccatttctgg                                    30

<210> SEQ ID NO 20
<211> LENGTH: 21
<212> TYPE: DNA
<213> ORGANISM: Artificial Sequence
<220> FEATURE:
<223> OTHER INFORMATION: SoputE primer

<400> SEQUENCE: 20
cactttagaa ggtatcagag c                                             21

<210> SEQ ID NO 21
<211> LENGTH: 22
<212> TYPE: DNA
<213> ORGANISM: Artificial Sequence
<220> FEATURE:
<223> OTHER INFORMATION: So_put5' primer

<400> SEQUENCE: 21
gtatttctgc gaaggaacga cc                                            22

<210> SEQ ID NO 22
<211> LENGTH: 20
<212> TYPE: DNA
<213> ORGANISM: Artificial Sequence
<220> FEATURE:
```

-continued

```
<223> OTHER INFORMATION: So_putA primer

<400> SEQUENCE: 22
aacaatgctc tctctgtcgg                                                    20

<210> SEQ ID NO 23
<211> LENGTH: 30
<212> TYPE: DNA
<213> ORGANISM: Artificial Sequence
<220> FEATURE:
<223> OTHER INFORMATION: B3_Sal primer

<400> SEQUENCE: 23
gcttgtcgac gggagaattt tgtccagagg                                         30

<210> SEQ ID NO 24
<211> LENGTH: 31
<212> TYPE: DNA
<213> ORGANISM: Artificial Sequence
<220> FEATURE:
<223> OTHER INFORMATION: B4_Sal primer

<400> SEQUENCE: 24
gatcgtcgac agcacttcta cttggcagag g                                       31
```